US011346843B2

(12) United States Patent
Frauenfeld et al.

(10) Patent No.: US 11,346,843 B2
(45) Date of Patent: May 31, 2022

(54) SAPOSIN LIPOPROTEIN PARTICLES AND LIBRARIES FROM CRUDE MEMBRANES

(71) Applicant: Salipro Biotech AB, Stockholm (SE)

(72) Inventors: Jens Frauenfeld, Stockholm (SE); Robin Löving, Stockholm (SE)

(73) Assignee: Salipro Biotech AB, Stockholm (SE)

( * ) Notice: Subject to any disclaimer, the term of this patent is extended or adjusted under 35 U.S.C. 154(b) by 0 days.

(21) Appl. No.: 16/326,545

(22) PCT Filed: Aug. 21, 2017

(86) PCT No.: PCT/EP2017/071043
§ 371 (c)(1),
(2) Date: Feb. 19, 2019

(87) PCT Pub. No.: WO2018/033647
PCT Pub. Date: Feb. 22, 2018

(65) Prior Publication Data
US 2019/0204337 A1 Jul. 4, 2019

(30) Foreign Application Priority Data
Aug. 19, 2016 (EP) ................... 16184843

(51) Int. Cl.
| | |
|---|---|
| *A61K 9/127* | (2006.01) |
| *G01N 33/68* | (2006.01) |
| *A61K 38/18* | (2006.01) |
| *A61K 39/00* | (2006.01) |
| A61K 47/46 | (2006.01) |
| A61K 9/50 | (2006.01) |
| A61K 47/42 | (2017.01) |

(52) U.S. Cl.
CPC ......... *G01N 33/6842* (2013.01); *A61K 9/127* (2013.01); *A61K 38/18* (2013.01); *A61K 39/0012* (2013.01); *A61K 9/5068* (2013.01); *A61K 9/5089* (2013.01); *A61K 47/42* (2013.01); *A61K 47/46* (2013.01); *G01N 2570/00* (2013.01)

(58) Field of Classification Search
None
See application file for complete search history.

(56) References Cited

U.S. PATENT DOCUMENTS 9,884,128 B2 * 2/2018 Frauenfeld .......... A61K 47/543

FOREIGN PATENT DOCUMENTS

| CN | 102687021 A | 9/2012 |
|---|---|---|
| EP | 1 345 959 B1 | 5/2011 |
| EP | 1 596 828 B1 | 12/2011 |
| WO | 2011015870 A1 | 2/2011 |
| WO | 2014/095576 | 6/2014 |
| WO | 2014/095576 A1 | 6/2014 |
| WO | 2015/036549 A1 | 3/2015 |

OTHER PUBLICATIONS

Frauenfeld et al (Nature Methods 13:345-51 supplementary information) (Year: 2016).*
Schulze et al (Biochimica et Biophysica Acta 1793:674-83) (Year: 2009).*
Agranoff et al., "Chromatographic methods are employed to analyze and classify brain lipids", Analysis of Brain Lipids, NCBI Bookshelf, Siegel GJ, Agranoff BW, Albers RW et al., editors. Basic Neurochemistry: Molecular, Cellular and Medical Aspects, 6th edition, Philadelphia: Lippincott-Raven, 1999 (2 pages).
Ahn et al., "Crystal structures of saposins A and C", Protein Sciences, 15:1849-1857, 2006.
Albers and Meyer, "The archaeal cell envelope", Nature Reviews, 9:414-427, 2011.
Alberts et al., Molecular Biology of the Cell. 4th edition. New York: Garland Science; 2002. Chapter 2, Cell Chemistry and Biosynthesis, pp. 61-62.
Alberts et al., Molecular Biology of the Cell. 4th edition. New York: Garland Science; 2002. Chapter 10, Membrane Structure, pp. 583-614.

(Continued)

*Primary Examiner* — Christopher M Gross
(74) *Attorney, Agent, or Firm* — Honigman LLP; Fernando Alberdi; Jonathan P. O'Brien

(57) ABSTRACT

The invention is directed to a process for preparing a library of saposin lipoprotein particles, wherein the particles comprise membrane components from a cell or an organelle membrane and a lipid binding polypeptide that is a saposin-like protein belonging to the SAPLIP family of lipid interacting proteins or a derivative form thereof, wherein the process comprises the steps of a) providing a mixture of crude membrane vesicles obtained from a cell or an organelle membrane; b) contacting the mixture of step a) with the lipid binding polypeptide in a liquid environment; and c) allowing for self-assembly of the particles. The invention also provides a process for preparing a purified saposin lipoprotein particle comprising the steps of preparing a library according to the process described above and the additional step of f) purifying the saposin lipoprotein particle from the library. In addition, the invention provides a library of saposin lipoprotein particles and saposin lipoprotein particles obtainable according to the processes of the invention. These can be used in medicine, in particular in preventing, treating or lessening the severity of a disease or for use in a diagnostic method, a cosmetic treatment or for use as vaccination formulation or as a tool for drug development, drug screening, drug discovery, antibody development, development of therapeutic biologics, for membrane or membrane protein purification, for membrane protein expression, for membrane and/or membrane protein research, in particular lipidomics and proteomics, preferably for the isolation, identification and/or study of membranes and/or membrane proteins or creation of a lipidome or proteome database.

22 Claims, 15 Drawing Sheets
Specification includes a Sequence Listing.

(56) References Cited

OTHER PUBLICATIONS

Allen and Cullis, "Drug Delivery Systems: Entering the Mainstream", Science, 303:1818-1822, 2004.
Anderson et al., "Granulysin Crystal Structure and a Structure-derived Lytic Mechanism", J. Mol. Biol., 325:355-365, 2003.
Brain Extract from bovine brain Type I, Folch Fraction I, Sigma-Aldrich, https://www.sigmaaldrich.com/catalog/product/sigma/b1502?lang=en..., 2 pages.
Brügger et al., "The HIV lipidome: A raft with an unusual composition", PNAS, 103(8):2641-2646, 2006.
Bruhn, "A short guided tour through functional and structural features of saposin-like proteins", Biochem. J., 389:249-257, ,2005.
Chan and Boxer, "Model Membrane Systems and Their Applications", Curr Opin Chem Biol, 11(6):581-587, 2007.
De Alba et al., "Solution Structure of Human Saposin C: pH-Dependent Interaction with Phospholipid Vesicles", Biochemistry, 42(50):14729-14740, 2003.
De Rosa et al., "Structure, Biosynthesis, and Physicochemical Properties of Archaebacterial Lipids", Microbiological Reviews, 50(1):70-80, 1986.
European Search Report, EP 16 18 4843, dated Mar. 1, 2017 (5 pages).
Frauenfeld et al., "A novel lipoprotein nanoparticle system for membrane proteins", Nat Methods, 13(4):345-351, 2016.
Fürst and Sandhoff, "Activator proteins and topology of lysosomal sphingolipid catabolism", Biochimica et Biophysica Acta, 1126:1-16, 1992.
Hawkins et al., "Solution Structure of Human Saposin C in a Detergent Environment", J. Mol. Biol., 346:1381-1392, 2005.
Henikoff and Henikoff, "Amino acid substitution matrices from protein blocks", Proc. Natl. Acad. Sci. USA, 89:10915-10919, 1992.
Liepinsh et al., "Saposin fold revealed by the NMR structure of NK-lysin", Nature Structural Biology, 4(10):793-795, 1997.
Lorizate et al., "Comparative lipidomics analysis of HIV-1 particles and their producer cell membrane in different cell lines", Cellular Microbiology, 15(2):292-304, 2013.
Munford et al., "Saposin-like proteins (SAPLIP) carry out diverse functions on a common backbone structure", Journal of Lipid Research, 36:1653-1663, 1995.
Needleman and Wunsch, "A General Method Applicable to the Search for Similarities in the Amino Acid Sequence of Two Proteins", J. Mol. Biol., 48:443-453, 1970.

O'Brien et al., "Coding of Two Sphingolipid Activator Proteins (SAP-1 and SAP-2) by Same Genetic Locus", Science, 241:1098-1101, 1988.
Overington et al., "How many drug targets are there?", Nature Reviews Drug Discovery, 5:993-996, 2006.
PCT International Search Report, PCT/EP2017/071043, dated Oct. 17, 2017 (5 pages).
International Preliminary Report on Patentability, PCT/EP2017/071043, dated Nov. 13, 2018 (6 pages).
Popovic et al., "Structure of saposin A lipoprotein discs", PNAS, 109(8):2908-2912, 2012.
Qi et al., "Cancer-Selective Targeting and Cytotoxicity by Liposomal-Coupled Lysosomal Sapison C Protein", Clin Cancer Res, 15(18):5840-5851, 2009.
Wallin and Heijne, "Genome-wide analysis of integral membrane proteins from eubacterial, archaean, and eukaryotic organisms", Protein Science, 7:1029-1038, 1998.
Wang et al., "Phospholipid vesicle fusion induced by saposin C", Archives of Biochemistry and Biophysics, 415:43-53, 2003.
Welten-Verstegen et al., "Lipid Mediated Glycosylation of Endogenous Proteins in Isolated Plasma Membrane of *Saccharomyces cerevislae*", Journal of Bacteriology, 141(1):342-349, 1980.
Frauenfeld el al., "A novel lipoprotein nanopartide system for membrane proteins", Nature Methods, 13(4):345-351, 2016.
Popovic et al., "Structure of saposin A lipoprotein discs", Proceedings of the National Academy of Sciences, National Academy of Sciences, US, 109(8):2908-2912, 2012.
Welten-Verstegen et al., "Lipid Mediated Glycosylation of Endogenous Proteins in Isolated Plasma Membrane of *Saccharomyces-Cerevisiae*", Journal of Bacteriology, 141(1):342-349, 1980.
Brain Extract from bovine brain Type I, Folch Fraction 1, Sigma-Aldrich, https://www.sigmaaldrich.com/catalog/product/sigma/b1502?lang=en..., 2 pages.
Agranoff et al., "Chromatographic methods are employed to analyze and classify brain lipids", Analysis of Brain Lipids, NCBI Bookshelf, Siegel GJ, Agranoff BW, Albers RW et al., editors. Basic Neurochemistry: Molecular, Cellular and Medical Aspects, 6th edition, Philadelphia: Lippincott-Raven, 1999 (1 page).
"Physiology" 2nd Edition, edited by Zhu, Danian Zhu, Fudan University Press, pp. 8-15, ISBN 978-7-309-11454-6/R.1463. with English Abstract. Considered to the extent of the English Abstract.
Chinese Search Report dated Aug. 4, 2021, with English translation, 4 pages.

* cited by examiner

SAPOSIN LIPOPROTEIN PARTICLES AND LIBRARIES FROM CRUDE MEMBRANES

CROSS-REFERENCE TO RELATED APPLICATIONS

This application claims the benefit of and priority under 35 U.S.C. § 371 to International Patent Cooperation Treaty Application No. PCT/EP2017/071043, filed Aug. 21, 2017, which claims the benefit of priority to European Patent Application No. 16184843.7, filed Aug. 19, 2016, the entire contents of both disclosures are incorporated herein by reference in their entireties.

The invention relates to processes for preparing a library of lipoprotein particles from cell or organelle membranes and purifying lipoprotein particles therefrom as well as to a library of lipoprotein particles and purified lipoprotein particles themselves and their uses.

BACKGROUND OF THE INVENTION

In the last decade, research in the life sciences, and drug discovery in particular, has been rapidly changing. Advances in molecular biology, computing, genomics, proteomics and lipidomics, permitted to develop novel methods for research and drug discovery.

In this area of research, libraries of a cell's or a cell organelle's genome, proteome, or lipidome have proven very useful in studying gene, protein or lipid functions as well as discovering gene, protein or lipid drug targets. Whereas the field of genomic and DNA libraries is well advanced, there still is an urgent need to develop improved methods for preparing membrane proteome and/or lipidome libraries.

Drug discovery is based on the discovery, selection and further development of lead compounds that have a particular physiological activity in certain diseases and/or, if a compound library is available, the identification of new drug targets in the cells that are involved in the disease. Oftentimes drug targets are lipids, lipid domains or membrane proteins, e.g. receptors or transporters, embedded in cell or organelle membranes of target cells. Therefore, elucidation of the structure and function of lipids, lipid domains and membrane proteins embedded in their natural membrane environment as well as the possibility to screen a compound or compound library against a complex library of possible lipid and membrane protein targets is highly desired in life science research in general, and in the development of new medicines in particular.

For soluble proteins of a cell or organelle, it is easily possible to prepare a library of the soluble cellular or organelle proteome by simply isolating the soluble protein fraction. Unfortunately, membranes (and the membrane proteins and lipids contained therein) are not soluble in the detergent-free systems that are usually used in drug screening procedures and most functional assays employed in life science research. Thus, current membrane proteome or lipidome libraries are mostly in a detergent-solubilized state or in a denatured state. The latter may be useful for protein or lipid identification techniques, such as mass spectrometry, but is incompatible with functional analysis of membrane proteins or lipids in their natural environment, an underlying requirement for successful research and drug development in this area.

These difficulties in purification, isolation and in functional analysis have delayed research on membrane lipidomes and membrane proteomes.

Lipidomics is the large-scale study of pathways, compositions and networks of cellular lipids in biological systems and involves the identification and quantification of cellular lipid molecular species and their interactions with other lipids, proteins, and other metabolites. The word "lipidome" is used to describe the sum of all lipids and/or the lipid profile of a cell, tissue, organism, or ecosystem and is a subset of the "metabolome" which also includes the other major classes of biological molecules: proteins, amino-acids, sugars and nucleic acids. Lipidomics is a relatively recent research field that has been driven by rapid advances in technologies such as mass spectrometry (MS), nuclear magnetic resonance (NMR) spectroscopy, fluorescence spectroscopy and computational methods, coupled with the recognition of the role of lipids in many metabolic diseases such as obesity, atherosclerosis, stroke, hypertension and diabetes. This rapidly expanding field complements the huge progress made in genomics and proteomics, all of which constitute the family of systems biology.

The lipidome is enormously complex and lipids have essential roles in membrane dynamics, energy metabolism, and signaling, where lipid structure is a key determinant of the biological effects. Analytical methods such as lipidomics are essential for increasing the current biological understanding of biologically relevant lipids in basic research and pharmaceutical drug discovery and development. To this end, it is desirable to be able to provide lipidome libraries in which the lipids are maintained in a state as close as possible to their natural environment in the cell or organelle membrane.

A lipidomic research approach is applicable to all therapeutic areas, including cardiovascular diseases, diabetes, cancer, neurological diseases and autoimmune, as well as inflammatory diseases. A basic requirement of a successful lipidomic study is an adequate pre-analytical sample, preferentially a lipidome library allowing for fast production, convenient handling and short storage times, because some lipids and naturally occurring lipid domains can be unstable.

Lipids also offer the promise of novel biomarker solutions in many areas. In addition, they might also serve as potential pharmacodynamic read-outs for experimental or existing therapies. Thus, lipids could also fuel companion diagnostic development and, therefore, support more personalized treatment approaches. Also in this respect, it is desirable to provide convenient and robust methods for preparing lipidome libraries. Lipidomics can also be used for studying various experimental disease models and this could provide an enormous boost to translational medicine.

Proteomics, on the other hand, is the large-scale study of proteins, particularly their structures and functions. Proteins are vital parts of living organisms, as they are the main components of the physiological metabolic and signaling pathways of cells. The proteome is the set of proteins produced and comprised in an organism, cell, organelle or system. The membrane proteome is the set of membrane and membrane-associated proteins produced and comprised in an organism, cell, organelle or system membrane. The proteome can vary over time and conditions or stresses that a cell or organism undergoes or experiences, e.g. in disease.

The membrane proteome is a particularly interesting research object because of the many functions that membrane proteins exert in cellular systems and disease. Being rich in potential drug targets, a library encompassing the membrane proteome of a given cell or organelle membrane would be highly desired for screening processes. In addition, the isolation and identification of unknown membrane proteins offers the prospect of discovering new pharmaceutical targets and identifying key biochemical receptors. As described above, the preparation and subsequent use of membrane proteome libraries has thus far been hampered by the insolubility of membranes and membrane components in detergent free systems. Interactions between membrane protein targets and soluble ligands are difficult to study in vitro due to the insolubility of membrane proteins in non-detergent systems.

Hydrophobic compounds such as membrane proteins and lipids are notoriously difficult to handle and represent two of the major challenges for pharmaceutical or life-science research, and applications: (i) rendering insoluble hydrophobic compounds such as lipids or membrane proteins soluble in aqueous solutions and (ii) the handling and administration of such hydrophobic matter as therapeutic, research or diagnostic agents.

Membrane proteins are encoded by approximately 30% of all ORFs (Wallin and von Heijne, Protein Science 1998 April; 7 (4):1029-38) and represent an important class of drug targets since the majority of drugs, i.e. more than 60%, target in fact this class of proteins (Overington et al., Nature Reviews Drug Discovery 5, 993-996 (December 2006)). Membrane proteins play essential roles in many biological processes, such as signal transduction, transport of molecules and energy, recognition and cell-to-cell communication. Yet, membrane proteins are difficult to study due to their insolubility and tendency to aggregate when extracted from their natural lipid bilayer environment. In order to maintain the integrity of membrane proteins, an artificial hydrophobic environment is needed. Here, detergent micelles are most commonly employed which may, however, negatively impact on biocompatibility, can have adverse affects on membrane protein activity and may interfere with experimental conditions for assays.

Another major pharmacological challenge is represented by the administration and delivery of hydrophobic proteins and/or lipids as therapeutic or diagnostic agents. Due to the limited solubility of these hydrophobic agents, they are prone to aggregation, leading to locally highly concentrated drug particles that may cause high toxicity, unwanted immune responses and render the drug inactive (Allen and Cullis, SCIENCE, 303 (5665): 1818-1822, Mar. 19, 2004).

Therefore, applications that incorporate hydrophobic agents such as membrane proteins or lipids into soluble particles are highly desired. Current methods that address these two challenges involve amongst others liposomes and reconstituted high-density lipoprotein (rHDL) particles (Chan and Boxer, Current Opinion in chemical Biology 11:1-7, 2007).

EP 1 596 828 B1 describes disc-shaped bioactive agent delivery particles comprising an apolipoprotein which tightly surrounds a lipid bilayer in a double belt-like fashion. The interior of said particles is formed by the hydrophobic region of the lipid bilayer. This is in contrast to liposomes, which are closed spherical bilayer shells containing an aqueous interior. The disc-shaped bioactive agent delivery particles described in EP 1 596 828 B1 have a Stokes diameter of about 10 nm and are proposed for use as delivery vehicles for hydrophobic pharmaceutical drugs such as amphotericin B or camptothecin.

EP 1 345 959 B1 describes a similar type of nanoscale particle with a diameter of about 10 nm and a height of about 5.5 nm. The particles are disc-shaped and composed of (i) an artificial membrane scaffold protein, (ii) a phospholipid bilayer and (iii) at least one hydrophobic or partially hydrophobic membrane protein. See FIG. 1a herein below. Said membrane scaffold protein again surrounds the lipid bilayer in a double belt-like fashion and is a derivative or a truncated form of human apolipoprotein A-1, lacks the N-terminal globular domain of human apolipoprotein A-1, is amphipathic and forms at least one α-helix and will, in aqueous environment, self-assemble with a phospholipid or mixture of phospholipids into a nanoscale particle of this discoidal shape. Such an engineered membrane scaffold protein (MSP) shall provide stability, size homogeneity and useful functionalities to the nanoscale discoidal lipoprotein particle.

However, there are several drawbacks with this currently available nanodisc technology in that, for example, a removal of detergent is required during assembly of the particles. Moreover, the size homogeneity provided by the tight double-belt like fit of the apolipoprotein-derived MSP seems to go at the expense of a fixed minimum particle size and a limitation as to the maximum diameters obtainable with the methods of the prior art.

Recently, novel nanoparticle technologies involving the saposin family of lipid binding proteins have been suggested (see Qi et al. (2009) Clin Cancer Res 15(18):5840-5851, Popovic et al., PNAS, Vol. 109, No. 8 (2012) 2908-2912, WO 2014/095576 A1 and WO 2015/036549 A1)

The saposin-family comprises 4 small (~80 amino acids) proteins, saposin A to D, that bind and/or interact with lipids and function as essential cofactors for several lysosomal enzymes in sphingolipid catabolism (cf. Bruhn, Biochem J. (2005) 389, 249-257 and references cited therein). Saposins have been described to prefer negatively charged lipids and low pH, exhibiting markedly increased activities at acidic pH, with a pH optimum at the intra-lysosomal pH of 4.75. Saposin A, B, C, and D are proteolytically hydrolyzed from a single large precursor protein, prosaposin. The complete amino acid sequences for saposins A, B, C and D have been reported as well as the genomic organization and cDNA sequence of prosaposin (O'Brien et al. (1988) Science 241, 1098-1101; Furst et al (1992) Biochim Biophys Acta 1126: 1-16). Saposin C is capable of inducing membrane fusion of phospholipid-containing vesicles in an acidic environment (Archives of Biochemistry and Biophysics 2003 Jul. 1; 415(1): 43-53), a feature not exhibited by the other saposins. Qi et al. (2009) Clin Cancer Res 15(18):5840-5851 report on saposin C-coupled dioleoylphosphatidylserine nanovesicles (SapC-DOPS) that contain an aqueous interior, have a mean diameter of about 190 nm and show tumor-targeting activity in vivo. In SapC-DOPS, saposin C or a peptide derived thereof acts as homing peptide for the liposome it is attached to. Saposin C then targets the liposome to cancer cells exposing phosphatidylserine on the outer leaflet of the cell membrane. The authors believe that a unique acidic microenvironment around cancer cells due to extracellular leakage of lysosomal enzymes makes tumor tissue an optimal target for saposin C. According to Qi et al., SapC-DOPS liposomes are prepared by drying solvent-dissolved purified phospholipids under N2 (g), dispersing the dry phospholipids in acidic buffer (pH 5) containing purified saposin C, diluting the mixture 50× in a physiologic aqueous solution and facilitating nanovesicle assembly by subsequent sonication.

Popovic et al., PNAS, Vol. 109, No. 8 (2012) 2908-2912 report on the structure of saposin A detergent discs. Saposin A exists in a soluble and a lipid/detergent-bound state. In the absence of lipid, saposin A adopts a closed monomeric apo conformation. By contrast, the saposin A detergent disc structure reported by Popovic et al. reveals two chains of saposin A in an open conformation encapsulating 40 internally bound detergent molecules organized in a highly ordered bilayer-like hydrophobic core.

Besides the crystallization of saposin A detergent discs, Popovic et al. also describe the preparation of soluble lipid-saposin A complexes at pH 4.75 by a method requiring multiple steps. First, a uniform fraction of large unilamellar liposome vesicles is prepared by drying chloroform-dissolved purified lipids under N2 (g), dispersing the dry lipids by vortex mixing in acidic buffer (50 mM sodium acetate pH 4.8, 150 mM NaCl), submitting the suspension to 10 cycles of freezing and thawing, blending in a vortex mixer for 5 min and extruding the mixture through a 200 nm filter. Mixing the thus prepared large unilamellar artificial liposome vesicles with purified saposin A in acidic buffer resulted in soluble lipid-saposin A particles. The particle showed a narrow size distribution around an average hydrodynamic (Stokes) radius of 3.2 nm and contained about 5:1 lipid molecules per saposin A chain. The exact size of the particles was only moderately affected by the lipid to protein molar ratio and the composition of the liposomes. The authors observed similar 3.2 nm particles regardless of whether or not anionic phospholipids, cholesterol, or glycosphingolipids were present in the liposomal mixtures. In all cases, a single peak was observed in the size range of a Stokes radius of 3.2 nm, indicating a relatively narrow distribution of species. Hence, the technology of this publication is limited to a pH value of 4.75, to the aforementioned size of the particles, and includes a laborious upstream liposome preparation step.

WO 2014/095576 A1 for the first time showed that it is possible to incorporate purified, detergent solubilized hydrophobic cargo molecules or purified, detergent solubilized membrane proteins into Saposin-lipid particles using detergent solubilized and purified lipids (see FIG. 1b herein below). The method described in WO 2014/095576 A1 thus used purified detergent solubilized components and by this was contrasted from the synthetic liposomes that were prepared from purified lipids in the method of Popovic et al.

WO 2015/036549 A1 expanded the method described in WO 2014/095576 A1 to the incorporation of solubilized antigen molecules (shown for viral membrane proteins) from well-defined and purified HIV-1 virus like particles (VLP). According to the Examples of WO 2015/036549 A1, the pre-purified VLPs are lysed, the HIV-1 membrane spike protein is solubilized with detergent and then contacted with Saposin A. In general terms, WO 2015/036549 A1 also suggests that solubilized antigen molecules from bacterium, fungus, protozoan, parasite or a human or animal neoplastic/tumor could in principal be used, however, no experimental details are provided. And, again, only purified components are used in a detergent-solubilized state, i.e. without the native membrane context being maintained.

A wide variety of hydrophobic agents, such as membrane proteins or lipids, could potentially benefit from the apolipoprotein- or Saposin-derived nanodisc technology described in the prior art. It can be easily imagined, that preparation of a lipidome and membrane proteome library would necessitate the nanodisc particles to be extremely flexible with regard to size and cargo compatibility. However, due to the 3.2 nm size limitation of the saposin A derived particles reported in Popovic et al., it seems that—if at all—only small molecules could be incorporated into such particles at the acidic pH disclosed therein. Whereas bulky hydrophobic compounds and large biomolecules such as (oligomeric) membrane proteins can be incorporated into the Apolipoprotein A derived nanodiscs of the prior art, the maximum possible diameter is still limited by the double-belt like Apolipoprotein A perimeter of these particles. In addition, the 10 nm Apolipoprotein A derived nanodiscs may be too large for certain applications.

Furthermore, the methods described in all of the above apolipoprotein- or Saposin-related prior art are sophisticated in their level of experimental detail and rely on well-defined systems of purified, detergent-solubilized components. Thus, they are not expected to work when directly employing crude membranes as starting material, which are characterized by a highly complex structure and composition. If one first were to purify and solubilize the membrane lipidome and proteome from a cell or organelle membrane, one would, however, remove the membrane proteins and lipids from their natural environment and context which can lead to a loss of function, loss of content, complexity and corresponding bias in the library's composition. In addition, such process would be complicated and elaborate because not all membrane proteins and membrane lipids have the same requirements regarding handling, detergent solubilization and stability.

Also, the above-described processes of the prior art that show incorporation of bacterial or eukaryotic membrane proteins, use synthetic or purified lipids to reconstitute the lipoprotein particles. Thus the lipids and the membrane proteins present in the lipoprotein particles are derived of different sources and do not reflect the naturally occurring environment. Such mimicking of the naturally occurring environment is, however, highly desired for obtaining libraries that will yield meaningful results in research and screenings, enhancing the possibility of being transferable and verifiable in their native cellular, and possibly disease, context.

In summary, the prior art methods used for incorporation of prokaryotic or eukaryotic membrane components, such as proteins and lipids, into nano particle structures mostly includes the component's extraction, solubilization and reassembly into particles, especially wherein synthetic lipids or lipids purified from a completely different source are used. These particles do not resemble the natural occurring membrane from which they were obtained. This makes investigation of the natural occurring membrane environment impossible. In addition, these known procedures carry the risk of denaturation of the protein or destabilization of lipids and lipid domains during purification and extraction. Moreover, it cannot be excluded that the proteins and/or lipids loose their native structure and function when divorced from its natural environment.

The Saposin-related prior art only teaches incorporation of detergent-purified and/or detergent-solubilized membrane proteins of prokaryotic or eukaryotic origin or solubilized antigen from purified, artificial virus-like particles. These approaches provide a highly homogenous nanodisc population containing the purified membrane protein of interest reassembled in a lipid environment that is well defined, but usually completely different from the naturally occurring membranes of prokaryotic, archaeal and eukaryotic organisms.

In contrast, these naturally occurring membranes of prokaryotic, archaeal and eukaryotic organisms are highly complex and contain a highly diverse array of proteins and lipids that interact to form a complex superstructure with the capacity to regulate various cellular processes. The handling and incorporation of such complex membranes without the detergent solubilization and purification steps taught in the prior art methods appears nearly impossible to conduct as the complex natural membrane structures are not expected to be as easy to handle as purified components. In particular, natural membranes also contain complex mixtures and domains of various lipid components consisting primarily of different types of phospholipids, including POPC (1-palmitoyl-2-oleoyl-sn-glycero-3-phosphocholine), POPS (1-palmitoyl-2-oleoyl-sn-glycero-3-phospho-L-serine), and sphingomyelin, and other lipids, including cholesterol. Furthermore, the membranes form domains such as lipid rafts that can, e.g., contain a percentage of cholesterol and sphingomyelin significantly higher than that of the regular plasma membrane that aid in protein signaling. A given membrane protein might only function properly in its given natural membrane context.

Taken together, the membranes of prokaryotic, archaeal and eukaryotic organisms show a high degree of complexity, that arises from the intricate interplay between membrane proteins and a variety of lipids surrounding them in their native context.

The prior art does not contemplate, and certainly does not teach or suggest, a feasible proposal for preparing native state membrane proteome and lipidome libraries in the form of Saposin-derived particles.

However, as described above, such libraries, in which the membrane proteome or lipidome components remain preserved in their natural environment are highly desired. For example, elucidation of the structure, function and interactions of membrane proteins in vitro in their naturally occurring environment, i.e. embedded in the lipids of the membrane in which they are present and active in vivo, would be helpful in identifying drug targets and understanding underlying mechanisms and reactions occurring at the level of cell and organelle membranes. Thus, there is a need to develop novel methods for preparing libraries from cell or organelle membranes that allow preserving the membrane lipids and membrane proteins in their natural environment so that they maintain their respective structures and functions. The provision of a library reflecting the lipid and protein composition of crude membrane would allow for studies of the lipidome, proteome or membrane structure of a certain cell, organelle or organism at a hitherto unattainable level.

SUMMARY OF THE INVENTION

Against this background, the problem underlying the invention can be seen in the provision of improved lipoprotein particles and improved libraries of lipoprotein particles and methods for their production.

This problem is solved by the processes according to the invention which employs crude membrane vesicles as starting material for preparing a library of lipoprotein particles comprising a lipid binding polypeptide and at least parts or components of a cell or organelle membrane, wherein the lipid binding polypeptide is a saposin-like protein or a derivative or truncated form thereof.

The invention provides a process for preparing a library of saposin lipoprotein particles, wherein the particles comprise membrane components from a cell or an organelle membrane and a lipid binding polypeptide that is a saposin-like protein belonging to the SAPLIP family of lipid interacting proteins or a derivative form thereof, wherein the process comprises the steps of a) providing a mixture of crude membrane vesicles obtained from a cell or an organelle membrane;
b) contacting the mixture of step a) with the lipid binding polypeptide in a liquid environment;
c) allowing for self-assembly of the particles.

The process of the invention can be extended into a purification process for a particular type of saposin lipoprotein particle, which process then comprises the steps of preparing a library according to the above-described process and the additional step of f) purifying at least one type of saposin lipoprotein particle from the library.

The saposin lipoprotein particles described herein comprise membrane components, in particular membrane lipids and, optionally, also membrane proteins, all derived from a cell or an organelle membrane. The saposin lipoprotein particles described herein further comprise a lipid binding polypeptide that is a saposin-like protein (SAPLIP) belonging to the SAPLIP family of lipid interacting proteins or a derivative form thereof is obtainable by the methods of the invention. These saposin lipoprotein particles described herein are also referred to herein as "Salipro particle(s)", "saposin lipoprotein particle(s)" or "particle(s) of the invention". The libraries obtainable by the method of the invention and comprising a mixture of different Salipro particles are also referred to as "Salipro particle libraries" herein The process according to the invention has the advantage that it is relatively easy to conduct and surprisingly yields libraries of Salipro particles that reflect the diversity and complexity of the crude membrane used as starting material and incorporate and preserve the lipid and membrane proteins components contained therein in their natural membrane environment. A wide variety of membranes can be used in the process according to the invention. The crude membrane vesicles used in step a) are prepared from crude membranes of cell or organelles. Crude membrane vesicles obtained from cell and/or organelle membranes of many organisms can be used. It was surprising that Salipro particles could be obtained also when complex membranes of eukaryotic, prokaryotic or archaeal cells were employed as starting material instead of the highly purified, detergent-solubilized starting materials required in the prior art preparation methods.

The Salipro particles present in the library obtained with the process according to the invention vary in size and composition and contain different mixtures of membrane components, reflecting the membrane lipidome and proteome of the crude membrane used as starting material. Also components of the crude membranes obtained from cell organelles can be incorporated in the Salipro particles.

The skilled person knows that membranes obtained from cells and organelles display a complex and very heterogenic mix of components that are expected to also interact with the lipid-binding polypeptide and other reagents used in the process of preparing lipoprotein particles. This was expected to lead to little product, low quality product or highly undefined products. Against this background, it was surprising that complex crude membrane can be used and its diverse array of components can be readily incorporated into the Salipro particles to form corresponding membrane proteome/lipidome libraries. In contrast to the process according to the invention, which employs crude membrane vesicles, the prior art processes employing Saposin-like proteins together with eukaryotic or prokaryotic membrane proteins predominantly use purified or synthetic lipids that are re-assembled with highly purified proteins or so that controlled conditions are provided.

The process according to the invention provides libraries that efficiently capture membrane components, in particular membrane lipids and membrane proteins, directly from complex cellular membranes. As the process according to the invention uses crude membrane vesicles, i.e. parts and/or components of intact physiological membranes that were not extracted or purified as in the prior art methods, and still contain both their natural lipid as well as their natural membrane protein repertoire, the Salipro particle libraries obtained by the process according to the invention comprise a complex array of membrane components. This permits the possibility of providing of a library depicting a lipidome and/or membrane proteome from a particular cell or organelle.

In particular, the process according to the invention permits the preparation of a library comprising a heterogenic mixture of Salipro particles with different membrane lipid and optionally membrane protein compositions. As described above, the provision of such a library comprising an array of Salipro particles made up of a heterogenic array of membrane components, i.e. membrane lipids and/or membrane proteins embedded in their natural environment, is a very useful tool in drug discovery, antibody generation, membrane (protein or lipid) research, lipidomics, proteomics or medical, cosmetic and diagnostic applications.

Practical experiments revealed that the size of the Salipro particles self-adjusts to the nature of the incorporated membrane component, e.g. to the size of the incorporated membrane protein. Salipro particles are surprisingly flexible in size and thus, in contrast to other scaffold proteins and agents employed in membrane library technology today, allow for even more flexibility and/or variation of different lipid (and optionally membrane) specificities in the membrane lipidome or proteome to be resembled by the library.

Without being bound to theory, it appears that the process according to the invention permits the Salipro particles to adjust their size to the nature of the incorporated membrane components. This is advantageous over the size limitation of other prior art particles. This flexibility apparently also enables to incorporate membrane proteins in their natural environment, e.g. the membrane lipids or other cell components associated with the membrane protein and potentially required for maintaining the protein's structure and/or function. It was also surprising to discover that although such complex membrane parts and components varying in size and composition were successfully incorporated into the Salipro particles following the process of the invention, the libraries thus obtained were nevertheless stable and could be further processed, handled, purified and/or analyzed without difficulties. The Salipro particles obtained with the process according to the invention are easy to produce and can maintain a uniform quality and composition over time, thereby offering the possibility of providing a stable and valuable library that can be subjected to further steps and applications.

Without being bound to theory, it appears that the contacting of the crude membrane vesicles with a saposin-like protein or a derivative or truncated form thereof in step b) and the self-assembly in step c) of the method of the invention provides a robust structure which is stable in aqueous solutions over a wide pH range, in particular at physiological pH, and allows larger particles than the 3.2 nm saposin A-derived lipoprotein particles obtained from synthetically prepared liposomes according to the prior art teaching of Popovic et al.

As described in the introduction, the importance of membrane proteins in therapeutic developments necessitates the discovery of innovative methods for interrogating membrane proteins in cell free mediums, preferably in a detergent-free environment.

The libraries and Salipro particles obtainable by the method of the invention fulfill this requirement. The libraries and Salipro particles, once obtained, are stable in cell free mediums and detergent-free environments. In one embodiment, employment of a detergent is not mandatory in the process.

Crude membranes contain a plethora of different membrane proteins and lipid components. Contrary to the expectation that in the absence of detergent, membrane proteins are not soluble in detergent-free buffer systems and aggregate, leading to the formation of a large void-peak in SEC analysis, practical experiments revealed that, once embedded in Salipro particles, the membrane proteins and membrane lipid components remain soluble in detergent-free buffer systems.

In another aspect of the invention, the library of Salipro particles can be used to further purify a particular type of Salipro-particle, i.e. containing a particular membrane protein or lipid composition of interest.

Further, the libraries and particles obtainable by the method of the invention can be used as a tool for drug development, drug screening, drug discovery, antibody development, development of therapeutic biologics, for membrane or membrane protein purification, for membrane protein expression, for membrane and/or membrane protein research, in particular lipidomics and proteomics, preferably for the isolation, identification and/or study of membranes and/or membrane proteins or creation of a lipidome or proteome database.

Finally, the library of Salipro particles or the Salipro particle can be used in medicine, in particular for use in preventing, treating or lessening the severity of a disease or for use in a diagnostic method, a cosmetic treatment or for use as vaccination formulation.

DETAILED DESCRIPTION OF THE INVENTION

The invention provides a process for preparing a library of saposin lipoprotein particles, wherein the particles comprise membrane components from a cell or an organelle membrane and a lipid binding polypeptide that is a saposin-like protein belonging to the SAPLIP family of lipid interacting proteins or a derivative form thereof, wherein the process comprises the steps of
  a) providing crude membrane vesicles obtained from a cell or an organelle membrane;
  b) contacting the mixture obtained after step a) with the lipid binding polypeptide in a liquid environment;
  c) allowing for self-assembly of the particles.

The process according to the invention in particular provides a library of Salipro particles, wherein each Salipro particle comprises the lipid binding polypeptide, membrane lipids, and, optionally, a membrane protein. The term "membrane protein" as used herein does not encompass the lipid binding polypeptide of the invention. "Membrane lipids" as used herein are mixtures of membrane lipids, in particular naturally occurring mixtures of membrane lipids. "Membrane lipids" as used herein are derived from the crude cell or organelle membrane that the crude membrane vesicles were prepared from. Membrane lipids as used herein therefore do not encompass pre-purified lipids or lipid mixtures.

"Crude cell or organelle membrane" as used herein are cell or organelle membranes or portions thereof that are no longer fully intact but still comprise essentially the natural membrane composition, in particular regarding membrane lipids and membrane protein. For example, a crude membrane fraction obtained after cell disruption or lysis of cells or organelles is a "crude cell or organelle membrane" according to the invention. "Crude cell or organelle membranes" necessarily comprise the natural membrane components present in the cell and organelle. In particular, "crude cell or organelle membranes" comprise both membrane lipids as well membrane proteins. In a preferred embodiment, the membrane lipids and the membrane protein present in a Salipro particle of the invention or the membrane lipids and the membrane proteins present in the Salipro particle library of the invention are obtained from the same cell and/or cell organelle membrane.

As crude cell or organelle membranes are no longer fully intact cell or organelle membranes, they spontaneously form crude membrane vesicles due to hydrophobic interactions between two given membrane rupture sites. Thus, in one embodiment, "crude cell or organelle membranes" comprise "crude membrane vesicles" or both terms are used synonymously.

The term "library" according to the invention means a set (complex plurality) of different Salipro particles. In particular, the difference can lie in the size and composition of the particles, especially in the composition of the membrane components contained therein, i.e. membrane lipids, and, optionally, membrane proteins. Typically the libraries are a mixture of "lipid-only particles" (see FIGS. 2a and 2b) and different kinds of membrane protein containing Salipro particles (see FIGS. 2c to 2f). The particles in the library can also differ in their content and composition of different membrane lipids. Preferably, some particles in the library differ in the fact whether or not and which membrane protein they contain.

The membrane lipids and/or the membrane proteins in the Salipro particles are obtained from a membrane of a certain cell, all membrane of a certain cell, a membrane of a certain organelle, all membrane of a certain organelle, all membrane of a certain individual or organism or any other possible membrane sample comprising membrane from a cell or organelle of a cell. Preferably, the Salipro particles contained in the library differ in their membrane lipid and/or membrane protein composition. Preferably, they differ in their membrane protein composition.

In a preferred embodiment, the Salipro particles are disc-shaped. In another preferred embodiment, the Salipro particles do not comprise an aqueous or hydrophilic core. In yet another embodiment, the Salipro particles are disc-shaped and do not comprise an aqueous or hydrophilic core.

Accordingly the invention also provides a process for preparing a library of disc-shaped saposin lipoprotein particles, wherein the particles comprise membrane lipids and a lipid binding polypeptide that is a saposin-like protein belonging to the SAPLIP family of lipid interacting proteins or a derivative form thereof, wherein the particles do not comprise a hydrophilic or aqueous core, and wherein the process comprises the steps of
  a) providing crude membrane vesicles obtained from a cell or an organelle membrane;
  b) contacting the mixture obtained after step a) with the lipid binding polypeptide in a liquid environment;
  c) allowing for self-assembly of the particles, particularly preferred at a pH from 2.0 to 10.0, in particular 6.0 to 10.0, preferably from 6.0 to 9.0, particularly preferred from 7.0 to 9.0, and most preferred from 7.0 to 8.0.

The particle of the invention has proven to be capable of the incorporation of a variety of membrane lipids and optionally membrane proteins, giving rise to nanoscale complexes that are soluble and stable in an aqueous environment. In particular, the particles according to the invention are nanoscale particles comprising a lipid binding polypeptide, membrane lipids and optionally a membrane protein. The membrane lipids and optionally the membrane protein are preferably obtained from the same cell and/or organelle membrane, in particular from the same plurality of a cell and/or an organelle membrane.

In a preferred embodiment, the particles of the invention generally are considered disc-shaped. In particular, they can have a Stokes radius (hydrodynamic radius) RS in the range of from 2 nm to 200 nm, in particular from 3 nm to 150 nm, preferably from 3 nm to 100 nm. The skilled person knows how to determine the Stokes radius. This is preferably done by analytical gel filtration (size exclusion chromatography), in comparison with standards of known Stokes radii. In particular, the particles can be subjected to a gel filtration step on e.g. a Superdex 200 HR10 30 gel filtration column and eluted with a suitable buffer at pH 7.5 and 0.5 ml/min at room temperature. Absorbance is monitored at 280 nm for protein. The column is calibrated using a mixture of protein standards of known Stokes radii such as e.g. thyroglobulin 669 kDa (RS=8.5 nm), ferritin 440 kDa (RS=6.1 nm) catalase 232 kDa (RS=4.6 nm), lactate dehydrogenase 140 kDa (RS=4.1 nm), bovine serum albumin 66 kDa (RS=3.55 nm) and horse heart cytochrome c 12.4 kDa (RS=1.8 nm). The standard proteins should span Rs values above and below that of the particle of interest. A calibration curve is generated by plotting the elution position vs Rs for the standard proteins. This generally gives an approximately linear plot, but otherwise, it is satisfactory to draw lines between the points and read the Rs of the protein of interest from its elution position on this standard curve.

In some embodiments, e.g. when a bulky hydrophobic agent, such as a membrane protein, or higher amounts of lipids are present in the particles, the Stokes radius will be larger than 3.2 nm, in particular at least 3.5 nm, at least 5.0 nm or at least 10.0 nm.

The particles of the invention may also be examined via transmission electron microscopy or, if the particles are large enough via negative-stain electron microscopy and single particle.

Structural analysis has indicated that in many cases, in the particles of the invention, the membrane lipids assemble into a discoidal bilayer-like structure of discrete size in the interior of the particle (see FIGS. 2a and 2b). The lipid binding polypeptide component generally defines the boundary of the discoidal bilayer and provides structure and stability to the particle. In most embodiments, the interior of the particle includes a hydrophobic region (e.g., comprised of lipid fatty acyl chains). In contrast to liposomes, particles of the invention preferably do not comprise a hydrophilic or aqueous core. The particles are preferably disc-shaped, having a flat, discoidal, roughly circular lipid bilayer circumscribed by amphipathic α-helices provided by two or more lipid binding polypeptides, which are associated with hydrophobic surfaces of the bilayer around the periphery of the disc. Illustrative examples of disc-shaped particles of the invention are schematically depicted in FIGS. 2a to 2f.

In some embodiments, the discoidal shape of the particles of the invention can be approximated by a cylinder with a ratio of the maximum height to the maximum diameter (major axis length) of at least 1.0: 1.1, in particular 1.0:1.5 or 1.0:2.0. The maximum height of the discoidal particle generally is at least 3.5 nm, in particular at least 5 nm, as determined by transmission electron microscopy or, if the particles are large enough, via negative-stain electron microscopy and single particle analysis. Preferably, the particle of the invention has a top, a bottom and a circumferential side surface, with the maximum diameter (major axis length) of the top and bottom surface being larger than the height of the circumferential side surface. In some embodiments of the particle of the invention, the lipid binding polypeptide is at least partially located to surround the circumferential side surface of the particle.

In some embodiments of the invention, the maximum diameter (major axis length) of the disc-shaped particle of the invention, as determined by transmission electron microscopy or, if the particles are large enough, via negative-stain electron microscopy and single particle analysis is from between 2 nm to 200 nm, in particular from 3 nm to 150 nm, preferably from 3 nm to 100 nm. In another embodiment, the maximum diameter (major axis length) of the disc-shaped particle is from 3 nm to 80 nm, in particular from 3 nm to 60 nm. Practical experiments have shown that particles having a maximum diameter (major axis length) of 3 nm to 20 nm are particularly easily obtainable with the method of the invention.

In preferred embodiments of the invention, the particles are defined by a substantially monodisperse population of disk structures, as assessed by the gel filtration elution profile on for example a HiLoad Superdex™ 200 16/60 GL column.

Generally, the predominant interaction between the lipid binding polypeptide and a lipid bilayer in a particle is through hydrophobic interactions between residues on the hydrophobic faces of amphipathic α-helices of the lipid binding polypeptide molecules and hydrophobic surfaces of lipids, for example, phospholipid fatty acyl chains, at the edge of the bilayer at the periphery of the bioactive agent delivery particle. An amphipathic α-helix of lipid binding polypeptide molecule includes both a hydrophobic surface in contact with a hydrophobic surface of the lipid bilayer at the periphery of the particle, and a hydrophilic surface facing the exterior of the particle and in contact with the aqueous environment when the particle is suspended in aqueous medium.

In some embodiments, the libraries and particles according to the invention are stable in aqueous solution and may be lyophilized for long term storage, followed by reconstitution in aqueous solution. "Stability" or "stable" as used herein means low to undetectable levels of particle fragmentation, low to undetectable levels of aggregation or quality deterioration during preparation, transportation, and storage of the particles.

In a preferred embodiment, the libraries and particles according to the invention are stable in aqueous solutions at a pH of from 2.0 to 10.0, in particular 6.0 to 10.0, preferably from 6.0 to 9.0, particularly preferred from 7.0 to 9.0, and most preferred from 7.0 to 8.0. In another embodiment, the libraries and particles according to the invention are stable in aqueous solutions at a temperature of from −210° C. to 80° C., in particular −210° C. to 40° C., −210° C. to 30° C. or −210° C. to 4° C. for at least 1 day, at least 2 days, at least 7 days, at least 2 weeks, at least 1 month, at least 6 months or at least 12 months, as determined, for example, by visual inspection (clear and precipitate-free solution) or analytical gel filtration (less than 50%, in particular from 1 to 40 fragmentation of the particles). Practical experiments have shown that the particles of the invention are also stable at temperatures from 4° C. to 40° C. in aqueous solutions at a pH of from 5.0 to 8.0 for at least 1 day, at least 2 days, at least 7 days, at least 2 weeks, at least 1 month or at least 3 months as determined, for example, by visual inspection (clear and precipitate-free solution) or analytical gel filtration (less than 50%, in particular from 1 to 40% fragmentation of the particles). The particles of the invention have also proven to be stable in aqueous solutions at a pH of from 5.0 to 8.0 and a temperature of from 40° C. to 75° C. for at least 10 minutes, as determined, for example, by visual inspection (clear and precipitate-free solution) or analytical gel filtration (less than 50%, in particular from 1 and 40% fragmentation of the particles). In some embodiments, the particles may be lyophilized for long term storage, followed by reconstitution in aqueous solution. In some embodiments the particles of the invention are stable in lyophilized form at −210° C. to 80° C., in particular −210° C. to 40° C., −210° C. to 30° C. or −210° C. to 4° C. for at least 1 day, at least 2 days, at least 7 days, at least 2 weeks, at least 1 month, at least 6 months or at least 12 months, as determined, for example, by analytical gel filtration after reconstitution in an appropriate buffer at pH 7.5 (less than 50%, in particular less than 40% or from 1 to 40% fragmentation of the particles). "Fragmentation" as used herein means that in the gel filtration elution profile, the size of the peak (i.e. peak height) corresponding to the particle of the invention has decreased at the expense of the peak size of free non-lipid-bound SAPLIP and/or free lipids and/or aggregates, as compared to the peak size of the freshly prepared particle of the invention. Accordingly, a fragmentation of 40% for example means that the peak size (i.e. the height of the peak in the gel filtration elution profile) has decreased by 40% as compared to the peak size prior to storage (100%).

Practical experiments have shown that the particles of the invention are particularly stable also in aqueous solutions that are substantially free of detergents. Substantially free of detergents means that the aqueous solution comprises less than 0.001% (w/v) of detergent based on the total volume of the aqueous solution.

The lipid binding polypeptide used according to the invention, i.e. in the Salipro particles, is a saposin-like protein (SAPLIP) or a derivative or truncated form thereof. The term "saposin-like protein" (SAPLIP) as used herein is art-recognized and includes all members of the saposin-like protein (SAPLIP) family of lipid interacting proteins. The SAPLIP family is characterized by the saposin-fold, a conserved alpha-helical three-dimensional structure that is stabilized by highly conserved intramolecular disulphide bonds (Munford et al. (1995), Journal of Lipid Research, vol. 36, no. 8, 1653-1663 and Bruhn (2005), Biochem J 389 (15): 249-257). Examples of members of the saposin-like protein (SAPLIP) family according to the invention are described in Munford et al. (1995), Journal of Lipid Research, vol. 36, no. 8, 1653-1663 and Bruhn (2005), Biochem J 389 (15): 249-257, both of which disclosures are hereby incorporated by reference in their entirety.

In the ligand-free (i.e. detergent-free/lipid-free), "closed" state, the SAPLIPs adopt a monomeric compact four-helix bundle-type structure, the saposin fold. This fold is exemplified by the structure of the closed apo form of human saposin A (Protein Data Bank (PDB) ID code: 2DOB, Ahn et al. (2006) Protein Sci. 15: 1849-1857) or the structures of saposin C (PDB ID code: 1M12; de Alba et al. (2003) Biochemistry 42, 14729-14740), NK-lysin (PDB ID code: 1NKL; Liepinsh et al. (1997) Nat. Struct. Biol. 4, 793-795), amoebapore A (PDB ID code: 1OF9) and granulysin (PDB ID code: 1L9L; Anderson et al. (2003) J. Mol. Biol. 325, 355-365) which are all nearly identical and easily superimposable.

SAPLIPs undergo a conformational change upon binding to ligands such as lipids or detergent molecules. In the ligand-bound "open" conformation, SAPLIPs adopt a V-shaped or boomerang-shaped conformation with exposed hydrophobic surfaces that contact the bound lipids. The open conformation is exemplified by the saposin A detergent disc structure of the prior art (PDB ID code: 4DDJ; Popovic et al., PNAS, Vol. 109, No. 8 (2012) 2908-2912) and the structure of saposin C bound to SDS detergent micelles (PDB ID code: 1SN6; Hawkins et al. (2005) J.Mol.Biol. 346: 1381-1392).

In the particles of the invention, the lipid binding polypeptide preferably is amphipathic, with one part of its structure more or less hydrophilic and facing the aqueous solvent and the other part more or less hydrophobic and facing the hydrophobic center of the particle which comprises the lipids. The lipid binding polypeptide is preferably characterized by amphipathic α-helices with more hydrophobic residues (such as A, C, F, G, I, L, M, V, W or Y) predominantly on one face of the helix and more polar or charged residues (such as D, E, N, Q, S, T, H, K, or R) on the other face of the helix.

The abbreviations for amino acid residues as used herein are as follows: A, Ala, alanine; V, Val, valine; L, Leu, leucine; I, lie, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gln, glutamine; D, Asp, aspartic acid; E, Glu, glutamic acid; K, Lys, lysine; R, Arg, arginine; and H, His, histidine.

Contrary to the apolipoprotein-derived nanodiscs of the prior art, the lipid binding polypeptide of the invention does not enclose the lipids in a double belt-like fashion but, rather, the particles of the invention are held together by a core comprising the lipids which is surrounded by two or more approximately V-shaped or boomerang-shaped lipid binding polypeptide arranged in a head-to-tail orientation with substantially no direct protein-protein contacts between the individual lipid binding polypeptides within a given particle of the invention (cf. FIGS. 2a to 2f). Without wanting to be bound to this theory, it is believed that this arrangement of lipid binding polypeptides and lipids in the particles of the invention provides the size flexibility that is observed when bulky hydrophobic agents or increasing amounts of lipids are incorporated into the inventive particles.

Whereas the ability to interact with lipids as well as the above described amphipathic nature and three-dimensional structure is highly conserved among SAPLIPs, they are highly diverse on the amino acid sequence level, with sequence identities below the usual threshold zone of 25-30% identity to define homology (cf. sequence comparison in FIGS. 4A and 4B of Bruhn (2005), Biochem J 389 (15): 249-257 reproduced in FIGS. 12a and 12b below, the sequences shown there form part of the disclosure of the present invention).

In the lipoprotein particles of the invention, the lipid binding polypeptide serves primarily as a structural protein, providing the scaffold for the structure of the lipoprotein particles of the invention, for example, a disc-like structure. For this reason, structural features, in particular the saposin-fold that is characteristic of the SAPLIPs, are more important for defining the lipid binding polypeptide of the invention as compared to mere sequence determinants.

Examples of SAPLIPs according to the invention are saposins A, B, C or D (for example from Homo sapiens [cf. SEQ ID NO. 1 to 4], Equus caballus, Bos taurus, Mus musculus, Oryctolagus cuniculus, Rattus norvegicus or Xenopus laevis); Surfactant protein B (for example from Homo sapiens, Canis familiaris, Mus musculus, Oryctolagus cuniculus, Ovis aries or Rattus norvegicus); Granulysin (for example from Homo sapiens; cf. SEQ ID NO. 5); NK-lysin (for example from Sus scrofa; cf. SEQ ID NO. 6); NK-lysin orthologues (for example from Equus caballus or Bos taurus); Amoebapores (for example from Entamoeba histolytica); Amoebapore orthologues (for example from Entamoeba dispar or Entamoeba invadens); Amoebapore-like protein (for example from Fasciola hepatica); Naegleriapores (for example from Naegleria fowleri); Clornorin (for example from Clonorchis sinensis); Prosaposin (for example from Homo sapiens, Equus caballus, Bos taurus, Mus musculus, Oryctolagus cuniculus, Rattus norvegicus or Xenopus laevis) and MSAP (for example from Homo sapiens).

The sequences of specific SAPLIPs used according to the invention are given in FIGS. 4A and 4B of Bruhn (2005), Biochem J 389 (15): 249-257, which FIG. and sequences specified therein form part of the disclosure of the present invention and are therefore identically reproduced in FIGS. 12a and 12b below. The sequences of particular SAPLIPs used according to the invention are given in the sequence listing as follows: SEQ ID NO. 1 Saposin A [Homo sapiens]; SEQ ID NO. 2 Saposin B [Homo sapiens]; SEQ ID NO. 3 Saposin C [Homo sapiens]; SEQ ID NO. 4 Saposin D [Homo sapiens]; SEQ ID NO. 5 Granulysin [Homo sapiens]; SEQ ID NO. 6 NK-lysin [Sus scrofa].

A SAPLIP used according to the invention may also be a polypeptide comprising the saposin-fold as part of a multi-domain protein. This is for example the case in acid sphingomyelinase (from Homo sapiens, Caenorhabditis elegans, Ciona intestinalis, Anopheles, Drosophila, Mus musculus or Rattus norvegicus); GDSL (Gly-Asp-Ser-Leu) lipase such as acyloxy hydrolase (from Homo sapiens or Rattus norvegicus); Countin (from Dictyostelium discoideum); J3-crystallin (from Tripedalia cystophora) and Plant aspartic proteases (from Viridiplantae). A further SAPLIP used according to the invention can be bacteriocin AS-48. Bacteriocin AS-48 displays antimicrobial activity, is also able to bind lipids and possesses the same fold as the remaining SAPLIP family members but is devoid of any disulphide bridges.

Whereas, in the following, the invention is described in more detail for saposin A or a derivative or truncated from thereof as lipid binding polypeptide, and whereas saposin A or a derivative or truncated from thereof as lipid binding polypeptide is a preferred embodiment, the invention shall not be limited thereby. Rather, the invention explicitly extends to the entire family of saposin-like proteins (SAPLIPs) as lipid binding polypeptides of the invention. Due to the high degree of structural and functional conservation among SAPLIPs, the features and advantages of certain embodiments of the invention with saposin A as lipid binding polypeptide are expected to also apply to other embodiments using other SAPLIPs or derivatives or truncated forms thereof as lipid binding polypeptide of the invention.

According to a preferred embodiment, the SAPLIP is saposin A, B, C or D, in particular a saposin selected from (Homo sapiens, Equus caballus, Bos taurus, Mus musculus, Oryctolagus cuniculus, Rattus norvegicus or Xenopus laevis) saposin A, saposin B, saposin C or saposin D. In one embodiment, the SAPLIP is (Homo sapiens, Equus caballus, Bos taurus, Mus musculus, Oryctolagus cuniculus, Rattus norvegicus or Xenopus laevis) saposin A, saposin B or saposin D.

Saposin C is special among the saposins in that it is capable of inducing membrane fusion, a feature which is not exhibited by the other saposins. The membrane fusion activity may not always be desirable. According to a particular embodiment of the invention the lipid binding polypeptide is a saposin-like protein (SAPLIP) or a derivative or truncated form thereof, provided that the SAPLIP is not saposin C or provided that the SAPLIP is not saposin C or a derivative or truncated form thereof.

In one embodiment, the SAPLIP is of human origin (i.e. a Homo sapiens SAPLIP).

In a preferred embodiment, the SAPLIP is saposin A, preferably (Homo sapiens, Equus caballus, Bos taurus, Mus musculus, Oryctolagus cuniculus, Rattus norvegicus or Xenopus laevis) saposin A, and particularly preferred human saposin A, the amino acid sequence of which is given as SEQ ID NO. 1. Saposin A is a known protein. Its expression, purification and crystallization as LDAO-detergent complex is for example, described in PNAS, Vol. 109, No. 8 (2012) 2908-2912 (Popovic et al.).

According to one embodiment of the invention, the lipid binding polypeptide comprises the full length sequence of a SAPLIP. In another embodiment, the lipid binding polypeptide is a derivative of a SAPLIP, in particular a polypeptide comprising an amino acid sequence with at least 20, 30, 40, 50 or 60%, preferably at least 75% identity to the full length sequence of the respective SAPLIP. In particular, the lipid binding polypeptide can comprise a sequence having an identity with the full length sequence of a SAPLIP of at least 80%, 85%, 90% or 95%.

The term "sequence identity" as used herein refers to a degree of identity between proteins that can be calculated by optimal alignment of the sequences using a scoring matrix such as the Blosum62 matrix described in Henikoff S. and Henikoff J G., P. N. A. S. USA 1992, 89: 10915-10919. Calculation of the percentage identity and optimal alignment of two sequences using the Blosum62 similarity matrix and the algorithm of Needleman and Wunsch (J. Mol. Biol. 1970, 48: 443-453) can be performed using the GAP program of the Genetics Computer Group (GCG, Madison, Wis., USA) using the default parameters of the program.

As a comparison for amino acid alignments the EMBL-online tool "EMBOSS Stretcher" (http://www.ebi.ac.uk/Tools/psa/emboss stretcher/) is used, using the programs default settings.

In another embodiment, the derivative of a SAPLIP is a polypeptide comprising a sequence having one or more amino acid deletions, additions, insertions and/or substitutions in the amino acid sequence of the respective SAPLIP. For example, the SAPLIP derivative can be a polypeptide comprising a sequence of a particular SAPLIP in which 1 to 40, preferably 1 to 30, and in particular 1 to 20 or 1 to 15 amino acids have been deleted, added, inserted and/or substituted.

The term "deletion" as used herein refers to the removal of 1, 2, 3, 4, 5 or more amino acid residues from the respective starting sequence.

The term "insertion" or "addition" as used herein refers to the insertion or addition of 1, 2, 3, 4, 5 or more amino acid residues to the respective starting sequence. The term "substitution" as used herein refers to the exchange of an amino acid residue located at a certain position for a different one.

According to another embodiment of the invention, the lipid binding polypeptide is a derivative of saposin A that comprises one or more fragments of SEQ ID NO. 1. Preferred fragments correspond to the helices a1, a2, a3 and a4 of saposin A, wherein helix a1 is formed by the following continuous stretch of amino acids: "SLPCDICKDVVTAAGDMLK"; helix a2 is formed by the following continuous stretch of amino acids: "ATEEEILVYLEKTCDWL"; helix a3 is formed by the following continuous stretch of amino acids: "PNMSASCKEIVDSYLPVILDIIKGEMS"; and helix a4 is formed by the following continuous stretch of amino acids: "PGEVCSAL". According to a particular embodiment of the invention, the derivative of saposin A is a polypeptide comprising a sequence selected from helices a1, a2, a3, a4 of saposin A and combinations thereof, in particular wherein the polypeptide comprises the sequences of helices a1, a2 and a3 of saposin A. The fragments of saposin A, such as its helices a1, a2, a3, a4, may have one or more amino acid deletions, additions, insertions and/or substitutions in the amino acid sequence.

When a derivative or truncated form of saposin A is used as lipid binding polypeptide according to the invention, said derivative or truncated form should be amphipathic, form at least one alpha helix, and be capable of self-assembling together with solubilized lipids into lipoprotein particles when employed in the preparation process according to the invention which is described in detail below. As used herein, the term "amphipathic" refers to polypeptides or molecules having both hydrophilic and hydrophobic regions.

Preferably, if a derivative of a SAPLIP is used, the six cysteine residues corresponding to the six cysteines in the SAPLIP founding member saposin A should be present. It is referred in this respect to the positions of the cysteines in the sequence comparison in FIGS. 4A and 4B of Bruhn (2005), Biochem J 389 (15): 249-257, which FIG. are hereby specifically incorporated by reference.

The lipid binding polypeptide according to the invention may also include one or more non-natural amino acids; amino acid analogs, or a peptidomimetic structure, in which the peptide bond is replaced by a structure more resistant to metabolic degradation.

Step a) of the Process of the Invention

In step a) of the process according to the invention, crude membrane vesicles obtained from a cell and/or an organelle membrane are provided. Crude membrane vesicles are always a mixture of different crude membrane vesicles. Usually, the crude membrane vesicles are obtained not from a single cell, but a plurality of a certain cell type and/or cell organelle. For example, certain eukaryotic, prokaryotic or archaeal cells may be used for obtaining the crude membrane vesicles. The term "plurality" as used herein means at least two or more cells. It is also possible to use a mixture of different eukaryotic, prokaryotic or archaeal cells for preparing the crude membrane vesicles. However, preferably, the crude membrane vesicles are obtained from one type of cell or organelle. In another embodiment, the crude membrane vesicles are obtained from a single (synonymous with singular) cell. In this embodiment, the process can be carried out on a single-cell level.

The term "crude" as used herein means that the membrane vesicles are obtained from crude membrane fractions, i.e. not further purified or extracted. The crude membrane thus still contains both membrane proteins and membrane lipids from the original cell or organelle membrane it was obtained from. This stands in direct contrast to the prior art processes that primarily use isolated and/or purified proteins or lipids. Crude membrane fractions can be obtained by separating the insoluble from the soluble components after cell or organelle disruption or lysis. The insoluble fraction is one form of crude membrane fraction that can be used according to the invention.

The term "vesicle" is a term of art to the skilled person. Typically, a vesicle is a small circular structure essentially consisting of aqueous fluid enclosed by a closed, spherical lipid bilayer. Crude membrane vesicles, however, are typically very divers and heterogeneous in size and content. They can either be specifically prepared or can form spontaneously upon cell/organelle disruption or lysis. The vesicles provided in step a) of the process are obtained from a cell or an organelle membrane. Therefore, the vesicles typically comprise cell or an organelle membrane, in particular a mixture of membrane lipids and optionally a membrane protein from the cell or plurality of cells used.

The vesicles provided in step a) a plurality of different vesicles, i.e. a mixture. The vesicles can differ in structure, size and/or composition. The structure of the vesicles can be unilamellar or multilamellar. The composition of the vesicles depends on the cell or organelle membrane from which they are obtained from and the method used for preparation, if any.

Whereas particular methods for obtaining vesicles from crude membranes known to the skilled person can be employed, e.g. sonication, the inventors have observed that often sufficient amounts of crude membrane vesicles self-assemble upon rupture or lysis of the naturally occurring cell or organelle membranes during disruption or lysis and preparation of the crude membrane fraction.

The membrane used in the process according to the invention is selected from cell membrane and organelle membrane. The "membrane", "organelle membrane" or "cell membrane" refers to any membranes comprising a layer of lipids. Preferably, the membrane is a lipid bilayer. Sometimes the term "membrane" is used herein interchangeably for "cell membrane" and/or "organelle membrane".

Basically, the cell membrane is a biological membrane that separates the interior of cells from the outside environment. The complex structure and the plurality of components comprised in cell membrane, such as membrane lipids and membrane proteins, are also described in detail in Alberts et al., "The Cell", 4th edition, Macmillian Magazines Ltd, 2002 on pages 583 to 614 and in Campbell et al., "Biologie", 6th edition, Spektrum Verlag, 2003 on pages 163 to 177. The cell membrane or organelle membrane used for the provision of crude membrane vesicles in step a) in the process according to the invention typically comprises a heterogenic mixture of different lipids and membrane proteins. Thus, the composition of the vesicles provided in step a) can differ in the mixture of membrane lipids and membrane proteins and typically depends on the particular membrane they were obtained from.

The term "lipid" or "membrane lipid" as used herein is art-recognized and refers to a naturalsubstance of biological origin that is soluble or partially soluble in organic solvents or which partitions into a hydrophobic environment when present in aqueous phase. Sometimes "lipid" and "membrane lipid" are used herein interchangeably. The term "lipid" or "membrane lipid" as used herein is not meant as a synthetic or single type of lipid molecule in the particle of the invention. In fact, it is meant as a plurality of at least two different kinds of lipid molecules that are present in the cell or organelle membrane. The lipids incorporated in the Salipro particles of the invention are membrane lipids that naturally occur in the cell or organelle membrane. Therefore, the particle of the invention typically comprises a mixture of membrane lipids that naturally occurs in the cell or organelle membrane from which they are obtained. In one embodiment the particles obtained according to the invention comprise at least 3, 5, 10 or 20 different lipids. Typically, these membrane lipids form a bilayer in which the membrane proteins are embedded. An exception is given for some archaeal membranes that can be used in the process according to the invention as some archaea comprise a monolayer. The structure of the cell membrane of archaea is described in more detail below.

The cell membrane or organelle membrane basically comprises as membrane lipids three classes of amphipathic lipids: phospholipids, glycolipids, and sterols. The amount of each depends upon the type of cell, cell membrane or organelle membrane. Phospholipids possess a polar part that dissolves in water (the phosphate "head"), and a hydrophobic non-polar part that does not ("the lipid tail"). These parts are connected by a glycerol moiety. In water phospholipids can build a cluster with the heads facing the water and the tails facing away from it. The fatty chains in phospholipids and glycolipids usually contain an even number of carbon atoms, typically between 16 and 20. The 16- and 18-carbon fatty acids are the most common. Fatty acids may be saturated or unsaturated. The configuration of the double bonds are typically in the so called cis-configuration. Cis- and trans-isomerism is a term used in organic chemistry to refer to the stereoisomerism engendered in the relative orientation of functional groups within a molecule according to Cahn-Ingold-Prelog (CIP; Cahn, R. S. & Ingold, C. K.; Prelog, V., "Specification of Molecular Chirality". Angewandte Chemie International Edition, 5 (4), p.385-415, 1966). Typical fatty acids present in the cell membrane are also described in Alberts et al., "The Cell", 4th edition, Macmillian Magazines Ltd, 2002 on pages 61 and 62. Further examples of the membrane lipids are phospholipids, such as phosphatidylcholine, such as POPC (1-palmitoyl-2-oleoyl-sn-glycero-3-phosphocholine), phosphatidylethanolamine, and phosphatidylserine, such as POPS (1-palmitoyl-2-oleoyl-sn-glycero-3-phospho-L-serine) phosphatidylinositol, and sphingomyelin.

Glycolipids are lipids with a carbohydrate attached thereto by a glycosidic bond. The carbohydrates are typically found on the outer surface of eukaryotic cell membranes. They extend from the phospholipid bilayer into the aqueous environment outside the cell. Examples of glycolipids are glyceroglycolipids, galactolipids, sulfolipids, glycosphingolipids, glucocerebrosides, sulfatides, gangliosides, globosides, glycophosphosphingolipids and glycophosphatidylinositols.

Sterols are a subgroup of steroids. Sterols as part of the membrane typically occur in eukaryotic membranes such as plants, animals, and fungi. Examples of sterols are cholesterol, campesterol, sitosterol, stigmasterol and ergosterol.

According to a preferred embodiment, the membrane lipids are lipid bilayer forming lipids and/or biocompatible lipids. The term "biocompatible" as used herein denotes being biologically compatible by not producing a toxic, injurious, or immunological response in living tissue.

As used herein, "bilayer-forming lipid" refers to a lipid that is capable of forming a lipid bilayer with a hydrophobic interior and a hydrophilic exterior. Any bilayer-forming lipid that is capable of associating with a SAPLIP or a derivative or truncated form thereof to assemble into a particle structure may be used in accordance with the invention. Bilayer-forming lipids include, but are not limited to, phospholipids, sphingolipids, glycolipids, alkylphospholipids, ether lipids, and plasmalogens. One type of bilayer-forming lipid may be used or a mixture of two or more types. Particles may also include lipids that are not bilayer-forming lipids. Such lipids include, but are not limited to, cholesterol, cardiolipin, phosphatidylethanolamine (this lipid may form bilayers under certain circumstances), oxysterols, plant sterols, ergosterol, sitosterol, cationic lipids, cerebrosides, sphingosine, ceramide, diacylglycerol, monoacylglycerol, triacylglycerol, gangliosides, ether lipids, alkylphospholipids, plasmalogens, prostaglandins, and lysophospholipids.

The membrane lipids comprised in the Salipro particle of the invention can be a mixture of the membrane lipids listed above, but are not limited thereto. Typically, the membrane lipids comprised in the particles according to the invention comprise at least phospholipids, glycolipids, cholesterol and mixtures thereof. According to a preferred embodiment, the membrane lipids are eukaryotic lipids and/or prokaryotic lipids, in particular such that are typically present in any one of the membranes present in a eukaryotic or prokaryotic cell. Preferred lipids, for example, are phospholipids, glycosphingolipids, sterols, phosphatidylcholine, phosphatidylserine (PS), 2-oleoyl-1-palmitoyl-sn-glycero-3-phosphocholine (POPC), 2-oleoyl-1-palmitoyl-sn-glycero-3-glycerol (POPG), 2-oleoyl-1-palmitoyl-sn-glycero-3-phosphoethanolamine (POPE), diacylglycerol, cholesterol, sphingomyelin, galactosylceramide, gangliosides, phosphatidylinositoles and sulphogalactoceramides or combinations thereof.

In another embodiment, the membrane lipids comprise phospholipids. Examples of suitable phospholipids include, but are not limited to, DMPC, DMPG, POPC, dipalmitoylphosphatidylcholine (DPPC), dipalmitoylphosphatidylserine (DPPS), cardiolipin, dipalmitoylphosphatidylglycerol (DPPG), distearoylphosphatidylglycerol (DSPG), egg yolk phosphatidylcholine (egg PC), soy bean phosphatidylcholine, phosphatidylinositol, phosphatidic acid, sphingomyelin, and cationic phospholipids. The membrane lipids in the particle according to invention are typically a heterogenic mixture of lipids that occur in the cell or organelle membrane. But it is also possible to further include a lipid in the particle of the invention that may be a modified lipid including one or more bound functional moieties, such as a targeting moiety or a bioactive moiety.

A targeting moiety can, for example, serve to target the particles of the invention to a particular cell or tissue type, or to an infectious agent. It may also serve to purify, study or identify the particles. In some embodiments, the particle includes a targeting moiety attached to a lipid binding polypeptide or a lipid component or a membrane protein component.

The targeting moiety can for example have receptor recognition properties so that the particles can be targeted to a specific cell surface receptor. For example, the particles of the invention may be targeted to a particular cell type known to harbor a particular type of infectious agent, for example by modifying the lipid binding polypeptide component of the particles to render it capable of interacting with a receptor on the surface of the cell type being targeted. In one embodiment, the targeting moiety is selected from the group consisting of natural or synthetic ligands, antibodies and antibody fragments or other biomolecules suitable for targeting purposes.

A bioactive moiety can be selected, for example, from a drug, a cytotoxic agent, an enzyme, a label, a fluorophore, a contrast agent and a radiolabel.

Additional lipids may also be included in the Salipro particle of the invention besides the membrane lipids of the cell or organelle membrane. These can be selected from naturally occurring lipids, synthetic lipids, modified lipids, fats, waxes, sterols, fat-soluble vitamins, monoglycerides, diglycerides, triglycerides, phospholipids, fatty acids, glycerolipids, glycerophospholipids, sphingolipids, saccharolipids, polyketides, sterol lipids and prenol lipids or combinations thereof.

The Salipro particles according to the invention can lack membrane proteins, i.e. be essentially only comprised of lipid binding polypeptide and membrane lipids from the crude membrane vesicles ("empty" Salipro particles). Preferably, they, however also comprise a membrane protein ("filled" Salipro particles). Membrane proteins are proteins that naturally are embedded in a membrane or, optionally, also such that are only associated with a membrane. Membrane proteins can exhibit a variety of functions. For example, membrane receptor proteins relay signals between the cell's internal and external environments and transport proteins move molecules and ions across the membrane. Membrane proteins can also act as enzymes that may have many activities, such as oxidoreductase, transferase or hydrolase activity. Membrane proteins may also, for example, be cell adhesion molecules.

According to one embodiment, the Salipro particles of the invention either comprise no membrane protein or a number of from 1 to 10, or 1 to 5 membrane proteins per particle. The library can also be defined according to one embodiment as comprising particles in which the average number of membrane proteins per particle is from 1 to 10, or 1 to 5.

The membrane proteins in the particles of the invention, for example, can be selected from a membrane protein, an integral transmembrane protein, an integral monotopic membrane protein, a peripheral membrane protein, an amphitropic protein in a lipid-bound state, a lipid-anchored protein and a chimeric protein with a fused hydrophobic and/or transmembrane domain.

Integral membrane proteins are membrane proteins which are permanently bound to the lipid bilayer and usually require a detergent or apolar solvent to become displaced form the membrane. Transmembrane proteins are integral membrane proteins that span across the membrane at least once. Examples of transmembrane proteins that can be incorporated into the particles of the invention are G-protein coupled receptors (GPCRs), porters such as uniporters, symporter or antiporters, channels such as ion channels or enzymes.

Integral monotopic membrane proteins are permanently attached to the membrane only from one side and do not span across the membrane. This class includes membrane proteins that are tethered to the membrane via alpha-helical transmembrane anchors. Examples include cytochrome P450 oxidases and glycophorin A.

Peripheral membrane proteins are only temporarily or indirectly associated with the lipid bilayer or integral membrane proteins incorporated therein. Peripheral membrane proteins usually dissociate from membranes following treatment with a polar reagent with an elevated pH or high salt concentrations. Examples of peripheral membrane proteins include phospholipase A2 or C, lipoxygenases and cytochrome c.

Lipid-anchored proteins are bound to the lipid bilayer via lipidated, in particular prenylated or GPI-anchored amino acid residues. Examples include bacterial lipoproteins, G proteins and certain kinases.

Amphitropic proteins are proteins that exist in at least two conformational states, a lipid free, water-soluble state and a lipid bound state. Upon association with lipids, amphitropic proteins undergo a conformational change allowing them to become reversibly or irreversibly membrane-associated. Examples of amphitropic proteins are pore-forming toxins and antibacterial peptides.

The vesicles provided in step a) can be obtained from a cell and/or a cell organelle. The term "a" used herein means "one" or "a plurality of" a certain object. For example, "a cell" means a certain cell or a plurality of the certain cell. Typically, a plurality of a cell and/or a cell organelle is used in the process according to the invention. The process according to the invention is not limited to the employment of a cell and/or a cell organelle. It is also possible to use a mixture of different cells or organelles for the preparation of the membrane vesicles.

In a special embodiment of the invention, the crude membrane vesicles of step a) are prepared by at least one, two, three or all the following steps:
a.1) provision of a cell and/or a cell organelle;
a.2) lysing or disrupting the cell and/or the cell organelle;
a.3) obtaining a crude membrane fraction; and
a.4) preparing crude membrane vesicles from the crude membrane fraction obtained in step a.3).

In step a.1) a cell and/or a cell organelle is provided. The term "cell" as used herein is understood as typically used in biology. A cell is the basic structural, functional, and biological unit of all known living organisms. A cell is the smallest unit of life that can replicate independently. "Cell" as used herein also includes eukaryotes, prokaryotes and archaea. "Cell" as used herein does not include a virus.

Cells comprise cytoplasm enclosed by a cell membrane, which comprises biomolecules such as proteins and lipids as explained above. Organisms can be classified as unicellular, i.e. consisting of a single cell such as prokaryotes, or multicellular, such as eukaryotes, e.g. animals, plants or fungi.

The cell from which the membrane used in the process according to the invention is obtained is not limited to a certain cell type. The cell can be a naturally occurring, a transfected, genetically engineered or a disease cell, e.g. a cancer cell. It was found that various cell types are suitable for the process according to the invention.

Preferably the cell is a archaeal, a eukaryotic or a prokaryotic cell. Preferred cell organelles are eukaryotic organelles.

The cell membranes of archaea, eukaryotes and prokaryotes each comprise membrane lipids and optionally membrane proteins as described above. However, the skilled person in the art knows that archaea, eukaryotic and prokaryotic cells differ from each other. The structure, function and differences of archaea, eukaryotic or prokaryotic cells are described in various standard text books such as Alberts et al., "The Cell", 4th edition, Macmillian Magazines Ltd, 2002 or Campbell et al., "Biologie", 6th edition, Spektrum Verlag, 2003.

A eukaryote is any cell or organism whose cells contain a nucleus and optionally further organelles enclosed by membranes. In one embodiment the membrane used in the process according to the invention is membrane from a eukaryote, e.g. the cell membrane and/or membrane stemming from a cell organelle. Examples for organelles are the Golgi apparatus, mitochondria, peroxisomes, endoplasmic reticulum, chloroplasts, nucleus and the like.

Examples of eukaryotes are plants, animals, and fungi such as yeast and molds. Preferred eukaryotic cells that can be used in the process according to the invention are selected from the group consisting of mammalian cells, in particular animal and human cells, insect cells, avian cells, fungal cells such as yeast cells, plant cells, and mixtures thereof. The term mammalian cells especially also includes animal and human cells which are kept in culture medium.

A prokaryote is a single-celled organism that lacks a nucleus. Prokaryotic cells are simpler and smaller than eukaryotic cells, and lack membrane organelles. Examples of prokaryotes are bacteria. Exemplary bacterial phyla are acidobacteria, actinobacteria, aquificae, armatimonadetes, bacteroidetes, caldiserica, chlamydiae, chlorobi, chloroflexi, chrysiogenetes, cyanobacteria, deferribacteres, deinococcus-thermus, dictyoglomi, elusimicrobia, fibrobacteres, firmicutes, fusobacteria, gemmatimonadetes, lentisphaerae, nitrospira, planctobacteria, proteobacteria, spirochaetae, synergistetes, tenericutes, thermodesulfobacteria, thermotogae and verrucomicrobia. Preferred prokaryotic cells that can be used in the process according to the invention are bacteria, in particular pathogenic bacteria, and mixtures thereof.

Archaea are related only distantly to prokaryotes and eukaryotes. A detailed overview is given, e.g. in De Rosa et al., "Structure, Biosynthesis, and Physicochemical Properties of Archaebacterial Lipids", MICROBIOLOGICAL REVIEWS, p. 70-80 Vol. 50, No. 1, 1986, or Albers et al., "The archaeal cell envelope", Nature Reviews Microbiology, 9, p. 414-426, 2011.

De Rosa et al. report that archaeal membranes comprise molecules that differ strongly from those of prokaryotes and eukaryotes. Prokaryotes and eukaryotes comprise membranes comprising mainly glycerol-ester lipids, whereas archaea comprise membranes comprising glycerol-ether lipids. Ether bonds are chemically more resistant than ester bonds. This stability might help archaea to survive extreme temperatures and very acidic or alkaline environments. Prokaryotes and eukaryotes may comprise ether lipids, but in contrast to archaea, these lipids are only a minor or no component of the membrane.

In addition, archaeal lipids are based upon a isoprenoid sidechain. Isoprenoid side chains are long chains containing 20, 25 or up to 40 carbon atoms with optionally multiple side-branches. They may also comprise cyclopropane or cyclohexane rings. This is in contrast to the fatty acids found in other organisms' membranes as described above. Although isoprenoids play an important role in the biochemistry of many organisms, only the archaea use them to make phospholipids. In some archaea, the lipid bilayer may be replaced by a monolayer.

Examples of archaea are methanogenic archaea, halobacteria and thermo-acidophilic archaea. Preferred archaea that can be used in the process according to the invention are extremophile archaea and mixtures of different extremophile archaea.

Using a virus that may comprise lipids or proteins from its host is not part of the invention, which is only directed to cell or organelle membrane-derived vesicles and particles. The term cell or organelle excludes viruses. The virus structure and components of the virus' membrane, if applicable, differ from eukaryotic, prokaryotic and archaea membranes. This is reported in more detail in, e.g. Lorizate et al., "Comparative lipidomics analysis of HIV-1 particles and their producer cell membrane in different cell lines", Cellular Microbiology, 15(2), p. 292-304, 2013 and Bragger et al., "The HIV lipidome: A raft with an unusual composition", PNAS, Vol. 103, No. 8, p. 2641-2646, 2006.

Lorizate et al. report that various studies indicated that the HIV-1 membrane differs from the producer cell plasma membranes suggesting virus budding from pre-existing subdomains or virus-mediated induction of a specialized budding membrane. The lipid analysis of plasma membranes and HIV-1 purified from two different cell lines revealed a significantly different lipid composition of the viral membrane compared with the host cell plasma membrane, independent of the cell type investigated. Virus particles were significantly enriched in phosphatidylserine, sphingomyelin, hexosylceramide and saturated phosphatidylcholine species when compared with the host cell plasma membrane of the producer cells. They showed reduced levels of unsaturated phosphatidylcholine species, phosphatidylethanolamine and phosphatidylinositol. Cell type-specific differences in the lipid composition of HIV-1 and donor plasma membranes were observed for plasmalogen-phosphatidylethanolamine and phosphatidylglycerol, which were strongly enriched only in HIV-1 derived from MT-4 cells. MT-4 cell-derived HIV-1 also contained dihydrosphingomyelin. Taken together, these data reported by Lorizate et al. support that HIV-1 selects a specific lipid environment for its morphogenesis and is not identical or similar to its hosts' cell membranes. Usually, the particles and libraries of the invention described herein do not contain viral proteins and/or viral membranes.

The cell in step a.1) can, e.g. be provided as a purified or non-purified cell fraction, such as in a cell suspension or growth media. The cell can also be provided in form of a cell culture, which cells are typically grown under controlled conditions, such as inside or outside of their natural environment. The skilled person knows that cells in a cell line are very similar, but that they are often not identical. However, the provision of a plurality of a cell obtained from a cell line also falls under the meaning of provision of a cell in step a.1). The cell or organelle recited in step a.1) can also be part of a larger, more complex group of cells and/or organelles used in that step.

In step a.1), the cell can also be provided in form of a crude biological sample such as tissue, organs or any other biological cell containing sample. The person skilled in the art can, however, also isolate a cell, a cell organelle or a plurality thereof from a sample such as a cell culture, tissue, tissue suspension or any other biological sample.

There are several approaches that can be used to separate different cell types from a mixed cell suspension. One exploits differences in physical properties. Large cells can for example be separated from small cells and dense cells from light cells by centrifugation.

Another approach is based on the tendency of some cell types to adhere strongly to glass or plastic, which allows them to be separated from cells that adhere less strongly. A further cell-separation technique uses an antibody coupled to a dye, label or tag that targets specific cells. The labeled cells can then be separated from the unlabeled ones, e.g., by FACS or other methods. Certain cells can also be obtained by carefully dissecting them from tissue slices. Microdissection techniques allow selected cells to be isolated from tissue slices. This method can, for example, involve a laser beam to excise a region of interest and eject it into a container, and it permits the isolation of even a single cell from a tissue sample.

Various techniques for the separation, purification or isolation of cells, organelles can be employed in the method of the invention. The methods described above in respect of cells are also suitable for obtaining a cell organelle.

In step a.2) at least a part of the cell and/or cell organelle is disrupted or lysed. The term "lysing" or "disrupting" refers to breaking down at least a part of the cell or organelle membrane. The cells and/or cell organelles can be lysed/disrupted by chemical or mechanical means. Depending upon the lysing/disruption technique used, either all, some or only a part of the membranes are lysed/disrupted. For example, if only the cell membrane is lysed/disrupted then gradient centrifugation can be used to collect certain organelles.

Lysis or disruption may be effected by enzymes, chemical agents or mechanically. Mechanical lysis of a cell or organelle membranes, as by repeated freezing and thawing, sonification, such as ultrasonification, pressure, rupture by low osmotic pressure shock, or filtration may also be referred to as lysis. The unprocessed solution immediately after lysis, but before any further extraction or purification step is referred to as a crude lysate. From the crude lysate, one can isolate the crude membrane fraction comprising the membranes present in the lysate. Typically this can be achieved by separating the insoluble fraction (crude membrane fraction) from the soluble fraction of the lysate, e.g., by centrifugation. In a preferred embodiment of the invention the crude membrane vesicles are obtained from the crude membrane fraction without any other vesicle generation, purification or extraction step.

In step a.3) a crude membrane fraction is obtained. In one embodiment of the invention, both, steps a.2) and a.3) can be performed simultaneously. This can be accomplished by, e.g. by lysing the cell and/or cell organelle and thereby already providing crude membrane vesicles.

In step a.4), the crude membrane vesicles are obtained from the crude membrane fraction after step a.3) or after steps a.2) and a.3). The crude membrane vesicles can be obtained by partially solubilizing or agitating the crude membrane fraction in a solvent, buffer, detergent or mixtures thereof. Examples of suitable aqueous solvents are water, such as deionized, demineralized or sterilized water, saline solutions, such a solution of NaCl, and solutions comprising phosphate, acetate, glycine, ammonium, calcium, magnesium, potassium salts or mixtures thereof. Preferred buffers are physiologically tolerable buffers. Examples of suitable buffers are for instance phosphate buffer, ACES, PIPES, imidazole/HCl, BES, MOPS, HEPES, TES, TRIS, HEPPS or TRICIN.

In another embodiment of the invention, steps a.2), a.3) and/or a.4) are performed simultaneously. By lysing the cell and/or cell organelle a crude membrane fraction is present in the lysate. The inventors have observed that often enough crude membrane vesicles form spontaneously to be used in the process of the invention.

Step b) of the Process of the Invention

In step b) of the method of the invention the mixture obtained after step a), i.e. the crude membrane vesicles, is contacted with the lipid binding polypeptide in a liquid environment. Step b) of the method of the invention can also be formulated as "contacting the crude membrane vesicles with the lipid binding polypeptide in a liquid environment". The crude membrane vesicles are those obtained in step a) and/or a.4).

The lipid binding polypeptide and the lipids can be in the forms as described above.

In certain embodiments, the liquid environment is an aqueous solution. The aqueous solvent can be a buffered solution. The liquid environment in step b) can have a pH of from 2.0 to 10.0, in particular 6.0 to 10.0, preferably from 6.0 to 9.0, particularly preferred from 7.0 to 9.0, and most preferred from 7.0 to 8.0. The liquid environment in step b) can also optionally comprise a detergent.

The duration of steps b) and/or c) is very much dependent on the particular experimental setup, in particular the types of lipids and or membrane proteins present in the Salipro particles and the temperatures at which these steps are conducted. Good results were generally achieved, when steps b) and c) each independently of one another last for a duration of from 10 s to 24 h, from 10 s to 2 h, from 10 s to 30 min and from 10 s to 15 min. Preferably, steps b) and/or c) are carried out at a temperature from 10 to 60° C., preferably from 15 to 42° C., particularly preferred from 30 to 40° C. When prolonging the incubation time, it is, however also possible to work at low temperatures, e.g. 2 to 10° C. Temperatures indicated are that of the liquid environment that the steps are carried out in.

In a particular embodiment of the process according to the invention, the crude membrane vesicles are contacted with a detergent in step a), b) and/or c).

The term "detergent" as used herein is art-recognized and not comprised in the definition of "lipids" or "membrane lipids" as used herein.

While many lipids have a similarly amphiphilic general structure as compared to detergents, i.e. a polar hydrophilic head group and a nonpolar hydrophobic tail-lipids differ from detergents in the shape of the monomers, in the type of aggregates formed in solution, and in the concentration range required for aggregation. Lipids are generally substantially cylindrical in structure; the volume occupied by the hydrophobic tail is similar to the volume occupied by the polar head group. Detergents monomers are generally more cone-shaped; the volume occupied by the hydrophobic tail is smaller than the volume occupied by the polar head group. Detergents tend to aggregate into spherical or ellipsoid micelles that are water soluble without forming bilayer structures in the absence of lipids (cf. handbook "Detergents and their uses in membrane protein science" from Anatrace, www.anatrace.com). Detergents that may be employed in the process according to the invention can be anionic, cationic, non-ionic, zwitterionic and mixtures thereof.

Detergents as used herein are preferably selected from the group consisting of alkylbenzenesulfonates or bile acids, cationic detergents and non-ionic or zwitterionic detergents such as lauryl-dimethyl amine-oxides (LDAO), Fos-Cholines, CHAPS/CHAPSO, alkyl glycosides such as short, medium or longer chain alkyl maltosides, in particular n-Dodecyl β-D-maltoside, glucosides, maltose-neopentyl glycol (MNG) amphiphiles, amphiphilic polymers (amphipols), macrocycle or cyclic oligomers based on a hydroxyalkylation product of a phenol and an aldehyde (Calixarene), and mixtures thereof.

Typical anionic detergents are alkylbenzenesulfonates. The alkylbenzene portion of these anions is lipophilic and the sulfonate is hydrophilic. Anionic detergents can, e.g. comprise branched alkyl groups or linear alkyl groups. Examples of suitable anionic detergents are bile acids, such as deoxycholic acid (DOC), alkylbenzenesulfonates, such as branched sodium dodecylbenzenesulfonate, linear sodium dodecylbenzenesulfonate, and mixtures thereof.

Cationic detergents are similar to the anionic ones, with a hydrophobic component, but, instead of the anionic sulfonate group, the cationic surfactants have quaternary ammonium as the polar end. The ammonium center is positively charged.

Non-ionic detergents are characterized by their uncharged, hydrophilic headgroups. Typical non-ionic detergents are, e.g. based on polyoxyethylene or a glycoside. Common examples of the former include Tween, Triton, and the Brij series. These materials are also known as ethoxylates or PEG-lyates and their metabolites, nonylphenol. Glycosides have a sugar as their uncharged hydrophilic headgroup. Examples include octyl thioglucoside and maltosides. HEGA and MEGA series detergents are similar, possessing a sugar alcohol as headgroup. Examples of suitable non-ionic detergents that can be used in the process according to the invention are alkyl glycosides such as short, medium or longer chain alkyl maltosides, such as n-Dodecyl-β-maltoside (DDM), Decanoyl-N-hydroxyethylglucamide (HEGA), n-Decanoyl-N-methyl-D-glucamide (MEGA), and mixtures thereof.

Zwitterionic detergents possess a netto zero charge arising from the presence of equal numbers of adverse charged chemical groups, i.e. in the summ the number of negative charges and positive charges are equal so that the overall charge is netto zero. Examples include Fos-Cholines, CHAPS/CHAPSO, lauryl-dimethyl amine-oxides (LDAO) and mixtures thereof.

Practical experiments have shown that it is advantageous to use detergents with short- to medium-chain hydrophobic tails. This is particularly true if a membrane protein is incorporated as hydrophobic agent. "Short chain hydrophobic tails" as used herein means C2 to C9, such as for example in n-Nonyl-b-maltoside (NM); "medium chain hydrophobic tails" as used herein means C10 to C15, such as for example in n-Decyl-β-maltoside (DM) or n-Dodecyl-β-maltoside (DDM). In one embodiment, the detergent used for purification and/or solubilization of the hydrophobic agent has from 2 to 12 carbon atoms in its hydrophobic tail, preferable from 2 to 10 and most preferred from 2 to 9 carbon atoms in its hydrophobic tail.

The membrane vesicles in any one of steps a) or a.1), a.2. a.3) and/or a.4) can be in a detergent-solubilized state. Practical experiments have shown that a wide variety of detergents can be used to further solubilize the crude membrane vesicles for being employed in the process according to the invention. For example, the process according to the invention works very well with crude membrane vesicles present in solutions comprising 0.01 to 5.0%, in particular 0.1 to 1.0% alkyl glycosides such as short or longer chain alkyl maltosides and glucosides. However, depending on the type of membrane or crude membrane vesicles employed, other suitable detergents may be used as well. The ability of a given detergent to solubilize a given membrane or crude membrane vesicles can easily be inspected visually by the formation of a clear solution devoid of aggregates, precipitates or phase separation. Without being bound to theory, it seems that the addition of a detergent loosens the membrane structure and aids the particle self-assembly, i.e. the incorporation of crude membrane components into the Salipro particles.

In one embodiment of the invention, the detergent used to solubilize the mixture in step b) is not carried over in substantial amounts into the finished particles of the invention. In particular, the amount of detergent in the particles obtainable by the process according to the invention can be low to undetectable. In one embodiment, the particle of the invention does not comprise any substantial amounts of detergent, in particular less than 0.1 wt.-%, preferably less than 0.01 wt.-%, particularly preferred less than 0.001 wt.-% detergent based on the weight of the particle. The amount of detergent present in the particles can be determined, for example, by mass spectrometry.

Practical experiments have shown that the lipid binding polypeptides of the invention generally do not require detergents or other solvents during purification, storage or handling. Optionally, however, also the lipid binding polypeptide used in step b) can be in a detergent-solubilized state.

In some embodiments, the molar ratio of lipid binding polypeptide to membrane vesicles in step b) is at least 1:1, preferably at least 2:1 or at least 5:1, particularly preferred at least 10:1. In another embodiment, the molar ratio of lipid binding polypeptide to membrane vesicles in step b) is from 1:1 and 1.000.000:1, in particular from 1:1 and 100.000:1 or from 10.000:1 and 500:1.

In some embodiments, the weight ratio of lipid binding polypeptide to membrane vesicles in step b) is at least 1:1, preferably at least 2:1 or at least 5:1, particularly preferred at least 10:1. In another embodiment, the weight ratio of lipid binding polypeptide to membrane vesicles in step b) is from 1:1 and 1.000.000:1, in particular from 1:1 and 100.000:1 or from 10.000:1 and 500:1.

In one embodiment, the lipid binding polypeptide in step b) is in molar excess compared to the crude membrane vesicles. In another embodiment, the amount of lipid binding polypeptide in step b) is in excess compared to the crude membrane vesicles (each time wt-% based on the total weight of the mixture in step b).

For most membrane proteins to be incorporated into the particles of the invention, optimal results are achieved if the molar ratio of lipids to membrane proteins in step b) is from 100.000:1 to 1000:1, in particular from 100:1 to 1:1.

In one embodiment of the process according to the invention, the molar ratio of lipid binding polypeptide to membrane vesicles in step b) is at least 1:1, in particular at least 3:3, preferably at least 5:1 or 10:1. In another embodiment of the process according to the invention, the weight ratio of lipid binding polypeptide to membrane vesicles in step b) is at least 1:1, in particular at least 3:3, preferably at least 5:1 or 10:1.

In another embodiment steps a) and b) are performed simultaneously. In a further embodiment at least one step of steps a.1) to a.4) is performed simultaneously with step b). In this embodiment it is also possible to perform at least two steps of steps a.1) to a.4) and step b) simultaneously. In a special embodiment all steps ad) to a.4) and step b) are performed simultaneously. In a preferred embodiment, steps a.3), a.4) and b) are performed simultaneously In a further embodiment of the invention the process further comprises between steps a) and b) the step of
b.1) contacting the crude membrane vesicles with a detergent in a liquid environment.

The detergent can be as defined above.

In case step b.1) is performed, the mixture obtained after step b.1), i.e. the mixture of crude membrane vesicles and detergent, is contacted with the lipid binding polypeptide in step c). Optionally, there can also be a step b.2) between step b.1) and step b), wherein the mixture of crude membrane vesicles and detergent obtained in step b.1) is purified before being contacted with the lipid binding polypeptide in step b). Such purification is described in more detail below and can involve, e.g., the removal of detergent, in particular excess or substantially all detergent, or the removal of non-vesicle components. An example of such as purification is the removal of debris and/or protein aggregates by ultracentrifugation. In case step b.2) is performed, the mixture obtained after step b.2), i.e. the purified mixture of crude membrane vesicles, is contacted with the lipid binding polypeptide in step c).

Such a purification step can also occur as step c.1) between steps b) and c), wherein the mixture obtained after steps a) and b) is purified.

Steps a), b) and/or c) can be carried out in the presence of a detergent. Preferably, the detergent is selected from the detergents described above. The detergent may be added in a suitable form such as in liquid, solid or in a liquid-solid state.

In an embodiment, the mixture obtained after step a), a.4), b) or b.1) is optionally purified. Such purification steps, are, for example, described as steps b.2) and c.1) above.

Suitable purification methods are chromatographic methods, in particular size-exclusion chromatography, ultracentrifugation, dialysis, contacting with detergent-binding biobeads, use of concentrators, affinity chromatography, magnetic beads and/or membrane/filters to remove unbound/non-incorporated lipids and/or hydrophobic compounds. The skilled person is able to select a suitable purification method depending on the purification goal to be achieved.

Step c) of the Process of the Invention

In step c) of the process according to the invention, the self-assembly of the particles takes place. Step c) does not need to be a separate step, it can also occur simultaneously with step b). Usually the self-assembly of the particles occurs directly upon contacting the crude membrane with the lipid binding polypeptide of the invention. Step c) is usually performed in a liquid environment, which can be the same or different from the liquid environment used in step b).

The self-assembly of the particles in step b) can also be called a fragmentation of the crude membranes or the crude membrane vesicles into the Salipro particles of the invention. This fragmentation or self-assembly is triggered upon contact with the lipid binding polypeptide of the invention.

Preferably, step c) of the invention comprises allowing the self-assembly of the particles at a pH of from 2.0 to 10.0, in particular 6.0 to 10.0, preferably from 6.0 to 9.0, particularly preferred from 7.0 to 9.0, and most preferred from 7.0 to 8.0. These pH ranges can also apply to step b) described above, independently of the pH applied in step c). The pH ranges described herein allow the components brought into contact with each other in step b) to particularly efficiently self-assemble into the particles of the invention in step c).

Contrary to the expectation that Salipro particles should be best assembled at or close to the saposins' natural pH optimum of 4.75, it was found that libraries with Salipro particles showing improved properties and an extended application spectrum can also be obtained when a more neutral or basic pH is maintained during the self-assembly of the particles. Surprisingly, it was found that at a pH of from 5.0 to 10 (in particular from 6.0 to 10, more preferably from 6.0 to 8.5 and most preferably from 7.0 to 8.0) and in the presence of crude membrane vesicles, purified saposin-like protein or a derivative or truncated form thereof can self-assemble into stable lipoprotein particles without the need of a laborious upstream purification processes regarding either the lipid or membrane protein component to be incorporated.

Step c) of the process according to the invention may comprise or consist of diluting the mixture obtained in step b) with a liquid, in particular one that contains no or less amounts of detergent than the mixture obtained in step b). Practical experiments have shown that such a dilution step further induces and facilitates the self-assembly of the particles of the invention. Without wanting to be bound by this theory, it is believed that such a dilution step effectively removes impurities, solvent and/or detergent molecules from the hydrophobic surfaces of the lipid binding polypeptide and the crude membrane vesicles, thereby further facilitating the particle self-assembly process according to the invention via enhanced hydrophobic interactions of the components.

Whereas the particle self-assembly in step c) may take place in exactly the same composition as prepared in step b), step c) may also comprise or consist of an addition of organic solvent, a detergent removal, a purification or a dilution step. Step c) can, for example, be a gel filtration step. In that case the mixture obtained after step b) is in step c) both purified and diluted with the gel filtration buffer used. In certain embodiments, the mixture obtained in step b) is subjected to a gel filtration step, whereby the gel filtration buffer or other solution is a liquid that contains no detergent or less amounts of detergent than the mixture obtained in step b).

According to a particular embodiment, the steps described above, in particular steps a), b) and/or c) and/or one of their respectively described sub-steps a.1) to a.4, b.1) to b.2) and/or c.1) are performed at a temperature of from 4° C. to 85° C., in particular from 20° C. to 70° C., particularly preferred at 30° C. to 70° C. A temperature of between 30° C. to 40° C. is sufficient for most applications. However, by the methods taught herein, the skilled person can determine the optimal incubation temperature with regards to the temperature stability of the membranes, compounds, lipids and proteins used.

In a further embodiment the process comprises in step c) or as a subsequent step d) the purification of the particles by at least partial removal of free membrane lipids, free membrane proteins, free lipid binding polypeptide, unsoluble or aggregated matter and/or detergent, wherein, optionally, the purification is performed by chromatography, in particular size-exclusion chromatography; ultracentrifugation; dialysis; contacting with detergent-binding biobeads; use of concentrators; affinity purification methods including but not limited to chromatography, magnetic beads, immunopurification and/or membrane/filters to remove unbound/non-incorporated lipids and/or hydrophobic compounds.

The processes described above yield libraries of salipro particles according to the invention. These reflect and contain the entire or a part of, preferably a substantial part of, the membrane proteome and lipidome of the crude membrane vesicles that were used as starting material in step a), i.e. the membrane proteome and lipidome of the cell or organelle that these crude membrane vesicles were prepared from. The Salipro particle libraries are directly useful as such, e.g., in life sciences research, in systems biology, to study the membrane proteome and/or lipidome of a given cell or organelle, in drug development, in particular drug screening processes, in the development of antibodies, and various medical or cosmetic applications.

The libraries obtained by the method of the invention are, however, also particularly useful to serve as starting material from which a particular selection of or a particular type of Salipro particle can be purified from.

Accordingly, the invention also provides a process for preparing purified saposin lipoprotein particles comprising the steps of preparing a library according to the process as described above and the additional step of f) purifying at least one type of saposin lipoprotein particle from the library.

The purification of the at least one type of Salipro particle in step f) can be performed by any purification, extraction or separation method, preferably by those described herein.

The purification of the at least one type of saposin lipoprotein particle from the library can be performed by affinity purification including but not limited to affinity chromatography and/or immunopurification, in particular by using an antigen or tag on a membrane protein present in the particle to be purified. Additionally or alternatively, the purification can be performed by chromatography, in particular size-exclusion chromatography; ultracentrifugation; dialysis; contacting with detergent-binding biobeads; or use of concentrators.

Preferably, the purification of the at least one type of Salipro particle in step f) is performed by affinity purification such as affinity chromatography. Preferably, an antigen or tag (also called "affinity tag" herein) is present on a membrane protein or lipid present in the at least one Salipro particle to be purified. Preferably, the antigen or tag is present on a membrane protein in the at least one Salipro particle to be purified. The tag or antigen used for purification may, however, also be present on the lipid binding polypeptide in the Salipro particles. This way, the entire library is affinity purified in step f).

Preferably, a recognition entity is used in the affinity purification, wherein the recognition entity binds to the antigen or affinity tag present in the Salipro particle.

As known to the skilled person, affinity purification involves an antigen or affinity tag on the component (e.g. the Salipro particle) to be purified and a corresponding recognition entity (e.g., an antibody in case of an antigen, or a Ni-NTA entity in case of a His-tag) used to purify the component from a mixture. Basically, various antigen or affinity tag/recognition entity pairs known to the skilled person from protein affinity purification techniques can be used to purify the at least one type of Salipro particle according to the invention in step f).

Affinity tag/recognition entity pair interactions were developed to aid in protein purification and immobilization. Proteins may be modified at the genetic level with certain peptide sequences, known as affinity tags, that bind to known recognition entities. Affinity tags generally fall into three categories: a) peptide sequences that bind to small molecules; b) fusion proteins that bind to small molecules; and c) peptide tags or fusion proteins that bind to antibodies. An affinity tag may also be a small molecule that has a convenient binding partner. The affinity tag may be covalently attached to a target protein, peptide, or lipid present in the crude membrane vesicles used in step a) of the inventive method. In this way, affinity-tagged Salipro particles may be immobilized on, for example, a matrix or resin that bears a binding partner, or a recognition entity, for the affinity tag. For example, nitrilo tri-acetic acid, when complexed to $Ni^{2+}$ ($NTA-Ni^{2+}$), defines a recognition entity that binds proteins modified with a stretch of histidines, known as a histidine tag, defining an affinity tag.

"Affinity tag" is given its ordinary meaning in the art. An affinity tag is any biological or chemical material that can readily be attached to a target biological or chemical material. Affinity tags may be attached to a target biological or chemical molecule by any suitable method. For example, in some embodiments, the affinity tag may be attached to the target molecule using genetic methods. For example, the nucleic acid sequence coding the affinity tag may be inserted near a sequence that codes a biological molecule present in the crude membrane vesicles; the sequence may be positioned anywhere within the nucleic acid that enables the affinity tag to be expressed with the biological molecule, for example, within, adjacent to, or nearby. In other embodiments, the affinity tag may also be attached to the target biological or chemical molecule after the molecule has been produced (e.g., expressed or synthesized). As one example, an affinity tag such as biotin may be chemically coupled, for instance covalently, to a target protein or peptide to facilitate the binding of the target to streptavidin.

Affinity tags include, for example, metal binding tags such as histidine tags, GST (in glutathione/GST binding), streptavidin (in biotin/streptavidin binding). Other affinity tags include Myc or Max in a Myc/Max pair, or polyamino acids, such as polyhistidines. At various locations herein, specific affinity tags are described in connection with binding interactions. The molecule that the affinity tag interacts with (e.g. binds to), which may be a known biological or chemical binding partner, is the "recognition entity." It is to be understood that the invention involves, in any embodiment employing an affinity tag, a series of individual embodiments each involving selection of any of the affinity tags described herein.

A recognition entity may be any chemical or biological material that is able to bind to an affinity tag. A recognition entity may be, for example, a small molecule such as maltose (which binds to MBP, or maltose binding protein), glutathione, NTA/Ni2+, biotin (which may bind to streptavidin), or an antibody. An affinity tag/recognition entity interaction may facilitate attachment of the target molecule, for example, to another biological or chemical material, or to a substrate. Examples of affinity tag/recognition entity interactions include polyhistidine/NTA/Ni2+, glutathione S transferase/glutathione, maltose binding protein/maltose, streptavidin/biotin, biotin/streptavidin, antigen (or a fragment of an antigen)/antibody (or a fragment of an antibody), and the like.

Affinity tag or antigen/recognition entity pairs useful in step f) of the invention are, for example, an antibody/peptide interaction, an antibody/antigen interaction, a fragment of an antibody/antigen interaction, a nucleic acid/nucleic acid interaction, a protein/nucleic acid interaction, a peptide/peptide interaction, a protein/protein interaction, a small molecule/protein interaction, a glutathione/GST interaction, a maltose/maltose binding protein interaction, a carbohydrate/protein interaction, a carbohydrate derivative protein interaction, a peptide tag/metal ion-metal chelate interaction, a peptide/NTA-Ni interaction, epitope tag (e.g., V5-tag, Myc-tag, FLAG-tag, or HA-tag)/antibody interaction, a Protein A/antibody interaction, a Protein G/antibody interaction, a Protein L/antibody interaction, a fluorescent protein (e.g., GFP)/antibody interaction an Fc receptor/antibody interaction, a biotin/avidin interaction, a biotin/streptavidin interaction, a zinc finger/nucleic acid interaction, a small molecule/peptide interaction, a small molecule/target interaction, and a metal ion/chelating agent/polyamino acid interaction.

Any of the above mentioned affinity tags can be present on a membrane protein, lipid or the lipid binding polypeptide in the Salipro particle of the invention, in particular the type of Salipro particle that is to be purified in step f). Any of the above mentioned recognition entities can be used to purify the Salipro particle in step f).

In an embodiment of the invention the tag is a fluorescent tag. In particular, the Salipro particles or one type of Salipro particle present in the Salipro particle library obtained by the method of the invention can carry a fluorescent tag. In a preferred embodiment, a lipid, membrane protein or the lipid-binding polypeptide present in the Salipro particle carries the fluorescent tag. Such fluorescent tags are useful for detecting and following a particular membrane protein or a particular type (species) of Salipro particle during its generation (and optionally purification) in the methods of the invention. GFP and its variants are the most commonly used fluorescent tags. In addition, practical studies revealed that it is possible to tag specific membrane proteins in crude membranes or crude membrane vesicles, which are then used in step a) for the preparation of the library according to the invention. This tagging preferentially occurs on the genetic level, e.g., by genetically engineering or by inserting a vector carrying a tagged transgene into the cell or organelle that the crude membrane vesicles are obtained from.

Using the techniques described above, the invention provides a process for preparing a Salipro particle comprising a particular membrane protein of interest containing an antigen or an affinity tag.

This procedure is exemplarily described below for crude cell membranes containing a GFP-fusion of the membrane protein GLUT5, but the invention is not limited thereto. Briefly, a crude membrane fraction comprising crude membrane vesicles containing GFP-GLUT5 (step a) of the process according to the invention) were contacted (with or without detergent) with Saposin A in a liquid environment (step b) and partially already c) of the process according to the invention), followed by a removal of detergent-micelles using gel-filtration chromatography/size-exclusion chromatography in detergent-free buffer (step c) of the process according to the invention), thereby forcing the hydrophobic moieties of the initial mixture to self-assemble into Salipro nanoparticles. Given the complexity of the crude membrane used as starting material, this process yields a heterogeneous library of Salipro particles including a plethora of different membrane proteins. Some Salipro particles in the library will contain the fluorescently labeled GFP-GLUT5 membrane protein, other Salipro particles will contain other membrane proteins and some Salipro particles will be devoid of membrane proteins and only contain membrane lipids derived of the crude membrane, as indicated in FIG. 4b below.

The process according to the invention, in one embodiment, provides a library of Salipro particles wherein each Salipro particle essentially consists of at least one lipid binding polypeptide and components of the crude cell or the organelle membrane, in particular, wherein each Salipro particle essentially consists of the at least one lipid binding polypeptide and membrane lipids and, optionally, membrane proteins from the crude cell or the organelle membrane.

The term "essentially" used herein means that also traces of further components used in the process according to the invention can be present in the Salipro particles such as further components of the crude membranes or agents used in the process, such as detergents. That the Salipro particle essentially consists of the at least one lipid binding polypeptide and components of the membrane obtained from the cell or the organelle membrane shall, however, in particular mean that no further lipids and/or proteins are added. In particular, no further synthetic, purified and/or exogenous lipids and/or proteins are added in the process according to the invention.

In a preferred embodiment of the invention no additional lipids besides lipid components of the crude membrane vesicles are added in the process according to the invention. In a further preferred embodiment of the invention no additional membrane proteins besides protein components of the crude membrane vesicles are added in the process according to the invention.

The invention provides a library of saposin lipoprotein particles and/or a Salipro particle obtainable according any of the process described above.

The Salipro particles obtainable by the process according to the invention and included in the inventive Salipro particle libraries differ from the particles of the prior art in multiple features. For example, they comprise components of crude cell and organelle membranes. In particular, they comprise membrane proteins from cell and organelle membranes, in particular such that are still preserved in their native cell or organelle membrane lipid context. In a preferred embodiment, the inventive Salipro particles comprise as membrane protein component and lipid component only membrane lipids, and, optionally, membrane proteins from a or one specific type of cell or organelle membrane. In a particularly preferred embodiment, the inventive Salipro particles comprise as membrane protein component, if any, and as lipid component only membrane proteins and lipids from the same cell or organelle membrane.

In addition, the Salipro particles of the invention are characterized by their inherent size flexibility and ability to adapt to the respective size of the membrane component that is to be incorporated into the lipoprotein particles. This allows for a wide variety of membrane proteins, complexes thereof, membrane domains or membrane components to be incorporated into the Salipro particles of the library. The inventive libraries therefore are not only heterogeneous in respect to the content of each individual Salipro particle, but also in respect to the size of each individual Salipro particle. "Empty", i.e. lipid-only Salipro particles will be smaller than such that carry a given membrane protein, which again will be smaller than those carrying a multimeric membrane protein complex. By this size flexibility, the Salipro particle libraries allow capturing an unbiased array of a given cells or organelles membrane proteome and lipidome in its native context.

Usually, the particles in the Salipro particle libraries differ in their protein composition. They may also differ in their lipid composition, reflecting different lipid compositions of membrane domains in the cell or organelle membrane used as starting material. Advantageously, the library obtained according to invention can provide particles comprising parts or components of the membrane. Another advantage is that the natural environment of the membrane lipids and optionally the membrane protein is maintained in the Salipro particles of the invention.

The library of Salipro particles or the Salipro particle obtainable according to the methods of the invention are also provided for use in medicine, in particular for use in preventing, treating or lessening the severity of a disease or for use in a diagnostic method, a cosmetic treatment or for use as vaccination formulation.

For example, the Salipro particle of the invention can be included into a pharmaceutical composition for delivering one or more membrane proteins and/or lipids to an individual in need thereof, wherein the composition comprises particles of the invention as described above.

Besides the particles of the invention, the pharmaceutical composition can optionally comprise a (further) pharmaceutically acceptable vehicle, carrier or adjuvant. When the particles of the invention are for use in a pharmaceutical composition, the individual components of the particles and the pharmaceutical composition should be pharmaceutically acceptable. As used herein, the term "pharmaceutically acceptable" refers to components, compounds or agents that are, within the scope of sound medical judgment, suitable for use in contact with the tissues of humans and lower animals without undue toxicity, irritation, allergic response and the like, and are commensurate with a reasonable benefit/risk ratio.

In yet another aspect, the invention provides a method of treating an individual in need thereof, with a therapeutically effective amount of the pharmaceutical composition described above. A "therapeutically effective amount" of the pharmaceutical composition, as used herein, is that amount effective for treating or lessening the severity of the disease or condition to be treated. The term "individual", as used herein, means an animal, for example, a mammal, and more specifically a human.

The pharmaceutical compositions of this invention can be administered to humans and other animals orally, rectally, parenterally, intracisternally, intravaginally, intraperitoneally, topically (as by powders, ointments, or drops), buccally, as an aerosol, an oral or nasal spray, or the like, depending on the severity of the disease or condition being treated. In particular, the pharmaceutical composition can be formulated for enteral, parenteral and/or topical administration. It can be administered as a capsule, infusion or injection, a brushable or potable composition or as an aerosol. In some embodiments of the pharmaceutical composition of the invention, the particles of the invention are present in solid form, as a dispersion or in solution.

The particles of the invention are also useful for diagnostic and/or cosmetic applications. For example, Salipro particles comprising a detectable antigen or tag as described for example above, may be used as diagnostic agents and applied for diagnostic purposes. The antigen or tag may itself be comprised in or formed by a membrane protein present in Salipro particle, however they may also be attached to the lipid binding polypeptide or the lipid components of the particle. Examples of diagnostic and life science research tools according to the invention include particles with tagged incorporated membrane proteins, tagged lipid binding polypeptide, tagged lipids, incorporated fluorophores or contrast agents (for example for MR imaging). The tag can for example be a fluorescent tag.

In another aspect, the particles of the invention are useful as vaccination formulation, as carrier thereof or as drug delivery vehicle. Many pathogenic antigens that could be particularly potent in vaccinations are exposed on the surface and/or comprised in the outer cell membrane of eukaryotic or prokaryotic pathogens or disease cells (e.g. cancer cells) in a patient. These antigens can, e.g., be derived from pathogenic lipids, other hydrophobic biomolecules or membrane proteins. The term pathogen as used herein does not comprise viruses. With the particles of the invention, such antigens can effectively be incorporated into the particles which then can be used as antigen-presenting delivery vehicles in vaccination formulations. Along these lines, the particles of the invention are also useful to serve as antigen-presenting delivery vehicles for generating antibodies against lipids or membrane proteins in suitable host animals, preferably in mammals such as e.g. rabbits, goats, lamas, mice and primates.

The invention also provides in a further aspect the use of a library of Salipro particles of the invention or the Salipro particle of the invention as a tool for drug development, drug screening, drug discovery.

For example, a particular membrane protein drug target, such as a cell surface receptor or ion channel, may be incorporated into the particles of the invention and solubilized thereby in its native state. The particle can then be purified from the library as described above. Such particles can then be employed in assays to study the activity of the drug target membrane protein in its native lipid bilayer environment or used in drug screenings to identify new drugs.

Conversely, the entire Salipro particle library obtained from a particular cell or organelle that could be a disease target can be used for drug screening purposes to identify new molecular drug targets, such as membrane proteins or lipids present in the membrane of the target cell or organelle.

The library and the methods described herein can also be used as a tool for membrane protein purification, membrane protein expression, for membrane and/or membrane protein research, in particular lipidomics and proteomics, preferably for the isolation, identification and/or study of membranes and/or membrane proteins or creation of a lipidome or proteome library or database.

Moreover, the particles of the invention either purified or as part of the entire library may also be fixed to a solid support making them useful for applications such as Surface Plasmon Resonance (SPR) or biosensor applications.

The particles of the invention are generally useful for rendering otherwise insoluble membrane proteins and membrane domains or components soluble in aqueous solutions in their native membrane bilayer microenvironment. Hence, the invention provides a wide variety of new applications in membrane protein research. For example, the particles of the invention allow studying membrane proteins incorporated in the particles of the invention by methods such as nuclear magnetic resonance (NMR), X-ray crystallography, electron microscopy (EM), mass spectrometry, isothermal titration calorimetry (ITC), differential light scattering, small-angle X-ray scattering (SAXS) and the like.

The libraries of the invention are particularly useful for research in the field of systems biology, especially lipidomics and membrane proteomics. The libraries of the invention may be suitable for capturing and solubilizing the lipidome or proteome of a cell or cell organelle. Typical analytical techniques in lipidomics and proteomics are technologies such as mass spectrometry (MS), nuclear magnetic resonance (NMR) spectroscopy, fluorescence spectroscopy, and computational methods. Applying these methods or techniques to the Salipro particles of the invention will allow further elucidation of the role of natural lipids and membrane proteins in many metabolic diseases such as, for example, cancer, autoimmune diseases, obesity, atherosclerosis, stroke, hypertension and diabetes.

The advantage of the incorporation of crude membrane into the particles of the library of the invention is that they then represent snapshots of the microdomains and components of the actual membrane from which they were obtained. In contrast thereto, typical Saposin lipid comprising particles known from the prior art are composed of synthetic or a heterogenous mixture of purified lipids and optionally proteins, wherein the lipids usually originate from a completely different source than the membrane proteins present in the particles.

BRIEF DESCRIPTION OF THE FIGURES

The invention will hereinafter be described with reference to the Figures, which depict certain embodiments of the invention. The invention, however, is as defined in the claims and generally described herein. It should not be limited to the embodiments shown for illustrative purposes in the Figures below.

FIG. 1a is a schematic illustration of the shape and molecular organization of the Apolipoprotein A-1 containing nanosdisc particles of the prior art (e.g. EP 1 596 828 B1 discussed above).

In FIGS. 2a) and 2b) a Salipro particle 1c comprising cell or organelle membrane lipids is shown; depicted in a) as side view and in b) as top view.

Figure 12A:
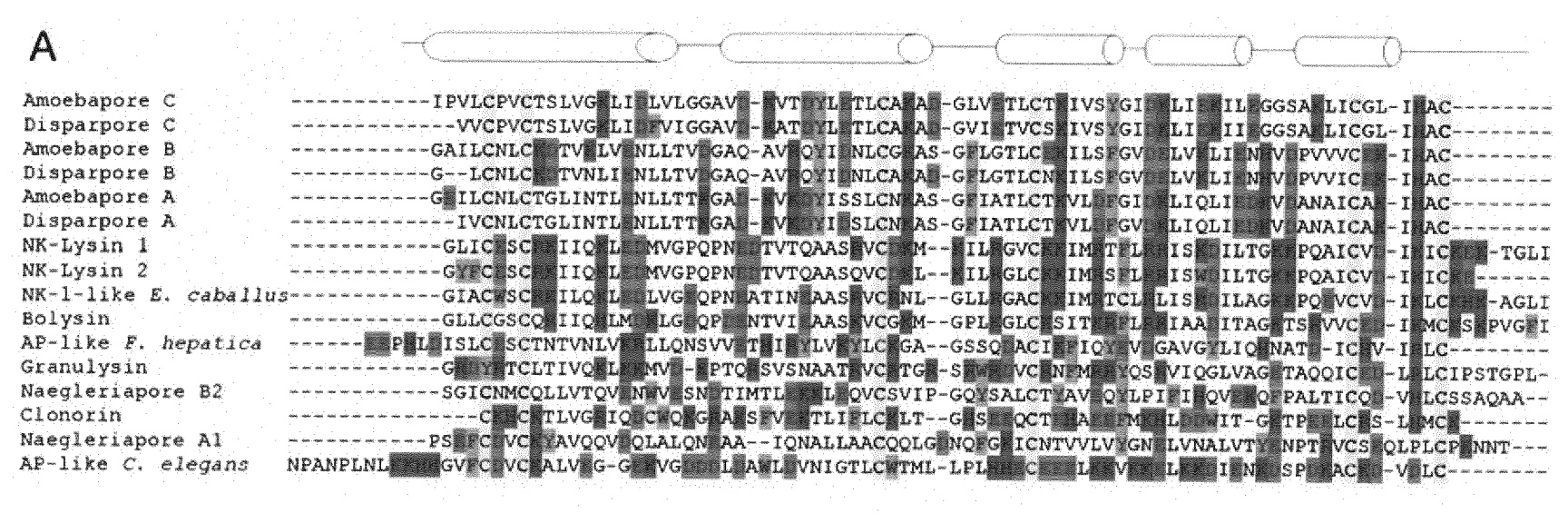

FIGS. 12a) and 12b) are identical reproductions of FIGS. 4A and 4B, respectively, of Bruhn (2005), Biochem J 389 (15): 249-257, which sequences form part of the disclosure of the present invention.

FIG. 1a) depicts a prior art Apolipoprotein A-1 containing nanosdisc particle A (see, e.g., EP 1 596 828 B1 discussed above) comprising lipids B and Apolipoprotein A-1 as lipid binding polypeptide C. Contrary to the apolipoprotein-derived nanodiscs of the prior art, the lipid binding polypeptide of the present invention does not enclose the lipids in a double belt-like fashion (cf. C in FIG. 1a) but, rather, the particles of the invention are held together by a core comprising the membrane lipids which is surrounded by two or more approximately V-shaped or boomerang-shaped lipid binding polypeptides arranged in a head-to-tail orientation with substantially no direct protein-protein contacts between the individual lipid binding polypeptides within a given particle of the invention (cf. FIGS. 2a to 2f).

FIG. 1b is a schematic illustration of the process used to create Saposin lipoprotein particles G of the prior art (e.g. WO 2014/095576 A1) discussed above. Here, a SAPLIP D is incubated with purified lipids E and detergent F solubilized, purified membrane protein 4a to form a particle G. Lipids E are purified and derived of a different source than membrane protein 4a. Membrane protein 4a is not present in a membrane or a vesicle, but is in an artificial, detergent-solubilized stated (see lipids E and detergent molecules F binding to the hydrophobic surfaces of the membrane protein 4a in FIG. 1b, middle). Thus in the particle G, the membrane protein 4a is not embedded in its natural membrane environment, but rather in a mixture of artificial or exogenous lipids E and, possibly also detergent F.

FIGS. 2a) to 2f) are schematic illustrations of Salipro particles obtained according to certain embodiments of the invention. The particles 1a, 1b, and 1c comprise a plurality of different membrane lipids 3 and optionally a membrane protein, 4a, 4b. Both the membrane lipids 3 and the membrane proteins 4a and 4b stem from the same cell or organelle membrane that was used to prepare the particles. The lipids 3 are not uniform or homogeneous, but differ from each other as this is the typical case in a biological membrane. In addition, depending on the source from which the crude membrane vesicles 5 are obtained (see FIGS. 3a and 3b), the composition of the membrane will vary, and, accordingly, also the mixture of lipids 3 and optionally present membrane proteins in the Salipro particles. In a further embodiment, which is not shown, the Salipro particles may also comprise further components that are typically present in a cell or organelle membrane.

Figure 1A:
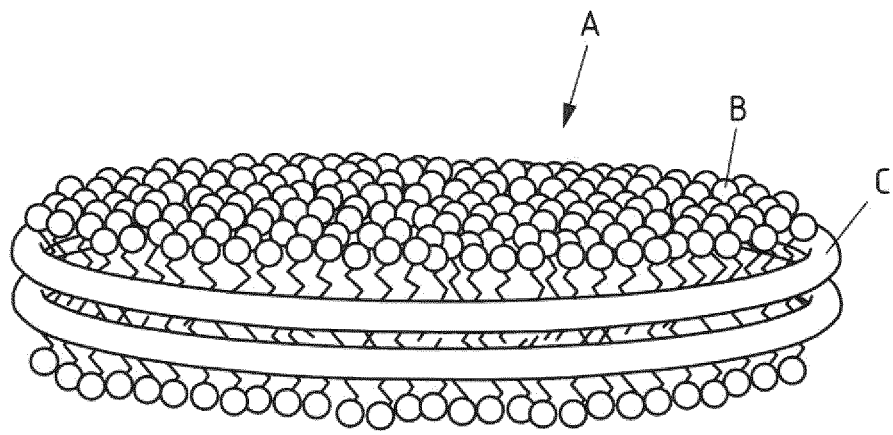
FIGS. 1a) and 1b) depict prior art lipoprotein particles.
Figure 1B:
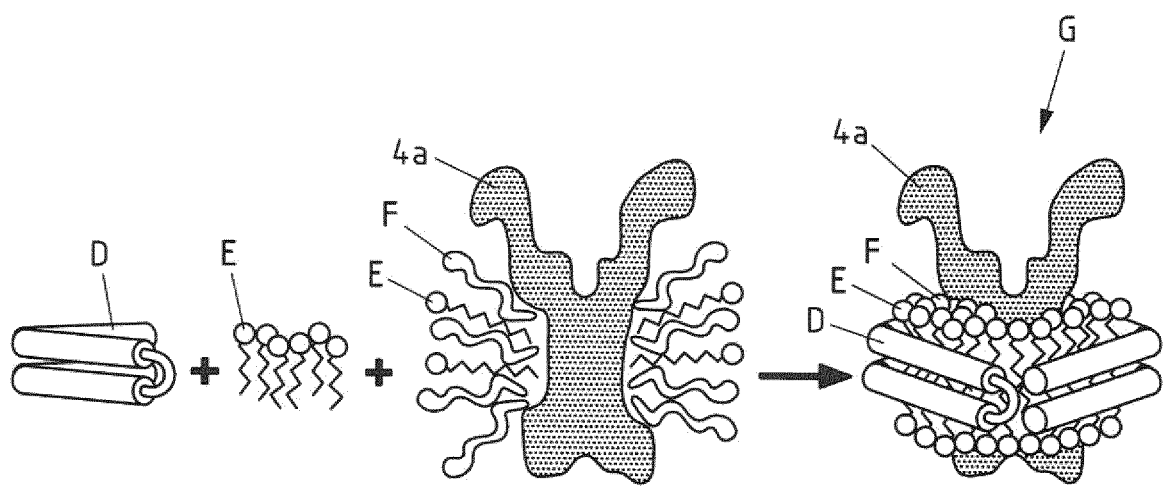
FIG. 1b is a schematic illustration of the process used to create Saposin lipoprotein particles of the prior art (e.g. WO 2014/095576 A1) discussed above.

The particles 1a to 1c are not drawn to scale. Depending on the size of the membrane protein 4a, 4b incorporated in the particles 1a or 1b, the lipid-only particle 1c can be substantially different in size compared to the other particles 1a, 1b. Also particles 1a and 1b can differ in size, lipid and optimally membrane protein composition. Also particles 1c can differ in size, e.g., if parts of a lipid rafts are entirely incorporated into a Salipro particle. Note that the Salipro particles of the invention are flexible in size. For example, particle 1b harboring an oligomeric membrane protein is larger than and contains more Saposin subunits 2 as compared to particle 1a which contains a monomeric membrane protein.

Figure 2A:
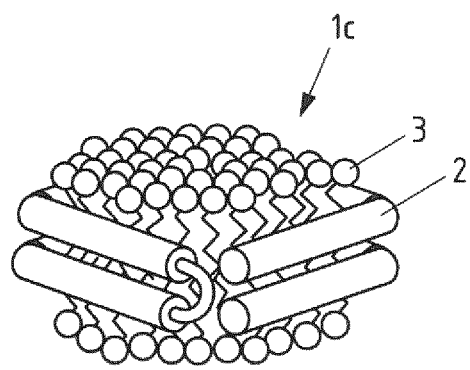
FIGS. 2a) to 2f) are schematic illustrations of Salipro particles according to the invention.
Figure 2B:
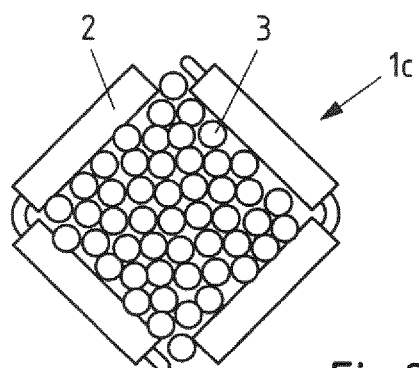
Figure 2C:
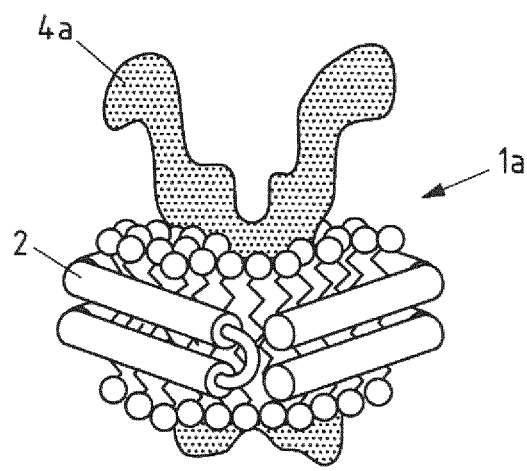
In FIGS. 2c) and 2d) a Salipro particle 1a comprising cell or organelle membrane lipids and a membrane protein 4a is shown; depicted in c) as side view and in d) as top view.
Figure 2D:
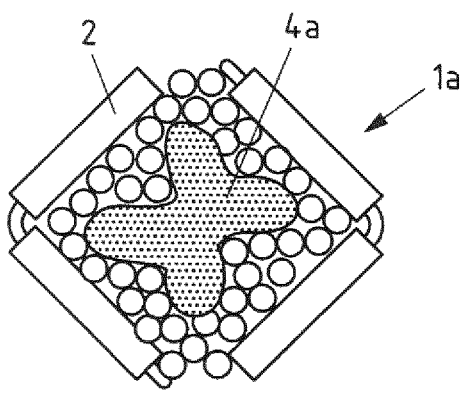

FIGS. 2a) and 2b) depict—in simplified schematic form—Salipro particle 1c comprising as lipid binding polypeptide 2 a SAPLIP and cell or organelle membrane lipids 3; it is depicted in a) as side view and in b) as top view. FIGS.

2c) and 2d) depict Salipro particle 1a, which differs from 1c in that it additionally comprises membrane protein 4a; it is depicted in c) as side view and in d) as top view. The membrane protein 4a can be an integral transmembrane protein in monomeric form. However, it can also be in an oligomeric state as depicted in FIG. 2e) or 2f) or a peripheral membrane protein, an amphitropic protein in a lipid-bound state, a lipid-anchored protein or a chimeric protein with a fused hydrophobic and/or transmembrane domain, all of which may be in a monomeric or oligomeric state.

Figure 2E:
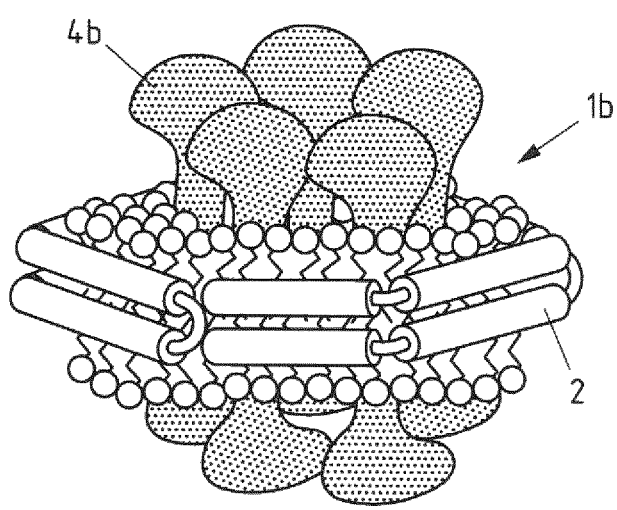
In FIGS. 2e) and 2f) a Salipro particle 1b comprising cell or organelle membrane lipids and an oligomeric membrane protein 4b is shown; depicted in e) as side view and in f) as top view.
Figure 2F:
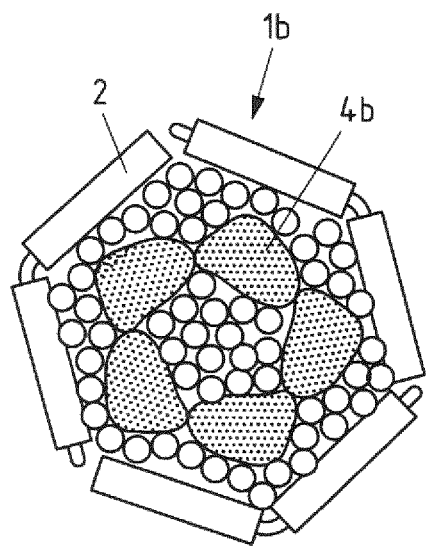

FIGS. 2e) and 2f) depict Salipro particle 1b, which differs from 1c in that it additionally comprises oligomeric membrane protein 4b. it is depicted in e) as side view and in f) as top view. The particle 1b shows flexibility in size and adapts to the size of the oligomeric membrane protein 4b incorporated therein. In the embodiment depicted in FIG. 2e) or 2f), the particle 1b comprises three SAPLIP molecules 2 per particle which are arranged in a head-to-tail fashion. The hydrodynamic radius of a particle comprising three SAPLIP molecules is in the range of from 5 to 20 nm, depending on the hydrophobic agent incorporated therein.

Figure 3A:
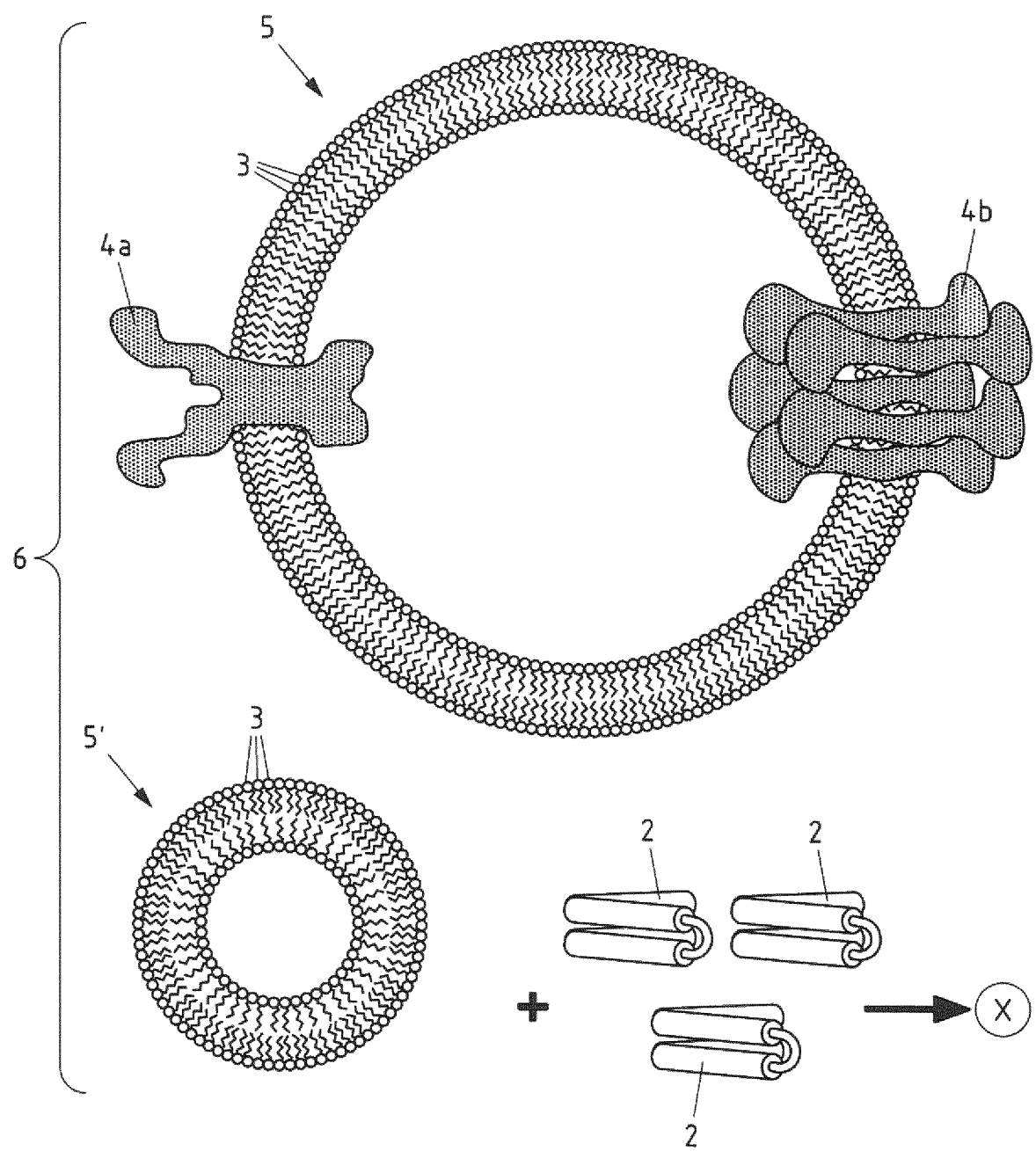
FIGS. 3a) and 3b) are schematic illustrations of the process for preparing the Saposin particle library of the invention. The starting materials for the preparation of the library, i.e. saposin A 2 and crude membrane vesicles 5, 5', are depicted in FIG. 3a). The membrane vesicles 5, 5' comprise a plurality of membrane lipids 3 and in case of 5 a plurality of membrane proteins, here exemplified in simplified form by 4a, 4b. The obtained library 7 is depicted schematically in FIG. 3b), exemplified in simplified form as the mixture of different Salipro particles 1a, 1b and 1c that differ in at least one of lipid content, protein cargo content and size. Particles 1a and 1b comprise membrane proteins 4a, 4b. Particle 1c is an "empty" lipid-only particle.
Figure 3B:
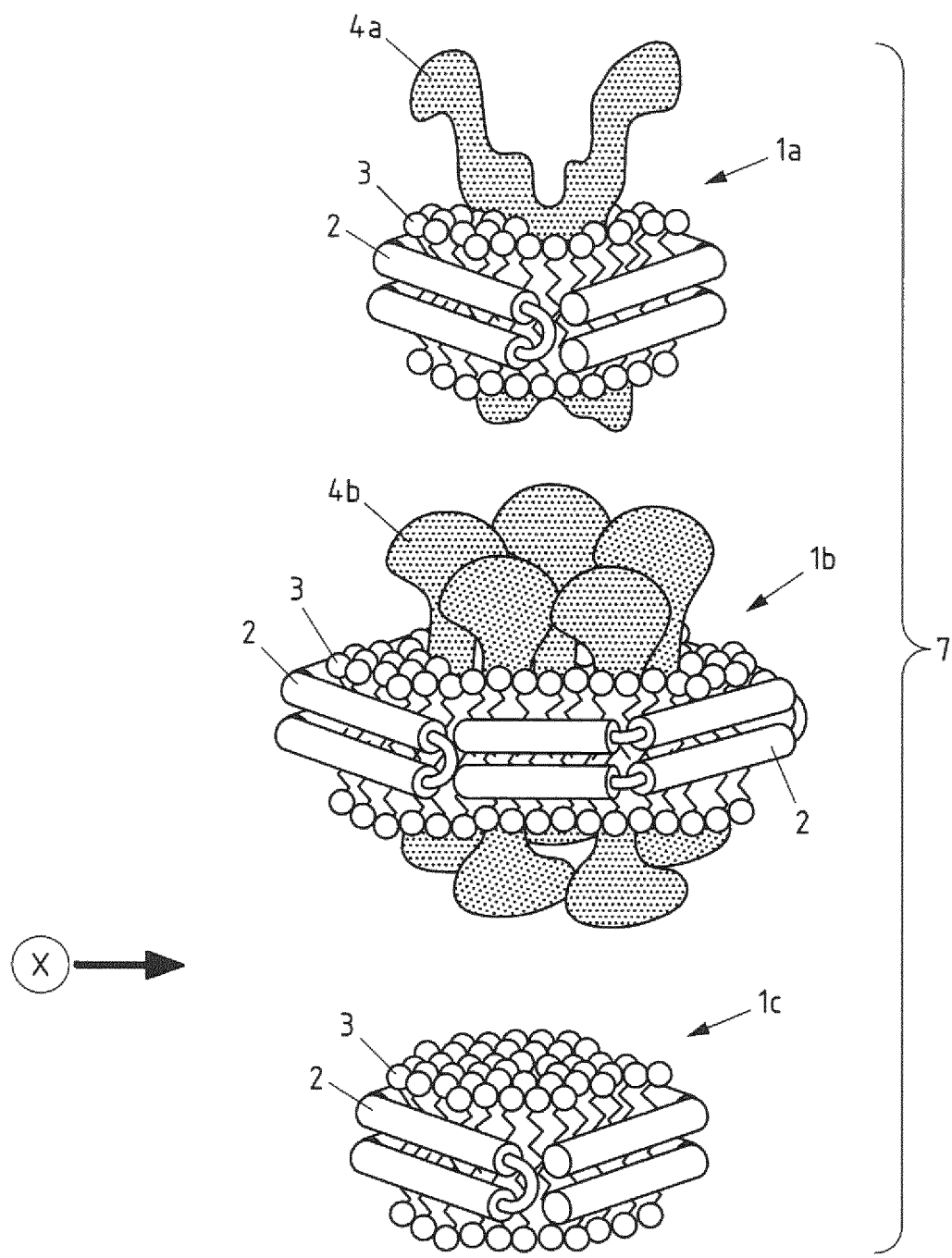

FIGS. 3a) and 3b) depict—again in simplified and schematic form—the process according to the invention for preparing a Salipro particle library 7 from crude membrane vesicles 5. In FIG. 3b) the library 7 is depicted schematically as the mixture of different representative Salipro particles 1a to 1c that differ in their membrane lipid 3 and optionally protein cargo 4a, 4b and/or size. Of course, in reality, library 7 will encompass thousands of different Salipro particles. Similarly, starting mixture 6 will comprise a high number of different crude membrane vesicle.

As shown in FIG. 3a), the particles 1a to 1c of the invention are prepared by mixing purified SAPLIP 2 with crude membrane vesicles 5, 5' and allowing the self-assembly X of the particle 1. The composition 6 comprising the crude membrane vesicles 5 and 5' can be a crude membrane fraction directly obtained after cell or cell organelle lysis. Vesicles 5 and 5' usually form spontaneously upon lysis or membrane rupture. The starting composition 6 is only depicted schematically as containing representative vesicles 5 and 5', one of which (5') is small and may only contain membrane lipids, the other of which (5) is larger and contains membrane proteins 4a and 4b in addition to membrane lipids 3. The crude membrane vesicles employed as starting material 6 in the process of the invention can be very heterogenous in size and content. A homogenization or particular vesicle generation step is not necessarily required, but possible. Of course, also a composition comprising more uniform crude membrane vesicles can be used as starting material 6.

FIG. 3a) shows the preparation of the library 7 shown in FIG. 3b). The particles 1a to 1c of the invention are prepared by mixing purified SAPLIP 2 with crude membrane vesicles 5, 5' comprising membrane lipids 3 and optionally one or more membrane proteins 4a and/or 4b, both of which are derived from the crude membranes. Self-assembly X of the particle 1 then occurs, e.g. at a pH of from about 5.0 to about 10.0. The crude membrane vesicles 5, 5' can optionally comprise or be associated with detergent molecules (not depicted herein). The same can be true for the Saposin molecules 2. The membrane lipids 3 associated with the membrane proteins 4a and/or 4b are preferably exclusively a carry-over from the membrane protein's native lipid environment in the cell or organelle membrane prior to the provision of crude membrane vesicles 5, 5'. In the particles 1a and 1b, the respective membrane protein 4a and 4b is embedded in components of the hydrophobic portion of the membrane from which it is obtained. Preferably, the membrane protein is in the same or a similar conformation as in its native membrane-bound state.

FIG. 3b) shows a Salipro particle library comprising representative particles 1a, 1b and 1c. Particles 1a and 1b comprise membrane proteins 4a, 4b. Particles 1a to 1c shown as particular embodiments of the invention (also depicted in more detail in FIGS. 2a) to 2f) are approximately disc-shaped, having a flat, discoidal, roughly circular to square-shaped lipid bilayer circumscribed by the amphipathic α-helices of two or three SAPLIP molecules 2. The lipids 3 of the crude membrane vesicles 5, 5' assemble into a discoidal bilayer-like structure of discrete size in the interior of the particles 1a to 1c. The SAPLIPs 2 define the boundary of the discoidal bilayer in the particles 1a to 1c, the interior of which is hydrophobic, i.e. comprised of lipid fatty acyl chains and lacking a hydrophilic or aqueous core. The particles 1a to 1c are held together mainly by the hydrophobic interactions of the lipids 3 of the crude membrane vesicles 5 within the bilayer core of the particles 1a to 1c and hydrophobic interactions between the lipids 3 of the crude membrane vesicles 5 and the hydrophobic portions of the amphiphilic helices of the SAPLIPs 2 facing the interior of the particle. In its smallest form, the particle 1c is thought to contain two SAPLIP molecules 2 and at least around 2-5 lipid molecules 3 of the crude membrane vesicles 5,5'. However, the particles of the invention 1a to 1c are flexible in size. Depending on the size of the cargo to be incorporated (e.g. lipid domains, membrane proteins etc.) and the molar ratio of components used in their preparation, it can accommodate multiple, i.e. more than two, SAPLIPs 2, many more lipids 3 of the crude membrane vesicles 5 and optionally one or more membrane proteins 4a and/or b 4b. For example, the particle may contain two to twenty, in particular two to ten SAPLIPs 2 and optionally one or more membrane proteins. Depending on the size of the membrane protein 4a, 4b incorporated in the particle 1a, 1b, the particles can be substantially larger than the lipid-only particle 1c. Generally, an increase in particle size will also be reflected by the number of SAPLIPs 2 per particle, which can be more than two. The particle of the invention may for example comprise two to twenty, in particular two to ten SAPLIP molecules 2.

Figure 4A:
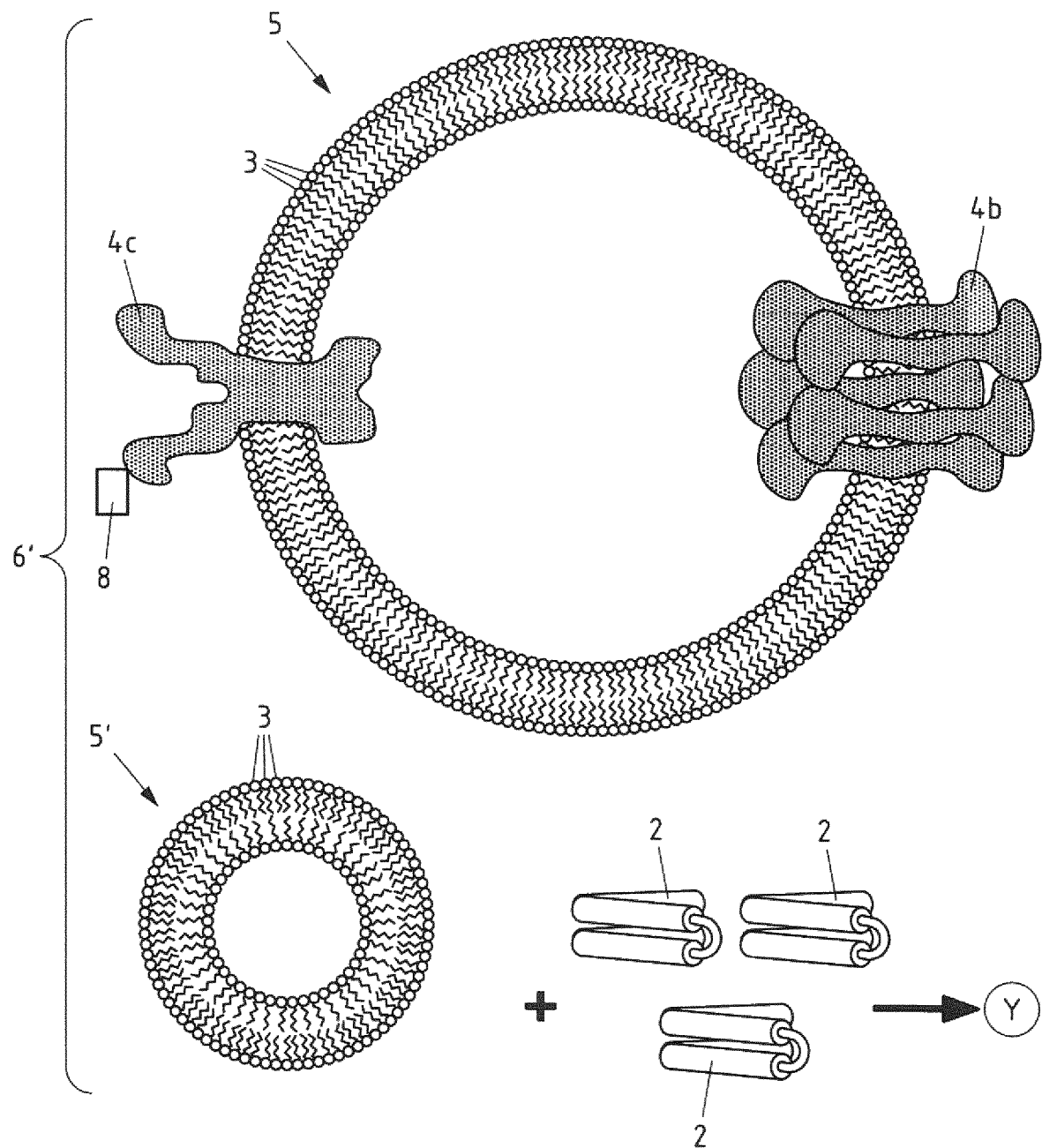
FIGS. 4a) and 4b) are schematic illustrations of the process for preparing the Saposin particle library of the invention, wherein a membrane protein 4c present in the crude membrane vesicles 5 is tagged with an affinity tag 8. The starting materials for the preparation of the library, i.e. saposin A 2 and crude membrane vesicles 5, are depicted in FIG. 4a). The membrane vesicles 5 comprise membrane lipids 3 and a plurality of membrane proteins, here exemplified in simplified form by 4c, 4b. The obtained library 7' is depicted schematically in FIG. 4b), exemplified in simplified form as the mixture of different Salipro particles 1d, 1b and 1c that differ in at least one of lipid content, protein cargo content and size. Particle 1d comprises membrane protein 4c with the affinity tag 8 appended thereto. Particle 1b comprises oligomeric membrane protein 4b. Particle 1c is an "empty" lipid-only particle.
Figure 4B:
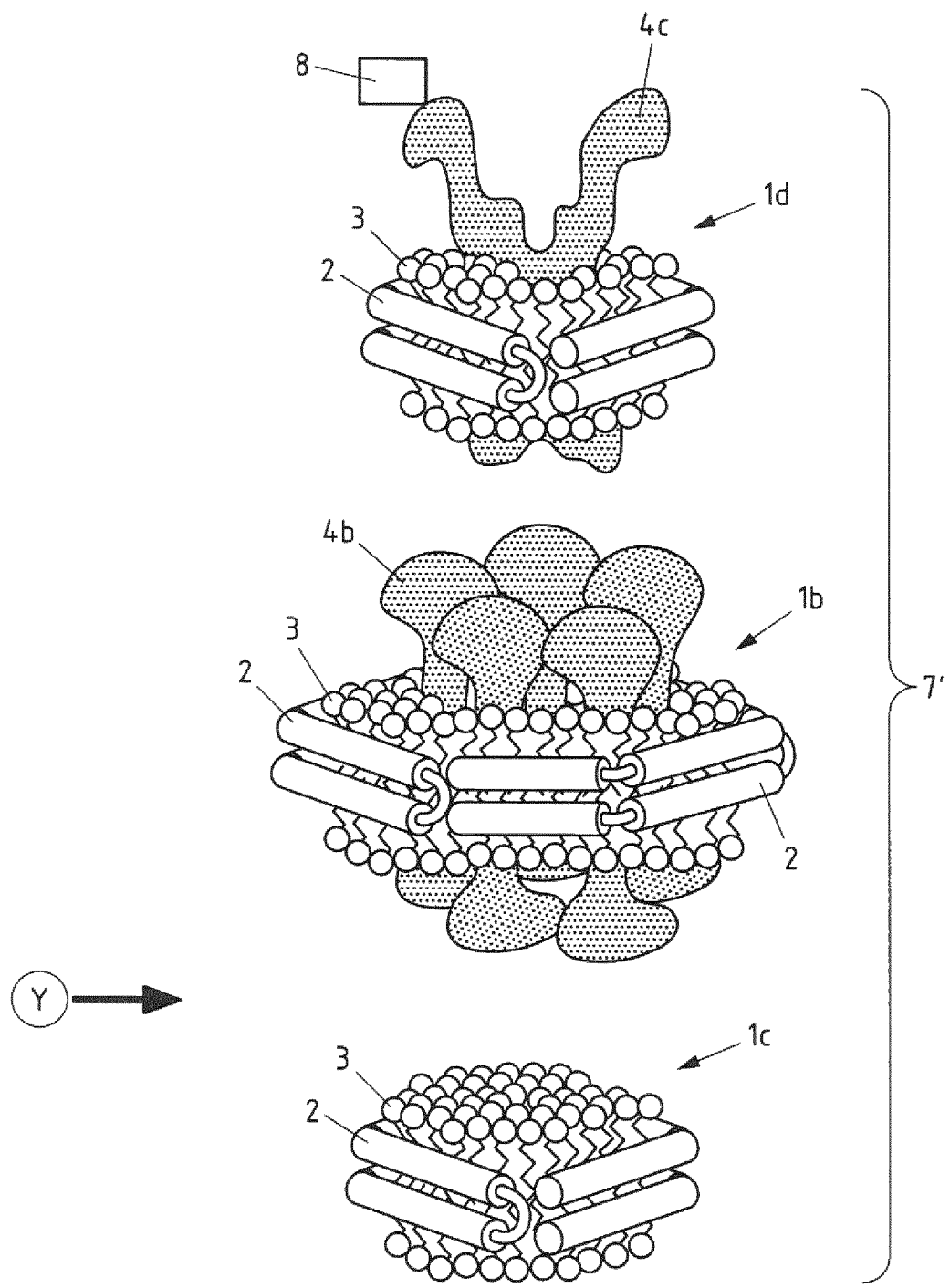

FIGS. 4a) and 4b) are basically identical to FIGS. 3a) and 3b) with the difference, that a membrane protein 4c with an affinity tag 8 is comprised in the crude membrane vesicle 5 of the starting material 6. As a result of the self-assembly Y following contacting of the crude membrane vesicles 5. 5' with purified SAPLIPs 2, the obtained library 7' comprises particle 1d containing membrane protein 4c and the affinity tag 8. The description of FIG. 3a) and b) above equally applies to FIG. 4a) and b).

Figure 5:
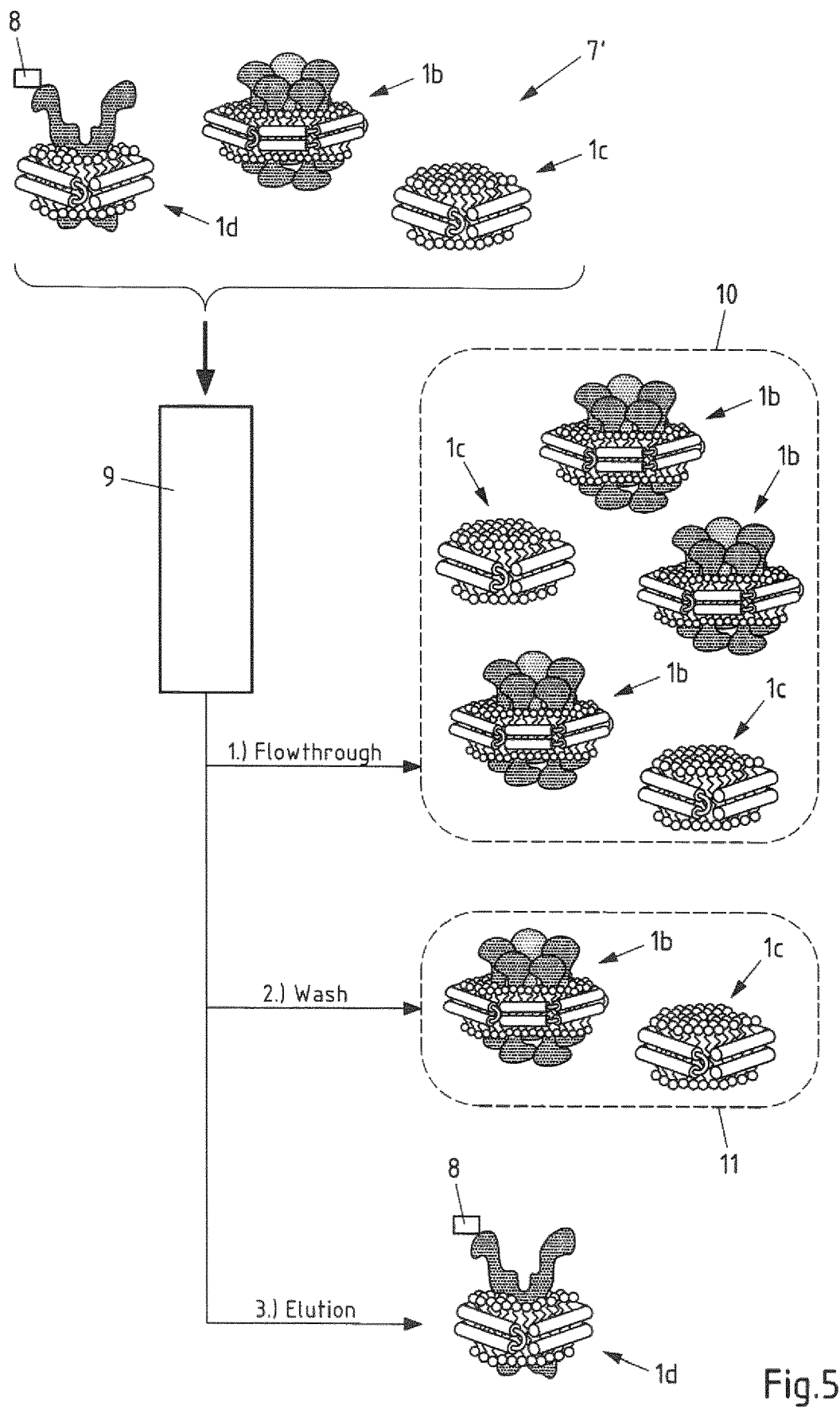
FIG. 5 is a schematic illustration of one embodiment of the process for preparing a particle of the invention by conducting step f) as described above. The library 7' of FIG. 4b) is subjected to a purification step using an affinity column 9. Schematic representation of the content of the 1.) Flowthrough; 2.) Wash; and 3.) Elution fractions exiting from the column 9 are also shown.

FIG. 5 is a schematic illustration of one embodiment for the process according to the invention for purifying a particular particle from the library of the invention by conducting step f) as described more generally above. As starting material, library 7' is used which can be obtained as shown in FIG. 4a) and b) above. The library 7' is subjected to an affinity purification, for example, using an affinity column 9. The column 9 contains a recognition entity that binds to the affinity tag 8. For example, if affinity tag 8 is a His-tag, then the recognition entity in affinity column 9 is Ni-Nta. Whereas a purification in column form is depicted in FIG. 5, batch-purification processes are also possible.

Passage of the library 7' through the affinity column 9 leads to the specific binding of particle 1d via its affinity tag 8 to the recognition entity in column 9. Particles 1b and 1c as well as other components of the library or debris do not bind or only bind unspecifically to the affinity column 9. Thus, the flow-through 1.) obtained is essentially free of particles 1d. Some residual components of the library, such as particles 1b and 1c, which may have bound unspecifically to affinity column 9 are removed by performing at least one wash step 2.). Finally the purified particle 1d can be eluted in an elution step 3.) by disrupting the binding between affinity tag 8 to the recognition entity in affinity column 9. Such disruption can be performed by a high salt wash, by enzymatic cleavage or, in case of a His-tag/Ni-NTA tag/ recognition entity pair with imidazole. The Elution fraction obtained after 3.) contains particle 1d of the invention in purified form.

EXAMPLES

The following examples serve to further explain the invention in more detail, specifically with reference to certain embodiments and Figures which, however, are not intended to limit the present disclosure.

The following abbreviations will be used:
GF-buffer pH 7.5:20 mM HEPES, pH 7.4 and 150 mM NaCl
GFP Green Fluorescent Protein
Glut5: Transporter, membrane protein
HEPES: 4-(2-hydroxyethyl)-1-piperazineethanesulfonic acid
His Histidine
HN buffer: 20 mM HEPES, 150 mM NaCl, pH 7.4
HN-D buffer HN buffer containing 0.2% DDM
M: molar
RT: room temperature
SEC: Size-exclusion chromatography
TCEP: tris(2-carboxyethyl)phosphine
TEV: Tobacco Etch Virus
Tris: Tris(hydroxymethyl)aminomethane Purified saposin A used in the below experiments was prepared as follows. Saposin A protein expression was carried out using a vector with the coding region for human saposin A (SEQ ID NO: 1) inserted into a pNIC-Bsa4 plasmid and transformed and expressed in *E. coli* Rosetta gami-2 (DE3) (Novagen) strains. Cells were grown at 37° C. in TB medium supplemented with Tetracycline, Chloramphenicol and Kanamycin and induced with 0.7 mM IPTG. Three hours after induction, the cells were collected by centrifugation at 12.000×g for 15 min. The supernatant was discarded, the cell pellet was resuspended using lysis buffer (20 mM Hepes pH 7.5, 150 mM NaCl, 20 mM Imidazol) and disrupted by sonication. Lysates were subjected to centrifugation at 26.000×g for 30 min, the supernatant heated to 85° C. for 10 min, followed by an additional centrifugation step at 26.000×g for 30 min. Preparative IMAC purification was performed by batch-adsorption of the supernatant by end-over-end rotation with Ni Sepharose™ 6 Fast Flow medium for 60 min. After binding of saposin A to the IMAC resin, the chromatography medium was packed in a 10-mm-(i.d.) open gravity flow column and unbound proteins were removed by washing with 15 bed volumes of lysis buffer. The resin was washed with 15 bed volumes of wash buffer WB2 (20 mM Hepes pH 7.5, 150 mM NaCl, 40 mM Imidazol). Saposin A was eluted by addition of five bed volumes of elution buffer EB (20 mM Hepes pH 7.5, 150 mM NaCl, 400 mM Imidazol). The eluate was dialyzed overnight against gel filtration buffer GF pH 7.5 (20 mM Hepes pH 7.5, 150 mM NaCl) supplemented with recombinant TEV protease. TEV protease containing an un-cleavable His-tag was removed from the eluate by passing it over 2 ml IMAC resin. Cleaved target proteins were concentrated to a volume of 5 ml using centrifugal filter units and loaded onto a HiLoad Superdex™ 200 16/60 GL column using an ÄKTAexplorer™ 10 chromatography system (both GE Healthcare). Peak fractions were pooled and concentrated to 1.2 mg/ml protein. The protein sample was flash frozen in liquid nitrogen and stored at −80 C.

Example 1a

Crude yeast cell membrane fractions were obtained from GFP-GLUT5 expressing yeast cells. The membrane fraction, which contained spontaneously formed crude membrane vesicles, was incubated with detergent and Saposin A, followed by removal of detergent-micelles using gel-filtration chromatography/size-exclusion chromatography (SEC) in detergent-free buffer. This lead to the self-assembly of the membrane components present in the initial mixture into a library of nanoscale Salipro particles. In particular, monodisperse Salipro particles comprising membrane lipids and GFP-GLUT5 could be identified within this library.

1. Membrane Preparation

Crude yeast membranes were obtained from yeast cells expressing rat GLUT5 from a GAL1 inducible TEV cleavable GFP-His8 2μ vector pDDGFP2 known in the prior art. The vector was transformed into the S. cerevisiae strain FGY217 (MATa, ura3-52, lys2Δ201, and pep4Δ) which then overexpressed GFP-GLUT5 in its cell membrane.

To generate crude membranes, cells were harvested from 12 L. S. cerevisiae cultures, resuspended in buffer containing 50 mM Tris-HCl pH 7.6, 1 mM EDTA, 0.6 M sorbitol, and lysed by mechanical disruption. Membranes were isolated by ultracentrifugation at 195,000 g for 3 h, homogenized in 20 mM Tris-HCl pH 7.5, 0.3 M sucrose, 0.1 mM $CaCl_2$, frozen in liquid nitrogen and stored at −80° C.

2. Preparation of Salipro Particle Libraries

20 μl of crude yeast membranes containing spontaneously formed crude membrane vesicles harboring inter alia GFP-GLUT5 were mixed with 60 μl HN buffer (20 mM HEPES, 150 mM NaCl, pH 7.4) and 20 μl HN buffer supplemented with 5 DDM, followed by incubation at 4° C. for 1 h. The membrane lysate was then cleared from debris and protein aggregation by ultracentrifugation using a TLA-55 rotor at 47 krpm (100,000 g) for 30 min. 5 μl of the cleared membrane fraction was then mixed with increasing amounts (5-10-20-30-40 μl) of Saposin A (1.2 mg/ml, HN-buffer) and incubated 5 min at 37° C. to allow self-assembly of the Salipro particles. The only lipids present in the setup are those derived from the crude membranes and crude membrane vesicles.

Thereafter, the sample volume was adjusted to 50 μl with HN buffer and centrifuged 10 min at 13 krpm. SEC analysis was performed (using a Shimadzu HPLC system): 35 μl sample was injected to a 5/150 Superose6 increase column (GE Healthcare) with a flow rate at 0.3 ml/min and the presence of the fluorescent GFP tag monitored online. The SEC buffer consisted of HN buffer without any of detergent.

As a negative control, Saposin A was entirely omitted from the experimental setup (0 μl SapA), the volume adjusted to 50 μl using NH buffer and the sample was then treated as described before.

3. Results

Figure 6:
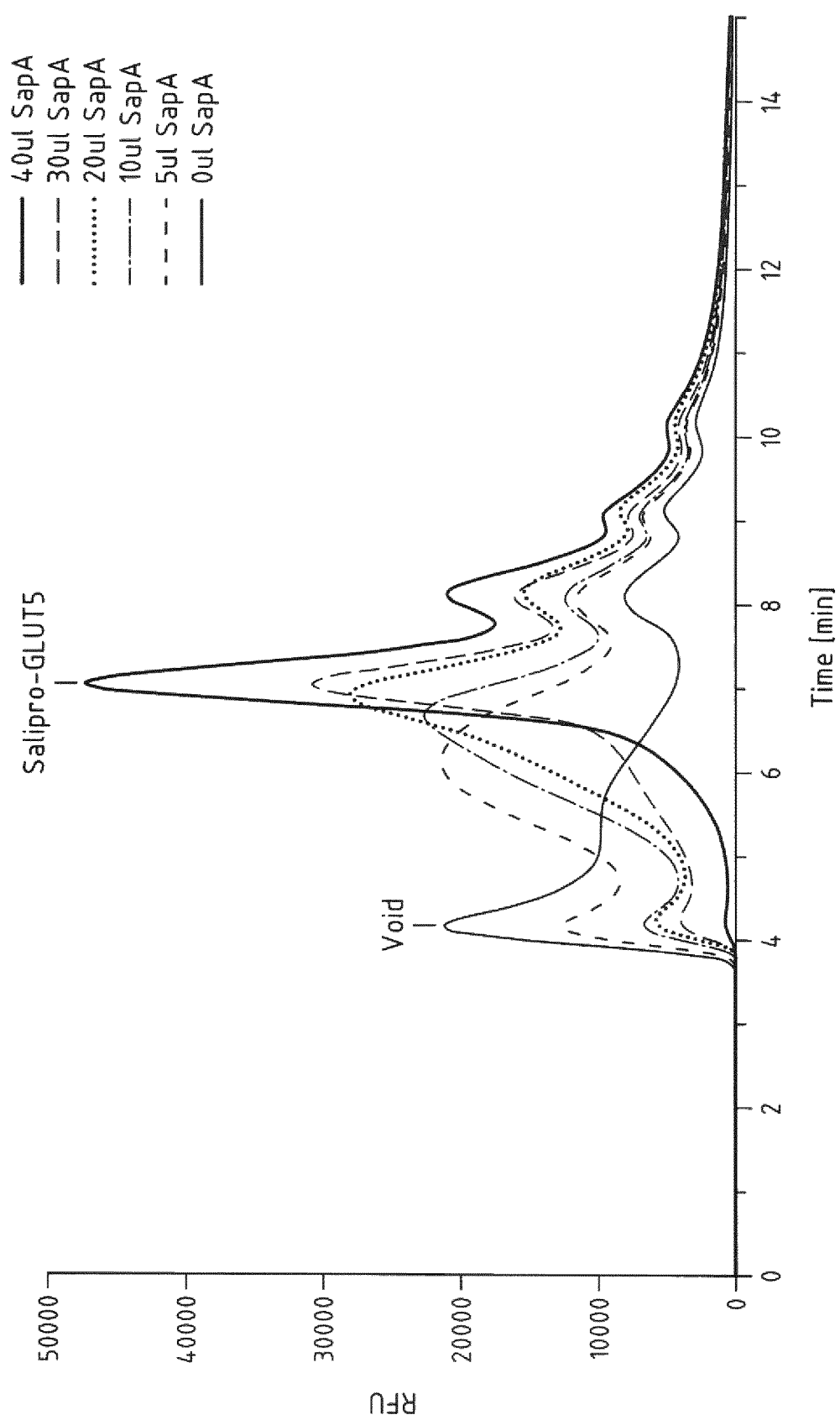
FIG. 6 shows the results of Example 1a. The FIG. shows Fluorescence Size-Exclusion Chromatography (FSEC) analysis of incorporation of fluorescent GFP-GLUT5 into Salipro nanoparticles from crude membranes.

The results, which are depicted in FIG. 6, demonstrate that it is possible to incorporate and stabilize membrane lipids membrane proteins such as GFP-GLUT5 from crude cell membranes into soluble Salipro particles, displaying a monodisperse peak. Increasing amounts of Saposin improve the incorporation efficiency and monodispersity of the peak. Accordingly, Saposin A, lipids from the crude membranes and GFP-GLUT5 associate in such way as to form water-soluble particles with an incorporated membrane protein. Whereas only GFP-GLUT5 was monitored in the SEC analysis via its fluoresence, the obtained Salipro particle library also contains a plethora of other Salipro particles harboring the remaining membrane proteome and lipidome of the yeast cell that the crude membrane fraction was obtained from. This can, e.g. be confirmed by mass spectrometry, SDS-PAGE and/or by probing with antibodies which bind to other native yeast membrane proteins and lipids present in the obtained salipro particle library.

As a negative control, in the absence of Saposin from the setup, GFP-GLUT5(and, accordingly, also the remaining membrane proteins) is not soluble and aggregates (see high void peak).

Example 1b

1. Setup

Crude yeast membranes containing crude membrane vesicles and rat GLUT5 were prepared as described in example 1a.

2. Variation of the Process for Salipro Particle Library Formation.

Two different approaches to make Salipro-GFP-GLUT5 particles from crude membrane extract were evaluated.

For the first approach, 25 μl of saposin A (0.75 mg/ml) were added to 1 μl crude membrane extract containing crude membrane vesicles and GFP-GLUT5 and incubated for 5 min at 37° C. Thereafter 24 μl HN-D buffer was added to the mix and incubated for an additional 5 min at 37° C. The sample was then centrifuged for 10 min at 13 krpm and SEC analysis was performed as in example 1a.

For the second approach, 1 ul crude membrane extract containing crude membrane vesicles and GFP-GLUT5 were first supplemented by adding 24 ul HN-D buffer, followed by incubation at 37° C. for 5 min. The sample was then centrifuged for 10 min at 13 krpm. The lysate suspension was collected and 25 μl saposin A (0.75 mg/ml) were added and incubated for an additional 5 min at 37° C. The sample was then analyzed by SEC as described in example 1a.

3. Results

Figure 7:
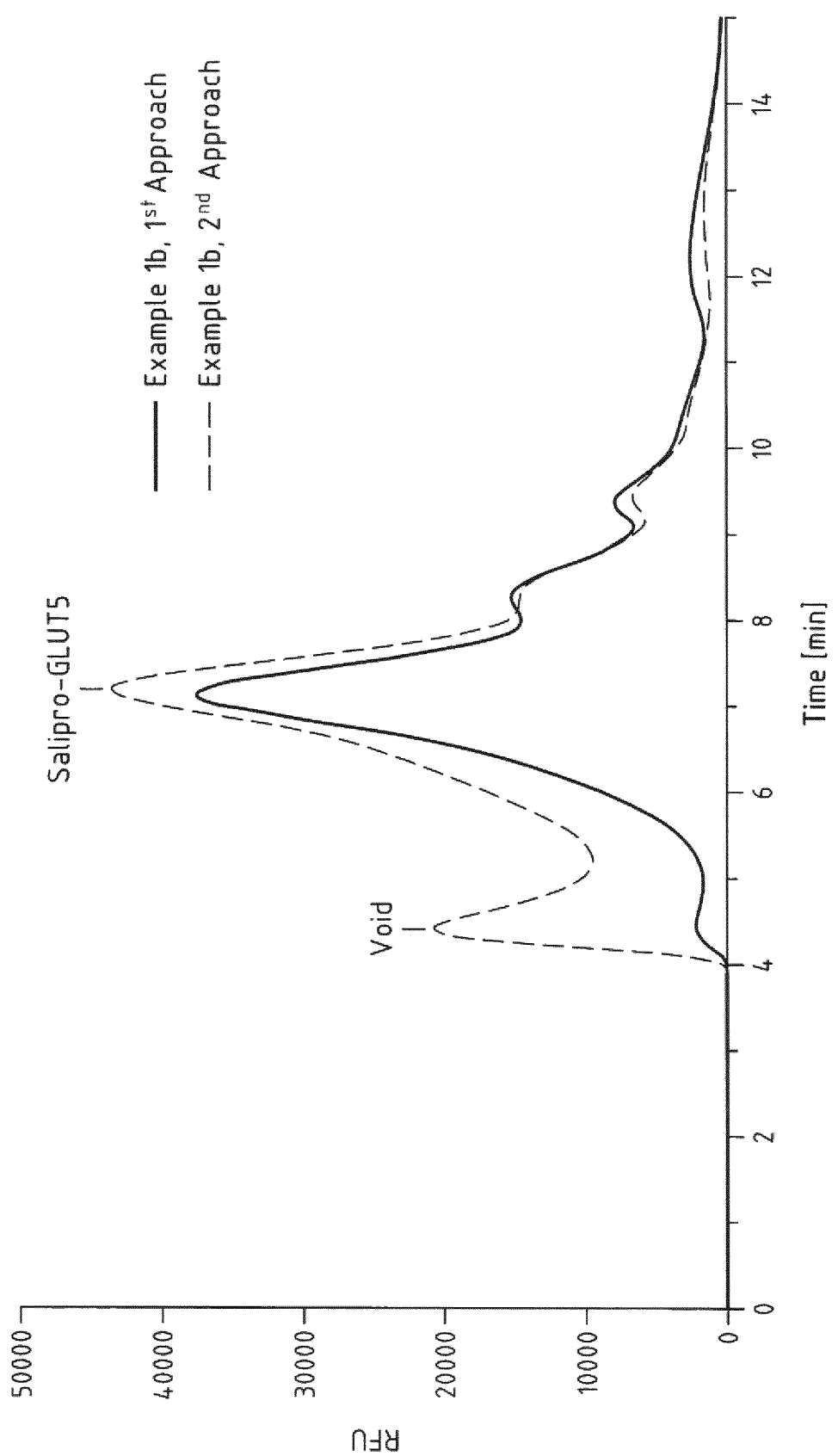
FIG. 7 shows the results of Example 1b. The FIG. again shows FSEC analysis of incorporation of fluorescent GFP-GLUT5 into Salipro nanoparticles from crude membranes.

The data shown in FIG. 7 demonstrate that both approaches work to obtain Salipro particle libraries with soluble Salipro-GFP-GLUT5 particles, independently if saposin A was added before or after incubation of the crude membranes with HN-D buffer at 37° C. for 5 min. In both instances, the natural lipids of the crude membranes are still present. Interestingly, when adding saposin A directly to crude membranes, only very little protein aggregation is seen in the void volume. Importantly, both methods work, which gives the process a certain flexibility when reconstituting Salipro particle libraries from complex crude membrane extracts.

Example 2

1. Setup

Crude yeast membranes containing rat GFP-GLUT5 and crude membrane vesicles were prepared as described in example 1a.

2. Salipro Formation, Titration

20 μl of yeast crude membranes were mixed and solubilized with 60 μl HN buffer and 20 μl HN buffer supplemented with 5% DDM at 4° C. for 1 h. The membrane lysate was then cleared from debris and protein aggregation by ultracentrifugation using a TLA-55 rotor at 47 krpm (100,000 g) for 30 min. 5 μl of the cleared membrane lysate, which contained crude membrane vesicles, was then mixed with different volumes (12, 20, 30 and 40 μl) of saposin A (4 mg/ml, HN buffer) and incubated 5 min at 37° C. Thereafter the sample volumes were adjusted to 50 μl with HN buffer and centrifuged 10 min at 13 krpm. SEC analysis was performed (using a Shimadzu HPLC system) and 35 µl sample was injected to a 5/150 Superdex 200 increase column (GE healthcare) with a flow rate at 0.3 ml/min and the presence of the fluorescent GFP tag monitored online. Again, the SEC was performed using HN buffer, in the absence of detergent, to facilitate membrane protein reconstitution into the Salipro particles.

As a control, 5 µl of the cleared membrane lysate was mixed with 45 µl NH buffer supplemented with 0.03% DDM and centrifuged 10 min at 13 krpm. SEC analysis was performed (using a Shimadzu HPLC system) in HN buffer containing 0.03% DDM and 35 µl sample was injected to a 5/150 Superdex 200 increase column (GE healthcare) with a flow rate at 0.3 ml/min and the presence of the fluorescent GFP tag monitored online. The purpose of this control sample (yield control sample) was to act as a reference point to determine the amount of GFP-GLUT5 that can be solubilized in the permanent presence of detergent, in contrast to the yield of GFP-GLUT5 reconstituted in Salipro particles in a detergent-free buffer system.

3. Results

Figure 8:
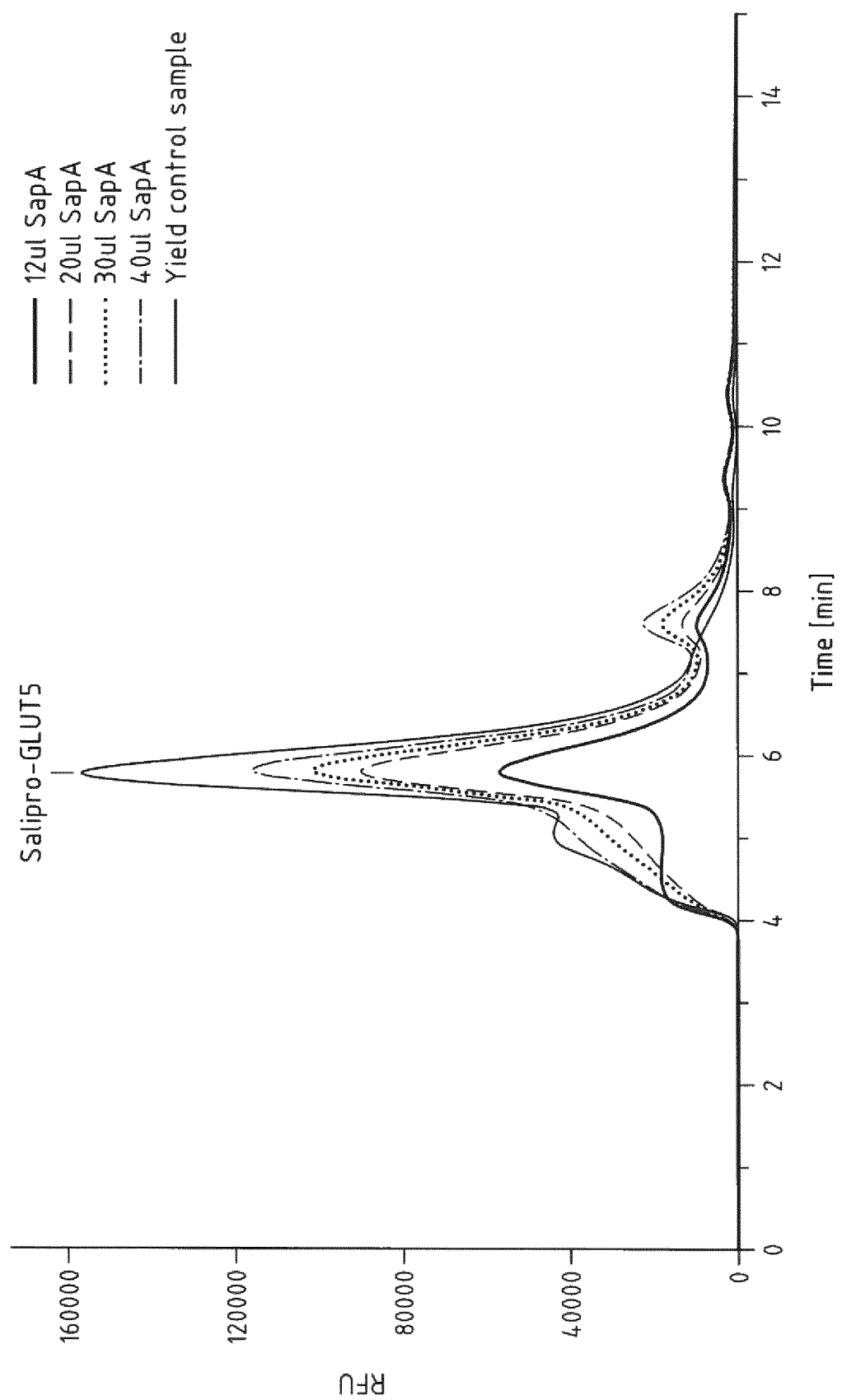
FIG. 8 shows the results of Example 2. The FIG. shows FSEC analysis of incorporation of fluorescent GFP-GLUT5 into Salipro nanoparticles from crude membranes. The "yield control sample" is run in the continuous presence of detergent in the buffer, while all other samples are run in a detergent-free buffer system.

The results depicted in FIG. 8 show that an increasing amount of saposin A improves the amounts of GFP-GLUT5 reconstituted into the Salipro particles of the library.

To quantify the reconstitution yields, the percentage of the GFP-GLUT5 peak value from the "yield control sample" was compared to the peak values of the reconstituted samples. This showed that 36% of GFP-GLUT5 were reconstituted for the 12 µl SapA sample, 57% for the 20 µl SapA sample, 65% for the 30 µl SapA sample and 74% for the 40 µl SapA sample. Altogether, this demonstrates that it is possible to increase the incorporation of membrane proteins from crude membranes into Salipro particles with increasing amounts of Saposin.

Example 3

The solubility of Salipro membrane protein components of the library was analyzed 1. Background Crude membranes contain a plethora of different membrane proteins. In the process according to the invention, not only fluorescently labeled GFP-GLUT5, but also the various other yeast membrane proteins from crude membranes are incorporated into Salipro particles. In the absence of detergent, the membrane protein fraction is not soluble and aggregates in detergent-free buffer systems, leading to the formation of a large void-peak in SEC analysis. However, once embedded in Salipro particles, it could be shown that the membrane proteins present in the Salipro particle library remain soluble in detergent-free buffer systems.

2. Setup

In the same experimental setup as in Example 1a, here the SEC signals were analyzed based on UV absorptions at 280 nm instead of GFP fluorescence, with a focus (zoom) on the void peak indicating aggregated membrane proteins.

3. Results

Figure 9:
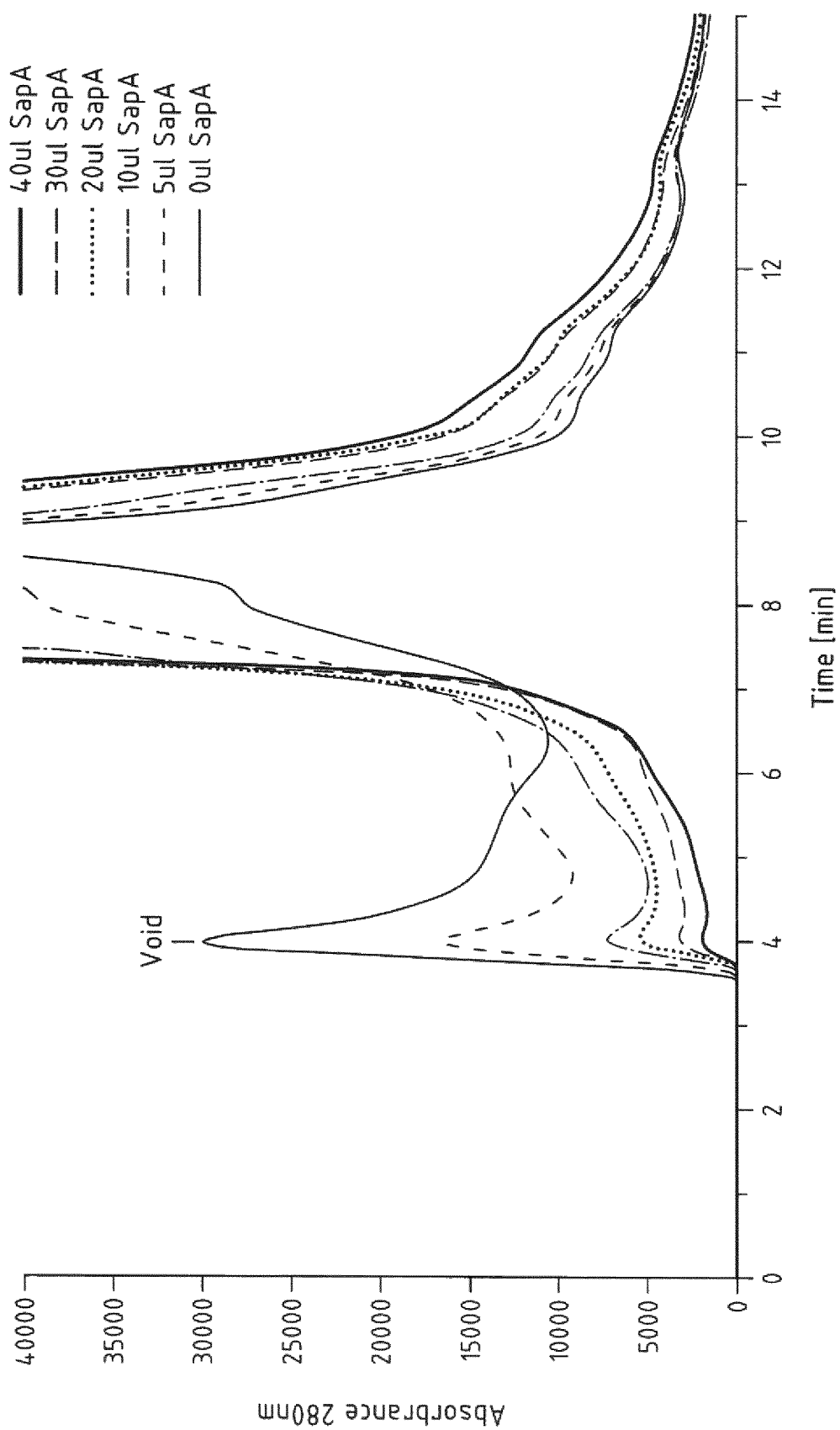
FIG. 9 shows the results of Example 3. The FIG. shows SEC analysis with increasing amounts of saposin A added. In the presence of saposin A, membrane proteins from crude membranes are incorporated into a library of Salipro particles and remain soluble in a detergent-free buffer system.

In the absence of saposin, the membrane proteins from crude membranes aggregate in detergent-free buffer systems, as indicated by a large void peak appearing in the SEC analysis at around minute 4 (see FIG. 9, 0 µl SapA).

In contrast, by increasing the amount of saposin that is added to the lysate, the amount of aggregated membrane proteins decreases accordingly. This indicates that membrane proteins remained soluble due to incorporation into the Salipro particles of the obtained membrane proteome library. Note that almost no protein aggregates were detected in the sample containing the highest amount of saposin (FIG. 9, 40 µl SapA).

Altogether this data indicates that after being subjected to the method of the invention, all membrane proteins from the crude membrane vesicles remain soluble upon detergent removal in a detergent-free environment, due to successful reconstitution into a library of corresponding Salipro nanoparticles. Thus it is possible to generate a particle Salipro-membrane protein/proteome and/or membrane lipid/lipidome library originating from crude membrane.

Example 4

The solubility of Salipro Membrane Lipid Components of the Library was Analyzed

1. Setup

In the same experimental setup as in Example 1a, a different SEC analysis performed (note the difference in axis scale and axis intercept in FIGS. 9 and 10), with a focus (zoom) to peaks originating from monomeric Saposin and lipid-only Salipro particles.

2. Results

Figure 10:
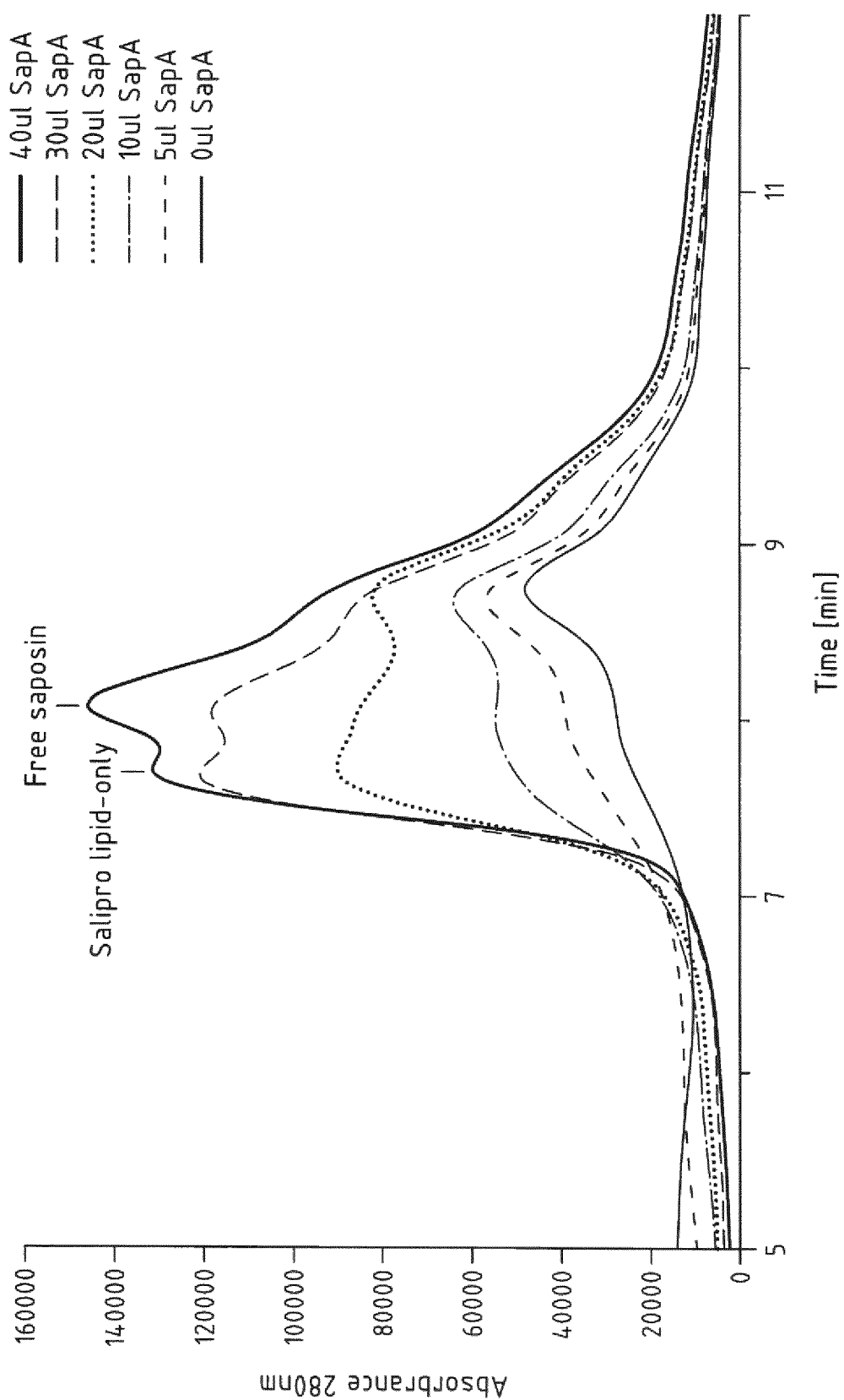
FIG. 10 shows the results of Example 4. The FIG. shows SEC analysis with increasing amounts of saposin A added. In the presence of saposin A, membrane lipids from crude membranes are incorporated into a library of Salipro particles and remain soluble in a detergent-free buffer system.

The results depicted in FIG. 10 indicate that adding Saposin A to crude membranes leads to the formation not only of membrane protein containing Salipro particles, but also of lipid-only (i.e. "empty") Salipro particles. Increasing amounts of Saposin (5, 10, 20, 30 and 40 µl) also lead to the increased formation of lipid-only Salipro particles. SEC analysis reveals a peak originating from lipid-only Salipro particles at 7.6 min (indicated), while the corresponding peak of monomeric Saposin ("free Saposin") appears at 8.2 min (indicated). The data indicate that the lipids from crude membrane vesicles allow for the formation of Salipro lipid-only particles at neutral pH.

As a negative control, one sample was analyzed in the absence of saposin (0 µl SapA).

This experiment using increasing amounts of Saposin was performed on a Superose 6 5/150 column (GE Healthcare). Since the SEC separation of the two saposin-related peaks are not well separated, the experiment was repeated with a Superdex 200 5/150 column (GE Healthcare) (FIG. 11)

Figure 11:
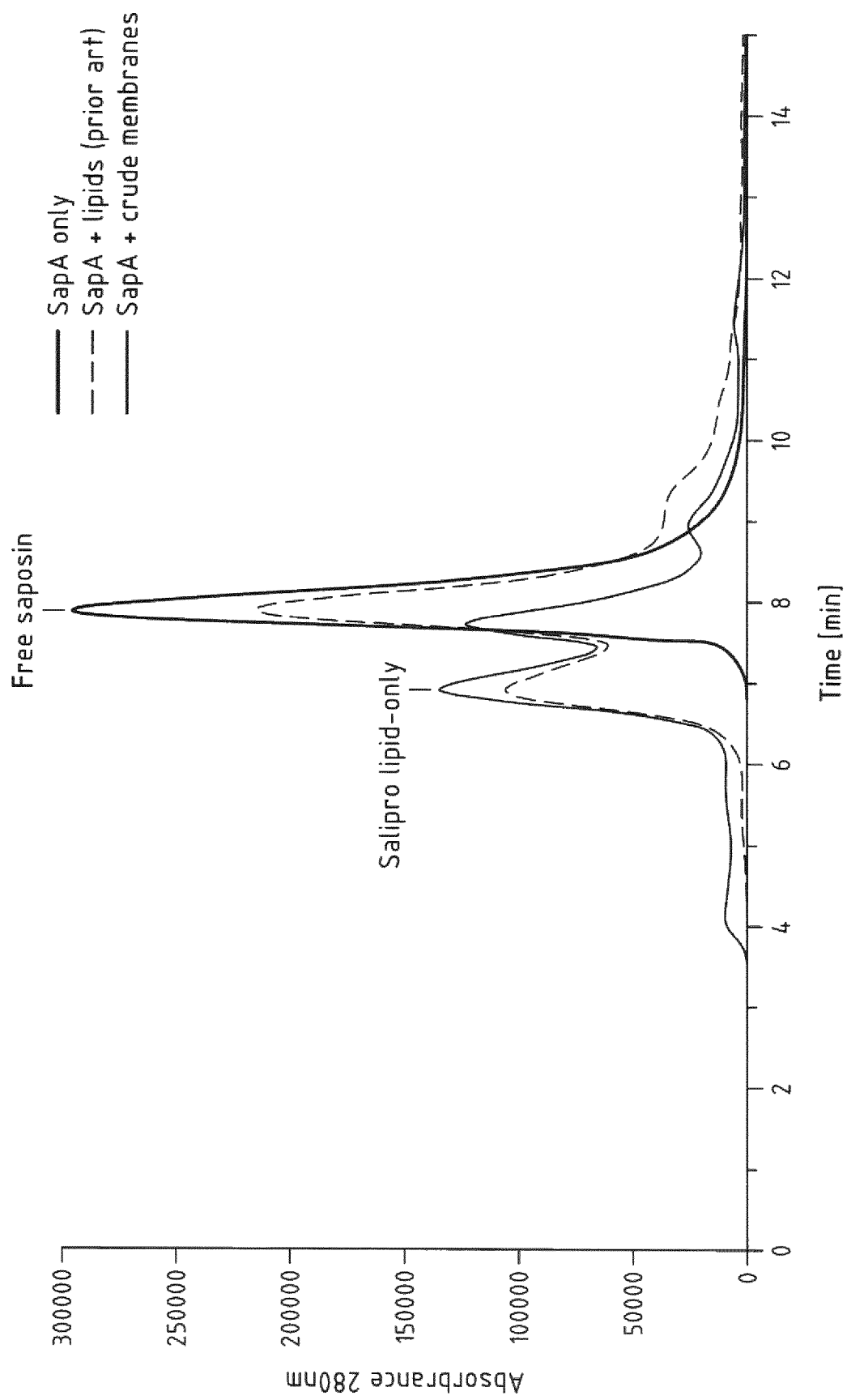
FIG. 11 shows further results of Example 4. The FIG. shows SEC analysis of saposin A, prior art Salipro particles, and Salipro particles prepared according to the invention.

One sample was prepared exactly as described in example 2 for the "12 ul SapA" Sample (designated in FIG. 11 as "Sap+crude membrane"). This time, SEC analysis was performed using UV absorbance at 280 nm. As a first control, one sample contained only Saposin A in order to indicate the position of lipid-free, monomeric Saposin in the SEC profile. A second control sample contained Saposin A particles obtained by the method described in WO 2014/095576 A1, i.e. by incubating Saposin A with purified lipids, The data presented herein clearly demonstrates that both cell membrane lipidome as well as proteome can be incorporated into Salipro particles to form respective libraries.

Example 5

In this Example, a library of Salipro particles was prepared as described in the Examples above, however, only HN buffers without detergent were used. This experiment also resulted in successful incorporation of GFP-GLUT5 from crude membranes into soluble Salipro particles.

Example 6

Purification of Specific Saposin Particles from Libraries

In this Example, a membrane protein library obtained according to Example 3 is prepared. The library Salipro particles covering essentially the entire yeast membrane proteome and also includes Salipro particles comprising GFP-GLUT5. The latter particles are purified by means of the TEV cleavable GFP-His8 tag present in the GFP-Glut5 construct.

The library is subjected to a Ni-NTA affinity purification (e.g., Qiagen) according to the manufacturer's instructions. After the prescribed wash steps, the GFP-GLUT5 containing Salipro particles are eluted via TEV protease cleavage or imidazole.

The invention claimed is:

1. A process for preparing a library of saposin lipoprotein particles, wherein library means a set of different saposin lipoprotein particles comprising a heterogenic mixture of saposin lipoprotein particles with different membrane lipid and membrane protein compositions, wherein the particles comprise membrane components from a cell or an organelle membrane and a lipid binding polypeptide that is a saposin-like protein belonging to the SAPLIP family of lipid interacting proteins or a derivative form thereof, wherein the process comprises the steps of
   a) providing a mixture of crude membrane vesicles obtained from an archaeal, eukaryotic or a prokaryotic cell or an organelle membrane and wherein the crude membrane vesicles comprise both membrane lipids as well as membrane proteins from the crude cell or organelle membranes from which they are obtained;
   b) contacting the mixture of step a) with the lipid binding polypeptide in a liquid environment;
   c) allowing for self-assembly of the particles.

2. The process according to claim 1, wherein the crude membrane vesicles of step a) are prepared by at least one of or all of the following steps:
   a.1) provision of a cell and/or a cell organelle;
   a.2) lysing or disrupting the cell and/or the cell organelle;
   a.3) obtaining a crude membrane fraction; and
   a.4) preparing crude membrane vesicles from the crude membrane fraction obtained in step a.3).

3. The process according to claim 1, wherein the process further comprises between steps a) and b) the step of
   b.1) contacting the crude membrane vesicles with a detergent in a liquid environment; wherein then in step b) the mixture obtained after step b.1) is contacted with the lipid binding polypeptide in step c) and/or
   wherein step b) takes place in the presence of a detergent.

4. The process according to claim 3, wherein the detergent is selected from the group consisting of alkylbenzenesulfonates or bile acids, cationic detergents and non-ionic or zwitterionic detergents, alkyl glycosides, glucosides, maltose-neopentyl glycol (MNG) amphiphiles, amphiphilic polymers (amphipols), macrocycle or cyclic oligomers based on a hydroxyalkylation product of a phenol and an aldehyde (Calixarene), and mixtures thereof.

5. The process according to claim 1, wherein
   i) the particles are disc-shaped,
   ii) the particles generally have a maximum diameter of from 2 nm to 200 nm;
   iii) the self-assembly of the particle in step c) is carried out at a pH from 2.0 to 10.0 and/or
   iv) wherein the process comprises in step c) or as a subsequent step d), the purification of the particles by at least partial removal of free membrane lipids, free membrane proteins, free lipid binding polypeptide, unsoluble or aggregated matter and/or detergent, wherein, optionally, the purification is performed by chromatography; ultracentrifugation; dialysis; contacting with detergent-binding biobeads; use of concentrators; or affinity purification methods.

6. The process according to claim 1, wherein the lipid binding protein is saposin A, saposin B, saposin C, saposin D or a derivative or truncated form thereof, and wherein, optionally, the derivative form of the SAPLIP is selected from
   i) a protein having at least 80% sequence identity to the full length sequence of SEQ ID NO. 1, 2, 3, 4, 5 or 6;
   ii) a protein having at least 40% sequence identity to the full length sequence of SEQ ID NO. 1, 2, 3, 4, 5 or 6, wherein said protein is amphipathic, forms at least one alpha helix, and is capable of self-assembling together with solubilized lipids into lipoprotein particles when employed in the process; and
   iii) a protein comprising the sequence of SEQ ID NO. 1, 2, 3, 4, 5 or 6 in which 1 to 40 amino acids have been deleted, added, inserted and/or substituted.

7. The process according to claim 1, wherein the particles essentially consist of the at least one lipid binding polypeptide and components of the cell or organelle membrane stemming from the cell or the organelle membrane recited in step a).

8. The process according to claim 1, wherein
   i) the particles comprise membrane lipids stemming from the cell or the organelle membrane recited in step a), wherein the membrane lipids are optionally selected from the group consisting of phospholipids, glycolipids, cholesterol and mixtures thereof, and/or wherein
   ii) at least a portion of the particles comprises membrane proteins stemming from the cell or the organelle membrane recited in step a), and wherein the membrane protein is optionally selected from the group consisting of an integral transmembrane protein, an integral monotopic membrane protein, a peripheral membrane protein, an amphitropic protein in a lipid-bound state, a lipid-anchored protein, a chimeric protein with a fused hydrophobic transmembrane domain and mixtures thereof.

9. The process according to claim 1, wherein no additional lipids besides components of the crude membrane vesicles are added in the process.

10. The process for preparing purified saposin lipoprotein particles comprising the steps of preparing a library according to the process of claim 1 and the additional step of
   f) purifying at least one type of saposin lipoprotein particle from the library, wherein, optionally, the purification of the at least one type of particle in step f) is performed by affinity purification including but not limited to affinity chromatography and/or immunopurification, in particular by using an antigen or tag on a membrane protein present in the particle to be purified and/or wherein, optionally, the purification is performed by chromatography, in particular size-exclusion chromatography; ultracentrifugation; dialysis; contacting with detergent-binding biobeads; or use of concentrators.

11. A library of saposin lipoprotein particles obtained according to the process of claim 1, wherein the particles differ in their membrane protein composition by including different membrane proteins from the crude membrane used as starting material, and wherein the membrane proteins are embedded in the lipids of the crude membrane used as starting material in which they are present and active in vivo.

12. A saposin lipoprotein particle obtained by the process of claim 10, wherein the saposin lipoprotein particle comprises a membrane protein from the crude membrane used as starting material, and wherein the membrane protein is embedded in the lipids of the crude membrane used as starting material in which it is present and active in vivo.

13. A diagnostic method, a cosmetic treatment or for use as a vaccination treatment comprising the step of using the library of particles according to claim 11 or the particle according to claim 12.

14. A method of drug development, drug screening, drug discovery, antibody development, development of therapeutic biologics, membrane or membrane protein purification, membrane protein expression, membrane and/or membrane protein research comprising the step of using the library of particles according to claim 11 or the particle according to claim 12.

15. The process according to claim 3, wherein the detergent is a zwitterionic detergent selected from the group consisting of lauryl-dimethyl amine-oxides (LDAO), Fos-Cholines and CHAPS/CHAPSO.

16. The process according to claim 3, wherein the detergent is an alkyl glycoside selected from the group consisting of short, medium and longer chain alkyl maltosides.

17. The process according to claim 3, wherein the detergent is an n-Dodecyl β-D-maltoside.

18. The process according to claim 1, wherein the particles essentially consist of the at least one lipid binding polypeptide, membrane lipids and/or membrane proteins of the cell or organelle membrane stemming from the cell or the organelle membrane recited in step a).

19. A method of isolating, identifying and/or studying membranes and/or membrane proteins or a method of creating a lipidome or proteome database, the method comprising the step of using the library of particles according to claim 11 or the particle according to claim 12.

20. The process according to claim 1, wherein
   i) the particles are disc-shaped and do not comprise a hydrophilic or aqueous core,
   ii) the particles generally have a maximum diameter of from 3 nm to 150 nm,
   iii) the self-assembly of the particle in step c) is carried out at a pH from 6.0 to 10.0, and/or
   iv) wherein the process comprises in step c) or as a subsequent step d) the purification of the particles by at least partial removal of free membrane lipids, free membrane proteins, free lipid binding polypeptide, unsoluble or aggregated matter and/or detergent, wherein, optionally, the purification is performed by chromatography; ultracentrifugation; dialysis; contacting with detergent-binding biobeads; use of concentrators; affinity purification methods.

21. The process according to claim 1, wherein
   i) the particles are disc-shaped and do not comprise a hydrophilic or aqueous core,
   ii) the particles generally have a maximum diameter of from 3 nm to 100 nm;
   iii) the self-assembly of the particle in step c) is carried out at a pH from 6.0 to 9.0 and/or
   iv) wherein the process comprises in step c) or as a subsequent step d) the purification of the particles by at least partial removal of free membrane lipids, free membrane proteins, free lipid binding polypeptide, unsoluble or aggregated matter and/or detergent, wherein, optionally, the purification is performed by chromatography; ultracentrifugation; dialysis; contacting with detergent-binding biobeads; use of concentrators; affinity purification methods.

22. A method for determining the 3D structure of a membrane protein, the method comprising the step of using the particle according to claim 12.

\* \* \* \* \*

SEQUENCE LISTING

```
<160> NUMBER OF SEQ ID NOS: 46

<210> SEQ ID NO 1
<211> LENGTH: 81
<212> TYPE: PRT
<213> ORGANISM: Homo sapiens

<400> SEQUENCE: 1

Ser Leu Pro Cys Asp Ile Cys Lys Asp Val Val Thr Ala Ala Gly Asp
1               5                   10                  15

Met Leu Lys Asp Asn Ala Thr Glu Glu Ile Leu Val Tyr Leu Glu
            20                  25                  30

Lys Thr Cys Asp Trp Leu Pro Lys Pro Asn Met Ser Ala Ser Cys Lys
        35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser

<210> SEQ ID NO 2
<211> LENGTH: 79
<212> TYPE: PRT
<213> ORGANISM: Homo sapiens

<400> SEQUENCE: 2

Gly Asp Val Cys Gln Asp Cys Ile Gln Met Val Thr Asp Ile Gln Thr
1               5                   10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu
65                  70                  75

<210> SEQ ID NO 3
<211> LENGTH: 80
<212> TYPE: PRT
<213> ORGANISM: Homo sapiens

<400> SEQUENCE: 3

Asp Val Tyr Cys Glu Val Cys Glu Phe Leu Val Lys Glu Val Thr Lys
1               5                   10                  15

Leu Ile Asp Asn Asn Lys Thr Glu Lys Glu Ile Leu Asp Ala Phe Asp
            20                  25                  30

Lys Met Cys Ser Lys Leu Pro Lys Ser Leu Ser Glu Glu Cys Gln Glu
        35                  40                  45

Val Val Asp Thr Tyr Gly Ser Ser Ile Leu Ser Ile Leu Leu Glu Glu
    50                  55                  60

Val Ser Pro Glu Leu Val Cys Ser Met Leu His Leu Cys Ser Gly Thr
65                  70                  75                  80
```

<210> SEQ ID NO 4
<211> LENGTH: 78
<212> TYPE: PRT
<213> ORGANISM: Homo sapiens

<400> SEQUENCE: 4

Gly Phe Cys Glu Val Cys Lys Lys Leu Val Gly Tyr Leu Asp Arg Asn
1               5                   10                  15

Leu Glu Lys Asn Ser Thr Lys Gln Glu Ile Leu Ala Ala Leu Glu Lys
            20                  25                  30

Gly Cys Ser Phe Leu Pro Asp Pro Tyr Gln Lys Gln Cys Asp Gln Phe
        35                  40                  45

Val Ala Glu Tyr Glu Pro Val Leu Ile Glu Ile Leu Val Glu Val Met
    50                  55                  60

Asp Pro Ser Phe Val Cys Leu Lys Ile Gly Ala Cys Pro Ser
65                  70                  75

<210> SEQ ID NO 5
<211> LENGTH: 145
<212> TYPE: PRT
<213> ORGANISM: Homo sapiens

<400> SEQUENCE: 5

Met Ala Thr Trp Ala Leu Leu Leu Ala Ala Met Leu Leu Gly Asn
1               5                   10                  15

Pro Gly Leu Val Phe Ser Arg Leu Ser Pro Glu Tyr Tyr Asp Leu Ala
            20                  25                  30

Arg Ala His Leu Arg Asp Glu Glu Lys Ser Cys Pro Cys Leu Ala Gln
        35                  40                  45

Glu Gly Pro Gln Gly Asp Leu Leu Thr Lys Thr Gln Glu Leu Gly Arg
    50                  55                  60

Asp Tyr Arg Thr Cys Leu Thr Ile Val Gln Lys Leu Lys Lys Met Val
65                  70                  75                  80

Asp Lys Pro Thr Gln Arg Ser Val Ser Asn Ala Ala Thr Arg Val Cys
                85                  90                  95

Arg Thr Gly Arg Ser Arg Trp Arg Asp Val Cys Arg Asn Phe Met Arg
            100                 105                 110

Arg Tyr Gln Ser Arg Val Thr Gln Gly Leu Val Ala Gly Glu Thr Ala
        115                 120                 125

Gln Gln Ile Cys Glu Asp Leu Arg Leu Cys Ile Pro Ser Thr Gly Pro
    130                 135                 140

Leu
145

<210> SEQ ID NO 6
<211> LENGTH: 129
<212> TYPE: PRT
<213> ORGANISM: Sus scrofa

<400> SEQUENCE: 6

Pro Gly Leu Ala Phe Ser Gly Leu Thr Pro Glu His Ser Ala Leu Ala
1               5                   10                  15

Arg Ala His Pro Cys Asp Gly Glu Gln Phe Cys Gln Asn Leu Ala Pro
            20                  25                  30

Glu Asp Pro Gln Gly Asp Gln Leu Leu Gln Arg Glu Glu Leu Gly Leu
        35                  40                  45

Ile Cys Glu Ser Cys Arg Lys Ile Ile Gln Lys Leu Glu Asp Met Val
    50                  55                  60

```
Gly Pro Gln Pro Asn Glu Asp Thr Val Thr Gln Ala Ala Ser Arg Val
 65                  70                  75                  80

Cys Asp Lys Met Lys Ile Leu Arg Gly Val Cys Lys Lys Ile Met Arg
                 85                  90                  95

Thr Phe Leu Arg Arg Ile Ser Lys Asp Ile Leu Thr Gly Lys Lys Pro
            100                 105                 110

Gln Ala Ile Cys Val Asp Ile Lys Ile Cys Lys Glu Lys Thr Gly Leu
        115                 120                 125

Ile

<210> SEQ ID NO 7
<211> LENGTH: 77
<212> TYPE: PRT
<213> ORGANISM: Entamoeba histolytica

<400> SEQUENCE: 7

Ile Pro Val Leu Cys Pro Val Cys Thr Ser Leu Val Gly Lys Leu Ile
 1               5                  10                  15

Asp Leu Val Leu Gly Gly Ala Val Asp Lys Val Thr Asp Tyr Leu Glu
                20                  25                  30

Thr Leu Cys Ala Lys Ala Asp Gly Leu Val Glu Thr Leu Cys Thr Lys
             35                  40                  45

Ile Val Ser Tyr Gly Ile Asp Lys Leu Ile Glu Lys Ile Leu Glu Gly
         50                  55                  60

Gly Ser Ala Lys Leu Ile Cys Gly Leu Ile His Ala Cys
 65                  70                  75

<210> SEQ ID NO 8
<211> LENGTH: 75
<212> TYPE: PRT
<213> ORGANISM: Entamoeba dispar

<400> SEQUENCE: 8

Val Val Cys Pro Val Cys Thr Ser Leu Val Gly Lys Leu Ile Asp Phe
 1               5                  10                  15

Val Ile Gly Gly Ala Val Asp Lys Ala Thr Asp Tyr Leu Glu Thr Leu
                20                  25                  30

Cys Ala Lys Ala Asp Gly Val Ile Glu Thr Val Cys Ser Lys Ile Val
             35                  40                  45

Ser Tyr Gly Ile Asp Lys Leu Ile Glu Lys Ile Ile Glu Gly Gly Ser
         50                  55                  60

Ala Lys Leu Ile Cys Gly Leu Ile His Ala Cys
 65                  70                  75

<210> SEQ ID NO 9
<211> LENGTH: 77
<212> TYPE: PRT
<213> ORGANISM: Entamoeba histolytica

<400> SEQUENCE: 9

Gly Ala Ile Leu Cys Asn Leu Cys Lys Asp Thr Val Leu Val Glu
 1               5                  10                  15

Asn Leu Leu Thr Val Asp Gly Ala Gln Ala Val Arg Gln Tyr Ile Asp
                20                  25                  30

Asn Leu Cys Gly Lys Ala Ser Gly Phe Leu Gly Thr Leu Cys Glu Lys
             35                  40                  45
```

```
Ile Leu Ser Phe Gly Val Asp Glu Leu Val Lys Leu Ile Glu Asn His
         50                  55                  60

Val Asp Pro Val Val Cys Glu Lys Ile His Ala Cys
 65                  70                  75

<210> SEQ ID NO 10
<211> LENGTH: 75
<212> TYPE: PRT
<213> ORGANISM: Entamoeba dispar

<400> SEQUENCE: 10

Gly Leu Cys Asn Leu Cys Lys Asp Thr Val Asn Leu Ile Glu Asn Leu
 1               5                  10                  15

Leu Thr Val Asp Gly Ala Gln Ala Val Arg Gln Tyr Ile Asp Asn Leu
             20                  25                  30

Cys Ala Lys Ala Asp Gly Phe Leu Gly Thr Leu Cys Asn Lys Ile Leu
         35                  40                  45

Ser Phe Gly Val Asp Glu Leu Val Lys Leu Ile Glu Asn His Val Asp
     50                  55                  60

Pro Val Val Ile Cys Glu Lys Ile His Ala Cys
 65                  70                  75

<210> SEQ ID NO 11
<211> LENGTH: 77
<212> TYPE: PRT
<213> ORGANISM: Entamoeba histolytica

<400> SEQUENCE: 11

Gly Glu Ile Leu Cys Asn Leu Cys Thr Gly Leu Ile Asn Thr Leu Glu
 1               5                  10                  15

Asn Leu Leu Thr Thr Lys Gly Ala Asp Lys Val Lys Asp Tyr Ile Ser
             20                  25                  30

Ser Leu Cys Asn Lys Ala Ser Gly Phe Ile Ala Thr Leu Cys Thr Lys
         35                  40                  45

Val Leu Asp Phe Gly Ile Asp Lys Leu Ile Gln Leu Ile Glu Asp Lys
     50                  55                  60

Val Asp Ala Asn Ala Ile Cys Ala Lys Ile His Ala Cys
 65                  70                  75

<210> SEQ ID NO 12
<211> LENGTH: 75
<212> TYPE: PRT
<213> ORGANISM: Entamoeba dispar

<400> SEQUENCE: 12

Ile Val Cys Asn Leu Cys Thr Gly Leu Ile Asn Thr Leu Glu Asn Leu
 1               5                  10                  15

Leu Thr Thr Lys Gly Ala Asp Lys Val Lys Asp Tyr Ile Asp Ser Leu
             20                  25                  30

Cys Asn Lys Ala Ser Gly Phe Ile Ala Thr Leu Cys Thr Lys Val Leu
         35                  40                  45

Asp Phe Gly Val Asp Lys Leu Ile Gln Leu Ile Glu Asp Lys Val Asp
     50                  55                  60

Ala Asn Ala Ile Cys Ala Lys Ile His Ala Cys
 65                  70                  75
```

```
<210> SEQ ID NO 13
<211> LENGTH: 83
<212> TYPE: PRT
<213> ORGANISM: Sus scrofa

<400> SEQUENCE: 13

Gly Leu Ile Cys Glu Ser Cys Arg Lys Ile Ile Gln Lys Leu Glu Asp
1               5                   10                  15

Met Val Gly Pro Gln Pro Asn Glu Asp Thr Val Thr Gln Ala Ala Ser
            20                  25                  30

Arg Val Cys Asp Lys Met Lys Ile Leu Arg Gly Val Cys Lys Lys Ile
        35                  40                  45

Met Arg Thr Phe Leu Arg Arg Ile Ser Lys Asp Ile Leu Thr Gly Lys
    50                  55                  60

Lys Pro Gln Ala Ile Cys Val Asp Ile Lys Ile Cys Lys Glu Lys Thr
65                  70                  75                  80

Gly Leu Ile

<210> SEQ ID NO 14
<211> LENGTH: 78
<212> TYPE: PRT
<213> ORGANISM: Sus scrofa

<400> SEQUENCE: 14

Gly Tyr Phe Cys Glu Ser Cys Arg Lys Ile Ile Gln Lys Leu Glu Asp
1               5                   10                  15

Met Val Gly Pro Gln Pro Asn Glu Asp Thr Val Thr Gln Ala Ala Ser
            20                  25                  30

Gln Val Cys Asp Lys Leu Lys Ile Leu Arg Gly Leu Cys Lys Lys Ile
        35                  40                  45

Met Arg Ser Phe Leu Arg Arg Ile Ser Trp Asp Ile Leu Thr Gly Lys
    50                  55                  60

Lys Pro Gln Ala Ile Cys Val Asp Ile Lys Ile Cys Lys Glu
65                  70                  75

<210> SEQ ID NO 15
<211> LENGTH: 83
<212> TYPE: PRT
<213> ORGANISM: Equus caballus

<400> SEQUENCE: 15

Gly Ile Ala Cys Trp Ser Cys Arg Lys Ile Leu Gln Lys Leu Glu Asp
1               5                   10                  15

Leu Val Gly Glu Gln Pro Asn Glu Ala Thr Ile Asn Glu Ala Ala Ser
            20                  25                  30

Arg Val Cys Arg Asn Leu Gly Leu Leu Arg Gly Ala Cys Lys Lys Ile
        35                  40                  45

Met Arg Thr Cys Leu Arg Leu Ile Ser Arg Asp Ile Leu Ala Gly Lys
    50                  55                  60

Lys Pro Gln Glu Val Cys Val Asp Ile Lys Leu Cys Lys His Lys Ala
65                  70                  75                  80

Gly Leu Ile

<210> SEQ ID NO 16
<211> LENGTH: 84
<212> TYPE: PRT
<213> ORGANISM: Bos taurus
```

<400> SEQUENCE: 16

Gly Leu Leu Cys Gly Ser Cys Gln Arg Ile Ile Gln His Leu Met Asp
1               5                   10                  15

Lys Leu Gly Asp Gln Pro Asp Glu Asn Thr Val Ile Glu Ala Ala Ser
            20                  25                  30

Lys Val Cys Gly Lys Met Gly Pro Leu Lys Gly Leu Cys Lys Ser Ile
        35                  40                  45

Thr Lys Arg Phe Leu Arg Arg Ile Ala Ala Asp Ile Thr Ala Gly Lys
    50                  55                  60

Thr Ser Arg Val Val Cys Glu Asp Ile Lys Met Cys Lys Ser Lys Pro
65                  70                  75                  80

Val Gly Phe Ile

<210> SEQ ID NO 17
<211> LENGTH: 81
<212> TYPE: PRT
<213> ORGANISM: Fasciola hepatica

<400> SEQUENCE: 17

Glu Glu Pro His Leu Asp Ile Ser Leu Cys Glu Ser Cys Thr Asn Thr
1               5                   10                  15

Val Asn Leu Val Lys Arg Leu Leu Gln Asn Ser Val Val Glu Thr His
            20                  25                  30

Ile Arg Tyr Leu Val Lys Tyr Leu Cys Lys Gly Ala Gly Ser Ser Gln
        35                  40                  45

Asp Ala Cys Ile Lys Phe Ile Gln Tyr Glu Val Asp Gly Ala Val Gly
    50                  55                  60

Tyr Leu Ile Gln His Asn Ala Thr Asp Ile Cys His Val Ile Arg Leu
65                  70                  75                  80

Cys

<210> SEQ ID NO 18
<211> LENGTH: 83
<212> TYPE: PRT
<213> ORGANISM: Homo sapiens

<400> SEQUENCE: 18

Gly Arg Asp Tyr Arg Thr Cys Leu Thr Ile Val Gln Lys Leu Lys Lys
1               5                   10                  15

Met Val Asp Lys Pro Thr Gln Thr Ser Val Ser Asn Ala Ala Thr Arg
            20                  25                  30

Val Cys Arg Thr Gly Arg Ser Arg Trp Arg Asp Val Cys Arg Asn Phe
        35                  40                  45

Met Arg Arg Tyr Gln Ser Arg Val Ile Gln Gly Leu Val Ala Gly Glu
    50                  55                  60

Thr Ala Gln Gln Ile Cys Glu Asp Leu Arg Leu Cys Ile Pro Ser Thr
65                  70                  75                  80

Gly Pro Leu

<210> SEQ ID NO 19
<211> LENGTH: 83
<212> TYPE: PRT
<213> ORGANISM: Naegleria fowleri

<400> SEQUENCE: 19

Ser Gly Ile Cys Asn Met Cys Gln Leu Leu Val Thr Gln Val Glu Asn
1 5 10 15

Trp Val Glu Ser Asn Asp Thr Ile Met Thr Leu Glu Lys Lys Leu Glu
20 25 30

Gln Val Cys Ser Val Ile Pro Gly Gln Tyr Ser Ala Leu Cys Thr Tyr
35 40 45

Ala Val Glu Gln Tyr Leu Pro Ile Phe Ile His Gln Val Glu Lys Gln
50 55 60

Phe Pro Ala Leu Thr Ile Cys Gln Asp Val His Leu Cys Ser Ser Ala
65 70 75 80

Gln Ala Ala

<210> SEQ ID NO 20
<211> LENGTH: 73
<212> TYPE: PRT
<213> ORGANISM: Clonorchis sinensis

<400> SEQUENCE: 20

Cys Lys His Cys Lys Thr Leu Val Gly Arg Ile Gln Asp Cys Trp Gln
1 5 10 15

Lys Gly Arg Ala Lys Ser Phe Val Glu Lys Thr Leu Ile Phe Leu Cys
20 25 30

Lys Leu Thr Gly His Ser Glu Glu Gln Cys Thr Glu His Ala Glu Glu
35 40 45

Phe Met Lys His Leu Asp Asp Trp Ile Thr Gly Lys Thr Pro Glu Glu
50 55 60

Leu Cys Arg Ser Leu His Met Cys Lys
65 70

<210> SEQ ID NO 21
<211> LENGTH: 83
<212> TYPE: PRT
<213> ORGANISM: Naegleria fowleri

<400> SEQUENCE: 21

Pro Ser Glu Phe Cys Asp Val Cys Lys Tyr Ala Val Gln Gln Val Asp
1 5 10 15

Gln Leu Ala Leu Gln Asn Glu Ala Ala Ile Gln Asn Ala Leu Leu Ala
20 25 30

Ala Cys Gln Gln Leu Gly Asp Asn Gln Phe Gly Lys Ile Cys Asn Thr
35 40 45

Val Val Leu Val Tyr Gly Asn Glu Leu Val Asn Ala Leu Val Thr Tyr
50 55 60

Glu Asn Pro Thr Arg Val Cys Ser Glu Gln Leu Pro Leu Cys Pro Lys
65 70 75 80

Asn Asn Thr

<210> SEQ ID NO 22
<211> LENGTH: 88
<212> TYPE: PRT
<213> ORGANISM: Caenorhabditis elegans

<400> SEQUENCE: 22

Asn Pro Ala Asn Pro Leu Asn Leu Lys Lys His His Gly Val Phe Cys
1               5                   10                  15

Asp Val Cys Lys Ala Leu Val Glu Gly Gly Glu Lys Val Gly Asp Asp
            20                  25                  30

Asp Leu Asp Ala Trp Leu Asp Val Asn Ile Gly Thr Leu Cys Trp Thr
        35                  40                  45

Met Leu Leu Pro Leu His His Glu Cys Glu Glu Leu Lys Lys Val
    50                  55                  60

Lys Lys Glu Leu Lys Lys Asp Ile Glu Asn Lys Asp Ser Pro Asp Lys
65                  70                  75                  80

Ala Cys Lys Asp Val Asp Leu Cys
                85

<210> SEQ ID NO 23
<211> LENGTH: 83
<212> TYPE: PRT
<213> ORGANISM: Homo sapiens

<400> SEQUENCE: 23

Ser Leu Pro Cys Asp Ile Cys Lys Asp Val Val Thr Ala Ala Gly Asp
1               5                   10                  15

Met Leu Lys Asp Asn Ala Thr Glu Glu Glu Ile Leu Val Tyr Leu Glu
            20                  25                  30

Lys Thr Cys Asp Trp Leu Pro Lys Pro Asn Met Ser Ala Ser Cys Lys
        35                  40                  45

Glu Ile Val Asp Ser Tyr Leu Pro Val Ile Leu Asp Ile Ile Lys Gly
    50                  55                  60

Glu Met Ser Arg Pro Gly Glu Val Cys Ser Ala Leu Asn Leu Cys Glu
65                  70                  75                  80

Ser Leu Gln

<210> SEQ ID NO 24
<211> LENGTH: 83
<212> TYPE: PRT
<213> ORGANISM: Bos taurus

<400> SEQUENCE: 24

Ser Leu Pro Cys Asp Ile Cys Lys Asp Val Ile Thr Ala Ala Gly Asn
1               5                   10                  15

Leu Leu Lys Asp Asn Ala Thr Glu Gln Glu Ile Leu Met Tyr Leu Glu
            20                  25                  30

Arg Thr Cys Asp Trp Leu Pro Lys Pro Asn Met Ser Ala Ser Cys Lys
        35                  40                  45

Glu Ile Val Asp Ser Tyr Leu Pro Val Ile Leu Asp Met Ile Lys Gly
    50                  55                  60

Gln Met Ser His Pro Gly Glu Val Cys Ser Ala Leu Asn Leu Cys Glu
65                  70                  75                  80

Ser Leu Gln

<210> SEQ ID NO 25
<211> LENGTH: 83
<212> TYPE: PRT
<213> ORGANISM: Mus musculus

```
<400> SEQUENCE: 25

Ser Leu Pro Cys Asp Ile Cys Lys Thr Val Thr Glu Ala Gly Asn
1               5                   10                  15

Leu Leu Lys Asp Asn Ala Thr Gln Glu Ile Leu His Tyr Leu Glu
            20                  25                  30

Lys Thr Cys Glu Trp Ile His Asp Ser Ser Leu Ser Ala Ser Cys Lys
            35                  40                  45

Glu Val Val Asp Ser Tyr Leu Pro Val Ile Leu Asp Met Ile Lys Gly
        50                  55                  60

Glu Met Ser Asn Pro Gly Glu Val Cys Ser Ala Leu Asn Leu Cys Gln
65                  70                  75                  80

Ser Leu Gln

<210> SEQ ID NO 26
<211> LENGTH: 83
<212> TYPE: PRT
<213> ORGANISM: Gallus gallus

<400> SEQUENCE: 26

Ser Ile Pro Cys Asp Leu Cys Lys Glu Leu Val Thr Val Val Gly Lys
1               5                   10                  15

Val Leu Lys Asp Asn Gly Thr Glu Asp Glu Ile Arg Ser Tyr Leu Glu
            20                  25                  30

Lys Thr Cys Glu Phe Leu Pro Asp Gln Gly Leu Ala Ser Glu Cys Lys
            35                  40                  45

Glu Ile Val Asp Ser Tyr Leu Pro Val Ile Met Asp Met Ile Lys Glu
        50                  55                  60

Glu Phe Asp Lys Pro Glu Val Val Cys Ser Ala Leu Ser Leu Cys Gln
65                  70                  75                  80

Ser Leu Gln

<210> SEQ ID NO 27
<211> LENGTH: 83
<212> TYPE: PRT
<213> ORGANISM: Danio rerio

<400> SEQUENCE: 27

Thr Val Pro Cys Asp Leu Cys Lys Glu Val Leu Val Val Glu Gln
1               5                   10                  15

Leu Leu Lys Asp Asn Val Thr Glu Ser Glu Leu Leu Gly Tyr Leu Glu
            20                  25                  30

Lys Ala Cys Gln Leu Ile Pro Asp Glu Gly Leu Ala Asn Gln Cys Lys
            35                  40                  45

Glu Ile Val Asp Asn Tyr Phe Pro Val Leu Met Gly Ile Ile Gln Gly
        50                  55                  60

Glu Leu Asp Asp Pro Gly Val Val Cys Gly Ala Leu Gly Leu Cys Val
65                  70                  75                  80

Ser Gln Gln

<210> SEQ ID NO 28
<211> LENGTH: 83
<212> TYPE: PRT
<213> ORGANISM: Xenopus laevis
```

```
<400> SEQUENCE: 28

Ser Met Pro Cys Asp Phe Cys Lys Glu Val Thr Val Leu Gly Asn
1               5                   10                  15

Tyr Leu Lys Asp Asn Ile Thr Gln Asp Glu Ile Lys Gln Tyr Leu Asn
            20                  25                  30

Lys Val Cys Asp Phe Ile Pro Asp Pro Gly Leu Ala Ser Thr Cys Lys
            35                  40                  45

Gln Glu Val Ser Asp Tyr Phe Thr Ile Val Leu Asn Leu Leu Glu Gln
50                      55                  60

Glu Leu Ser Asn Pro Gly Val Leu Cys Ser Ser Leu Gly Leu Cys Thr
65                  70                  75                  80

Ser Leu Gln

<210> SEQ ID NO 29
<211> LENGTH: 80
<212> TYPE: PRT
<213> ORGANISM: Homo sapiens

<400> SEQUENCE: 29

Asp Val Tyr Cys Glu Val Cys Glu Phe Leu Val Lys Glu Val Thr Lys
1               5                   10                  15

Leu Ile Asp Asn Asn Lys Thr Glu Lys Glu Ile Leu Asp Ala Phe Asp
            20                  25                  30

Lys Met Cys Ser Lys Leu Pro Lys Ser Leu Ser Glu Glu Cys Gln Glu
            35                  40                  45

Val Val Asp Thr Tyr Gly Ser Ser Ile Leu Ser Ile Leu Leu Glu Glu
50                      55                  60

Val Ser Pro Glu Leu Val Cys Ser Met Leu His Leu Cys Ser Gly Thr
65                  70                  75                  80

<210> SEQ ID NO 30
<211> LENGTH: 79
<212> TYPE: PRT
<213> ORGANISM: Bos taurus

<400> SEQUENCE: 30

Asp Ile Tyr Cys Glu Val Cys Glu Phe Val Val Lys Glu Val Ala Lys
1               5                   10                  15

Leu Ile Asp Asn Asn Arg Thr Glu Glu Glu Ile Leu His Ala Leu Asp
            20                  25                  30

Lys Val Cys Ser Lys Leu Pro Thr Ser Leu Ala Glu Gln Cys Gln Glu
            35                  40                  45

Val Val Asp Thr Tyr Gly Arg Ser Ile Leu Ser Ile Leu Leu Asp Glu
50                      55                  60

Ala Ser Pro Glu Leu Val Cys Ser Met Leu His Leu Cys Ser Ser
65                  70                  75

<210> SEQ ID NO 31
<211> LENGTH: 79
<212> TYPE: PRT
<213> ORGANISM: Mus musculus

<400> SEQUENCE: 31

Val Ile Leu Cys Gln Thr Cys Gln Phe Val Met Asn Lys Phe Ser Glu
1               5                   10                  15

Leu Ile Val Asn Asn Ala Thr Glu Glu Leu Leu Val Lys Gly Leu Ser
            20                  25                  30
```

Asn Ala Cys Gly Val Leu Pro Asp Pro Ala Arg Thr Lys Cys Gln Glu
            35                  40                  45

Val Val Gly Thr Phe Gly Pro Ser Leu Leu Asp Ile Phe Ile His Glu
50                  55                  60

Val Asn Pro Ser Ser Leu Cys Gly Val Ile Gly Leu Cys Ala Ala
65                  70                  75

<210> SEQ ID NO 32
<211> LENGTH: 80
<212> TYPE: PRT
<213> ORGANISM: Gallus gallus

<400> SEQUENCE: 32

Phe Ser Val Cys Glu Ile Cys Glu Thr Met Val Lys Glu Val Thr Gly
1               5                   10                  15

Leu Leu Glu Ser Asn Lys Thr Glu Glu Glu Ile Val His Glu Met Glu
            20                  25                  30

Val Val Cys Tyr Leu Leu Pro Ala Ser Val Lys Asp Gln Cys Lys Asp
            35                  40                  45

Phe Ile Glu Val Tyr Gly Gln Ala Leu Ile Asp Met Leu Leu Glu Ala
50                  55                  60

Thr Asn Pro Glu Ala Val Cys Val Met Leu Lys Cys Cys Ala Ala Asn
65                  70                  75                  80

<210> SEQ ID NO 33
<211> LENGTH: 79
<212> TYPE: PRT
<213> ORGANISM: Xenopus laevis

<400> SEQUENCE: 33

Asn Val Leu Cys Glu Val Cys Glu Leu Met Val Ser Gln Leu Glu Lys
1               5                   10                  15

Leu Leu Asp Asn Asn Arg Thr Arg Glu Asn Ile Lys His Gly Leu Glu
            20                  25                  30

Lys Val Cys Lys Leu Leu Pro Ser Gln Tyr Thr Gln Lys Cys Glu Asp
            35                  40                  45

Met Ile Glu Glu Tyr Ser Asp Ala Leu Ile Glu Leu Leu Glu Gln Glu
50                  55                  60

Ala Asn Pro Gln Ala Ile Cys Thr Ala Leu Gly Tyr Cys Ser Gly
65                  70                  75

<210> SEQ ID NO 34
<211> LENGTH: 79
<212> TYPE: PRT
<213> ORGANISM: Danio rerio

<400> SEQUENCE: 34

Ser Pro Gln Cys Ala Ile Cys Glu Tyr Val Met Lys Glu Ile Glu Asn
1               5                   10                  15

Met Ile Gln Asp Gln Thr Ser Glu Ala Glu Ile Val Gln Ala Val Glu
            20                  25                  30

Lys Val Cys Asn Ile Leu Pro Ser Thr Leu Thr Ala Gln Cys Lys Asp
            35                  40                  45

Leu Ile Glu Thr Tyr Gly Gln Ala Ile Ile Asp Leu Leu Val Gln Glu
50                  55                  60

Ala Asp Pro Lys Thr Val Cys Ser Phe Leu Ala Leu Cys Ser Gly
65                  70                  75

<210> SEQ ID NO 35
<211> LENGTH: 81
<212> TYPE: PRT
<213> ORGANISM: Homo sapiens

<400> SEQUENCE: 35

Gly Gly Phe Cys Glu Val Cys Lys Lys Leu Val Gly Tyr Leu Asp Arg
1               5                   10                  15

Asn Leu Glu Lys Asn Ser Thr Lys Gln Glu Ile Leu Ala Ala Leu Glu
            20                  25                  30

Lys Gly Cys Ser Phe Leu Pro Asp Pro Tyr Gln Lys Gln Cys Asp Gln
        35                  40                  45

Phe Val Ala Glu Tyr Glu Pro Val Leu Ile Glu Ile Leu Val Glu Val
    50                  55                  60

Met Asp Pro Ser Phe Val Cys Leu Lys Ile Gly Ala Cys Pro Ser Ala
65                  70                  75                  80

His

<210> SEQ ID NO 36
<211> LENGTH: 81
<212> TYPE: PRT
<213> ORGANISM: Bos taurus

<400> SEQUENCE: 36

Gly Gly Phe Cys Glu Val Cys Lys Lys Leu Val Gly Tyr Leu Asp Arg
1               5                   10                  15

Asn Leu Glu Lys Asn Ser Thr Lys Glu Gln Ile Leu Ala Ala Leu Glu
            20                  25                  30

Lys Gly Cys Ser Phe Leu Pro Asp Gln Tyr Arg Lys Gln Cys Asp Gln
        35                  40                  45

Phe Val Thr Glu Tyr Glu Pro Val Leu Ile Glu Ile Leu Val Glu Val
    50                  55                  60

Met Asp Pro Ser Phe Val Cys Leu Lys Ile Gly Ala Cys Pro Ala Ala
65                  70                  75                  80

His

<210> SEQ ID NO 37
<211> LENGTH: 81
<212> TYPE: PRT
<213> ORGANISM: Mus musculus

<400> SEQUENCE: 37

Gly Gly Phe Cys Glu Val Cys Lys Lys Leu Val Leu Tyr Leu Glu His
1               5                   10                  15

Asn Leu Glu Lys Asn Ser Thr Lys Glu Glu Ile Leu Ala Ala Leu Glu
            20                  25                  30

Lys Gly Cys Ser Phe Leu Pro Asp Pro Tyr Gln Lys Gln Cys Asp Asp
        35                  40                  45

Phe Val Ala Glu Tyr Glu Pro Leu Leu Leu Glu Ile Leu Val Glu Val
    50                  55                  60

Met Asp Pro Gly Phe Val Cys Ser Lys Ile Gly Val Cys Pro Ser Ala
65                  70                  75                  80

Tyr

<210> SEQ ID NO 38
<211> LENGTH: 81
<212> TYPE: PRT
<213> ORGANISM: Gallus gallus -continued

<400> SEQUENCE: 38

Gly Gly Phe Cys Asp Ile Cys Lys Met Ile Val Ala Tyr Ala Asp Lys
1               5                   10                  15

Glu Leu Glu Lys Asn Ala Thr Thr Thr Glu Ile Glu Ala Leu Leu Glu
            20                  25                  30

Lys Val Cys His Phe Leu Pro Glu Ser Val Ser Asp Gln Cys Val Gln
        35                  40                  45

Phe Val Glu Gln Tyr Glu Pro Val Val Gln Leu Leu Ala Glu Met
    50                  55                  60

Met Asp Pro Thr Phe Val Cys Thr Lys Leu Gly Val Cys Gly Ala Ala
65                  70                  75                  80

Lys

<210> SEQ ID NO 39
<211> LENGTH: 81
<212> TYPE: PRT
<213> ORGANISM: Danio rerio

<400> SEQUENCE: 39

Gly Gly Phe Cys Asp Val Cys Lys Met Ala Val Arg Tyr Val Asp Gly
1               5                   10                  15

Ile Leu Glu Gln Asn Ala Thr Gln Ser Glu Ile Glu Glu Ala Val Leu
            20                  25                  30

Lys Val Cys Ser Phe Leu Pro Asp Ala Val Lys Asp Glu Cys Asn Gln
        35                  40                  45

Leu Ile Glu Gln Tyr Glu Pro Leu Leu Val Gln Leu Leu Leu Gln Thr
    50                  55                  60

Leu Asp Pro Asp Phe Val Cys Met Lys Leu Gly Ala Cys Pro Glu Ala
65                  70                  75                  80

Val

<210> SEQ ID NO 40
<211> LENGTH: 81
<212> TYPE: PRT
<213> ORGANISM: Xenopus laevis

<400> SEQUENCE: 40

Gly Asp Tyr Cys Ala Val Cys Lys Met Leu Met Arg Tyr Val Asp Glu
1               5                   10                  15

Leu Leu Glu Lys Asn Ala Thr Glu Ile Arg Ile Lys Ala Phe Leu Gly
            20                  25                  30

Arg Ile Cys Asn Phe Leu Pro Asp Ser Met Gln Asn Glu Cys Ser Ala
        35                  40                  45

Leu Val Asn Glu Tyr Glu Pro Leu Phe Ile Gln Leu Leu Leu Glu Ala
    50                  55                  60

Leu Asp Pro Ser Phe Ile Cys Ile Lys Val Asn Leu Cys Gln Asn Lys
65                  70                  75                  80

Lys

<210> SEQ ID NO 41
<211> LENGTH: 79
<212> TYPE: PRT
<213> ORGANISM: Homo sapiens

```
<400> SEQUENCE: 41

Gly Asp Val Cys Gln Asp Cys Ile Gln Met Val Thr Asp Ile Gln Thr
1               5                   10                  15

Ala Val Arg Thr Asn Ser Thr Phe Val Gln Ala Leu Val Glu His Val
            20                  25                  30

Lys Glu Glu Cys Asp Arg Leu Gly Pro Gly Met Ala Asp Ile Cys Lys
        35                  40                  45

Asn Tyr Ile Ser Gln Tyr Ser Glu Ile Ala Ile Gln Met Met Met His
    50                  55                  60

Met Gln Pro Lys Glu Ile Cys Ala Leu Val Gly Phe Cys Asp Glu
65                  70                  75

<210> SEQ ID NO 42
<211> LENGTH: 79
<212> TYPE: PRT
<213> ORGANISM: Bos taurus

<400> SEQUENCE: 42

Gly Asn Val Cys Gln Asp Cys Ile Gln Leu Val Thr Asp Val Gln Glu
1               5                   10                  15

Ala Leu Arg Thr Asn Ser Thr Phe Val Glu Ala Leu Val Asp His Ala
            20                  25                  30

Lys Glu Glu Cys Asp Arg Leu Gly Pro Gly Met Ser Asp Met Cys Lys
        35                  40                  45

Asn Tyr Ile Asn Gln Tyr Ser Glu Val Ala Ile Gln Met Val Met His
    50                  55                  60

Met Gln Pro Lys Glu Ile Cys Val Leu Ala Gly Phe Cys Asp Glu
65                  70                  75

<210> SEQ ID NO 43
<211> LENGTH: 83
<212> TYPE: PRT
<213> ORGANISM: Gallus gallus

<400> SEQUENCE: 43

Glu Asp Val Cys Gln Asp Cys Ile Arg Leu Val Thr Asp Val Gln Glu
1               5                   10                  15

Ala Val Arg Thr Asn Ala Thr Phe Val Lys Ser Leu Val Ala His Ala
            20                  25                  30

Lys Glu Glu Cys Asp Arg Leu Gly Pro Gly Met Ser Asp Met Cys Lys
        35                  40                  45

Ser Tyr Ile Ser Glu Tyr Ser Asp Leu Ala Ile Gln Met Met Met His
    50                  55                  60

Met Lys Asp Gln Gln Pro Lys Asp Ile Cys Ala Met Val Gly Phe Cys
65                  70                  75                  80

Pro Ser Val

<210> SEQ ID NO 44
<211> LENGTH: 83
<212> TYPE: PRT
<213> ORGANISM: Mus musculus

<400> SEQUENCE: 44

Glu Asp Val Cys Gln Asp Cys Met Lys Leu Val Ser Asp Val Gln Thr
1               5                   10                  15

Ala Val Lys Thr Asn Ser Ser Phe Ile Gln Gly Phe Val Asp His Val
            20                  25                  30
```

```
Lys Glu Asp Cys Asp Arg Leu Gly Pro Gly Val Ser Asp Ile Cys Lys
            35                  40                  45

Asn Tyr Val Asp Gln Tyr Ser Glu Val Cys Val Gln Met Leu Met His
 50                  55                  60

Met Gln Asp Gln Gln Pro Lys Glu Ile Cys Val Leu Ala Gly Phe Cys
 65                  70                  75                  80

Asn Glu Val

<210> SEQ ID NO 45
<211> LENGTH: 79
<212> TYPE: PRT
<213> ORGANISM: Danio rerio

<400> SEQUENCE: 45

Gly Asp Val Cys Gln Asp Cys Val Thr Phe Ile Ser Asp Thr Gln Asp
 1               5                  10                  15

Glu Ala Arg Val Asn Ser Ser Phe Ile Asn Thr Leu Ile Ala Gln Val
             20                  25                  30

Glu Asn Gln Cys Glu Leu Leu Gly Pro Gly Met Ser Asp Met Cys Lys
            35                  40                  45

Glu Tyr Ile Ser Gln Tyr Gly Pro Leu Val Phe Gln Gln Leu Met Ser
 50                  55                  60

Met Gln Pro Lys Asp Ile Cys Ala Arg Ala Gly Phe Cys Pro Thr
 65                  70                  75

<210> SEQ ID NO 46
<211> LENGTH: 79
<212> TYPE: PRT
<213> ORGANISM: Xenopus laevis

<400> SEQUENCE: 46

Gly Asp Ile Cys Asn Asp Cys Thr Lys Leu Val Ser Asp Val Gln Asp
 1               5                  10                  15

Ala Leu Arg Ser Asn Ser Ser Phe Ser Lys Lys Leu Val Asp His Phe
             20                  25                  30

Leu Gln Glu Cys Asn Leu Leu Asp Pro Ala Ile Ala Glu Met Cys Lys
            35                  40                  45

Ser Tyr Ile Asn Gln Tyr Ser Asp Ile Ala Ile Gln Val Leu Leu Gln
 50                  55                  60

Met Gln Pro Lys Gln Leu Cys Gly Met Ala Gly Phe Cys Asp Gln
 65                  70                  75
```